(12) United States Patent
Thurston et al.

(10) Patent No.: US 9,999,625 B2
(45) Date of Patent: Jun. 19, 2018

(54) PYRROLOBENZODIAZEPINE COMPOUNDS

(71) Applicant: FEMTOGENIX LIMITED, Welwyn Garden City (GB)

(72) Inventors: David Edwin Thurston, London (GB); Khondaker Mirazur Rahman, London (GB); Paul Joseph Mark Jackson, London (GB)

(73) Assignee: Femtogenix Limited, London (GB)

( * ) Notice: Subject to any disclaimer, the term of this patent is extended or adjusted under 35 U.S.C. 154(b) by 0 days. days.

(21) Appl. No.: 15/308,019

(22) PCT Filed: May 1, 2015

(86) PCT No.: PCT/GB2015/051307
§ 371 (c)(1),
(2) Date: Oct. 31, 2016

(87) PCT Pub. No.: WO2015/166289
PCT Pub. Date: Nov. 5, 2015

(65) Prior Publication Data
US 2017/0050971 A1    Feb. 23, 2017

(30) Foreign Application Priority Data

May 2, 2014   (GB) .................................. 1407816.6

(51) Int. Cl.
*A61K 31/5517*   (2006.01)
*C07D 487/04*   (2006.01)

(52) U.S. Cl.
CPC ........ *A61K 31/5517* (2013.01); *C07D 487/04* (2013.01)

(58) Field of Classification Search
CPC .. A61K 31/55; A61K 31/551; A61K 31/5517; C07D 487/04

(Continued)

(56) References Cited

FOREIGN PATENT DOCUMENTS

| WO | WO-9318045 A1 * | 9/1993 | ........... C07D 519/00 |
|---|---|---|---|
| WO | 0012508 | 3/2000 | |

(Continued)

OTHER PUBLICATIONS

Hartley et al., Cancer Research (2010), 70(17), pp. 6849-6858.*

(Continued)

*Primary Examiner* — Craig D Ricci
*Assistant Examiner* — Janet L. Coppins
(74) *Attorney, Agent, or Firm* — Thomas G. Peterson; Bradley Arant Boult Cummings LLP

(57) ABSTRACT

The invention relates to pyrrolo[2,1-c][1,4]benzodiazepines (PBDs) of formula (I) and in particular to PBD dimers linked through the C1 position, and PBD monomers linked through the C1 position to aromatic groups, and pharmaceutically acceptable salts thereof, which are useful as medicaments, in particular as anti-proliferative agents. (I) and salts or solvates thereof, wherein: the dotted lines indicates the optional presence of a double bond between C1 and C2 or C2 and C3; $R_2$-$R_7$ are independently selected substituent groups; and either: (i) $R_8$ and $R_9$ together form a double bond; (ii) $R_8$ is H and $R_9$ is OH; or (iii) $R_8$ is H and $R_9$ is $OR^A$ and $R^A$ is $C_{1-6}$ alkyl; where $R_1$ has the formula: -X-L-X'-D-X-L-X'- is a linker group and D has the formula (II) or (III): or where the compound is a dimer with each monomer being the same or different and being of formula (I) where the $R_1$ of the first monomer and $R'_1$ or $R'_6$ of the second monomer, or $R_6$ of the first monomer and $R'_1$ of the second monomer, form together a bridge having the formula -X-L-X'- linking the monomers.

(Continued)

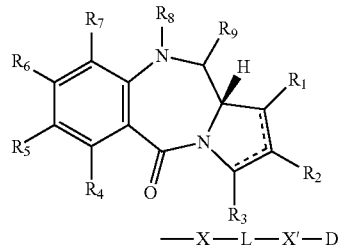

(I)

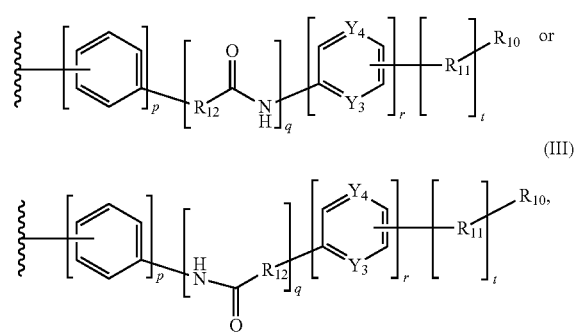

(II)

(III)

20 Claims, 5 Drawing Sheets

(58) Field of Classification Search
USPC .................................................. 514/212.05
See application file for complete search history.

(56) References Cited

FOREIGN PATENT DOCUMENTS

| WO | 2005085250 | 9/2005 | | |
|---|---|---|---|---|
| WO | 201043880 | 4/2010 | | |
| WO | WO 2010043880 A1 * | 4/2010 | ........... | C07D 487/04 |

OTHER PUBLICATIONS

Rudolf, Manfred "International Search Report and Written Opinion—International Application No. PCT/GB2015/051307" dated Aug. 7, 2015; European Patent Office as ISA; pp. 1-11.

Kamal Ahmed, et al "Design and synthesis of C-8 linked pyrrolobenzodiazepine-naphthalimide hybrids as anti-tumour agents," Bioorganic & Medicial Chemistry Letters, Aug. 15, 2002, pp. 1933-1935 vol. 12 No. 15.

Zioga, G., et al. "interaction of the pyrrolobenzodiazepine antitumor agent anthramycin with glutathione: a possible role in metabolism," Database CA [online] Cehmical Abstracts Service, Columbus, OH dates base accession No. 1996:495794.

* cited by examiner

PYRROLOBENZODIAZEPINE COMPOUNDS

CROSS-REFERENCE TO RELATED APPLICATIONS

This application is a national stage under 35 U.S.C. 371 of International Application PCT/GB2015/051307, filed on May 1, 2015 (currently published). International Application PCT/GB2015/051307 cites the priority of British Patent Application No. 1407816.6, filed May 2, 2014 (expired).

FIELD OF THE INVENTION

The invention relates to pyrrolo[2,1-c][1,4]benzodiazepines (PBDs) and in particular to PBD dimers linked through the C1 position, and PBD monomers linked through the C1 position to aromatic groups, and pharmaceutically acceptable salts thereof, which are useful as medicaments, in particular as anti-proliferative agents.

BACKGROUND TO THE INVENTION

The pyrrolobenzodiazepines are a group of compounds some of which have been shown to be sequence-selective DNA minor-groove binding agents. The PBDs were originally discovered in *Streptomyces* species (1-5). They are tricyclic in nature, and are comprised of an anthranilate (A ring), a diazepine (B ring) and a pyrrolidine (C ring) (3). They are characterized by an electrophilic N10=C11 imine group (as shown below) or the hydrated equivalent, a carbinolamine [NH—CH(OH)], or a carbinolamine alkyl ether ([NH—CH(OR, where R=alkyl)] which can form a covalent bond to a C2-amino group of guanine in DNA to form a DNA adduct (6).

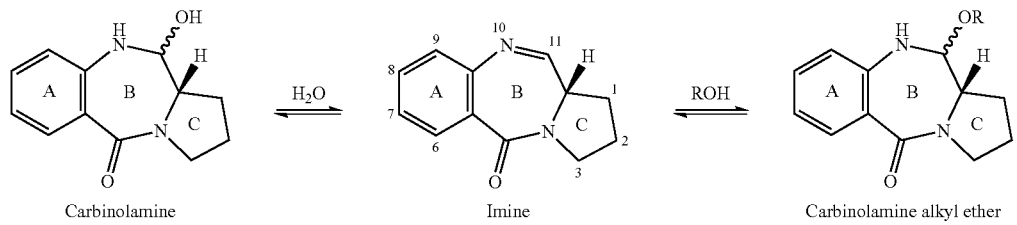

Carbinolamine      Imine      Carbinolamine alkyl ether

The natural products interact in the minor groove of the DNA helix with excellent fit (i.e., good "isohelicity") due to a right-handed longitudinal twist induced by a chiral C11a-position which has the (S)-configuration (6). The DNA adduct has been reported to inhibit a number of biological processes including the binding of transcription factors (7-9) and the function of enzymes such as endonucleases (10, 11) and RNA polymerase (12). PBD monomers (e.g., anthramycin) have been shown by footprinting (6), NMR (13, 14), molecular modeling (15) and X-ray crystallography (16) to span three base pairs and to have a thermodynamic preference for the sequence 5'-Pu-G-Pu-3' (where Pu=purine, and G is the reacting guanine) (17) and a kinetic preference for Py-5-Py (where Py=Pyrimidine).

PBDs are thought to interact with DNA by first locating at a low-energy binding sequence (i.e., a 5'-Pu-G-Pu-3' triplet) through Van der Waals, hydrogen bonding and electrostatic interactions (7). Then, once in place, a nucleophilic attack by the exocyclic C2-amino group of the central guanine occurs to form the covalent adduct (7). Once bound, the PBD remains anchored in the DNA minor groove, avoiding DNA repair by causing negligible distortion of the DNA helix (16). The ability of PBDs to form an adduct in the minor groove and crosslink DNA enables them to interfere with DNA processing and, hence, their potential for use as antiproliferative agents.

A number of monomeric PBD structures have been isolated from *Streptomyces* species, including anthramycin (18) the first PBD, tomamycin (19), and more recently usabamycin (20) from a marine sediment *Streptomyces* species in a marine sediment. This has led to the development of a large range of synthetic analogues which have been reviewed (1, 21). More recently, a number of monomeric PBD structures that are linked through the C8 position to pyrroles and imidazoles have been reported WO 2007/039752, WO 2013/164593 (22-26).

In addition to monomeric PBD structures, a large range of synthetic PBD dimers (i.e. two PBD structures linked via a spacer) have been developed. Early C7- and C8-linked examples (28, 29) were designed to span greater lengths of DNA than the PBD monomers, to have enhanced sequence-selectivity, and to form DNA cross-links that might be more difficult for tumour cells to repair. The synthesis of various PBD dimers has been reviewed (1, 21).

Various PBDs have been shown to act as cytotoxic agents in vitro, for example, WO 00/12508, WO 2004/087711, and as anti-tumour in vivo in animal tumour models, for example, WO 2011/117882, WO 2013/164593. Furthermore, the C8/C8'-linked PBD dimer SJG-136 (29, 32) has completed Phase I clinical trials for leukaemia and ovarian cancer (31) and has shown sufficient therapeutic benefit to progress to Phase II studies.

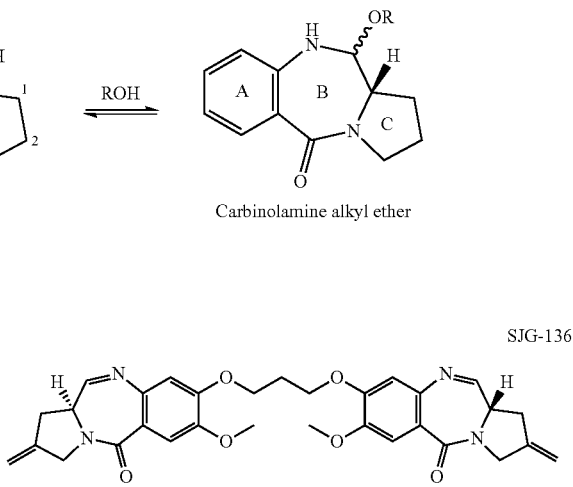

SJG-136

As shown above, PBDs dimers have generally been linked through the A ring, in particular, the C8 position of the A ring has been extensively utilized for the production of PBD dimers (29, 30).

Some attempts have been made to link PBDs dimers via the C ring, with limited success. For example, the C2 position has been investigated in dimer structures as a potential linking point. Examples of this include a C2 dimer produced by Lown et al. (33) which showed poor DNA binding relative to C8/C8'-linked dimers. Furthermore, C8/C2' dimers produced by Kamal et al. (34, 35), showed similarly poor binding with DNA calf thymus melting studies producing results on par with natural monomer structures.

In addition, C3 substitution has been shown to affect binding of the drug in the minor groove, with methylation or butylation of neothramycin A known to prevent interaction of the PBD within the minor groove (2). Bulky moieties on the minor groove facing side of the PBD (i.e., C9, N10-C11) have a profound effect on PBD binding.

Hence, attempts at linking PBD monomers together, or to suitable aromatic substituents, through the C-ring have been disappointing.

The present invention seeks to overcome problem(s) associated with the prior art.

SUMMARY OF THE INVENTION

The present invention provides a compound of formula (I):

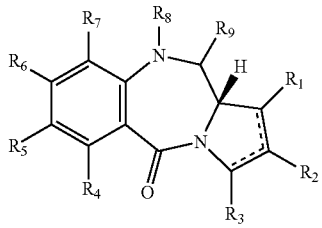

and salts or solvates thereof, wherein:
the dotted lines indicates the optional presence of a double bond between C1 and C2 or C2 and C3;
$R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN;
$R_4$, $R_5$, $R_6$ and $R_7$ are independently selected from H, R, OH, OR, SH, SR, $NH_2$, NHR, NRR', $CO_2H$, $CH_2$—$CO_2H$, $CO_2R$, $CH_2$—$CO_2R$, $NO_2$, $Me_3Sn$ and halo;
R and R' are independently selected from optionally substituted $C_{1-12}$ alkyl, $C_{2-12}$ alkenyl, $C_{3-20}$ heterocyclyl, $C_{4-20}$ heterocyclalkyl, $C_{5-20}$ heterocyclalkenyl, $C_{3-20}$ heteroaryl, $C_{4-32}$ heteroaralkyl, $C_{5-32}$ heteroaralkenyl, $C_{5-20}$ aryl groups $C_{6-32}$ aralkyl and $C_{7-32}$ aralkenyl; and
either:
(i) $R_8$ and $R_9$ together form a double bond;
(ii) $R_8$ is H and $R_9$ is OH; or
(iii) $R_8$ is H and $R_9$ is $OR^A$ and $R^A$ is $C_{1-6}$ alkyl;
and where
(a) the compound is a dimer with each monomer being the same or different and being of formula (I) where $R_1$ of the first monomer and $R'_1$ of the second monomer form together a bridge having the formula -X-L-X'-linking the monomers;
(b) the compound is a dimer with each monomer being the same or different and being of formula (I) where $R_1$ of the first monomer and $R'_6$ of the second monomer, or $R_6$ of the first monomer and $R'_1$ of the second monomer, form together a bridge having the formula -X-L-X'-linking the monomers; and the remaining $R_1$ of the first monomer or $R'_1$ of the second monomer that does not form the bridge is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, ($C_{1-12}$ alkylene)-C(O)NR"R'" and ($C_{2-12}$ alkenylene)-C(O)NR'R" and halo; or
(c) $R_1$ has the formula:

-X-L-X'-D and wherein:
X is selected from O, S, NR", =CR"—, CR"R'", CR"R'"O, C(=O), C(=O)NR", NR"C(=O), O—C(O) and C(O)—O;
L is selected from an amino acid, a peptide chain having from 2 to 6 amino acids, an alkylene chain containing from 2 to 12 carbon atoms which may contain one or more carbon-carbon double or triple bonds, a paraformaldehyde chain —$(OCH_2)_{1-12}$—, a polyethylene glycol chain —$(OCH_2CH_2)_{1-6}$—, which chains may be interrupted by one or more hetero-atoms and/or $C_{3-20}$ heteroaryl and/or $C_{5-20}$ aryl groups;
X' is selected from O, S, NR", =CR"—, CR"R'", CR"R'"O, C(=O), C(=O)NR', NR"C(=O), O—C(O) and C(O)—O or is absent;
R" and R'" are independently selected from H, optionally substituted $C_{1-12}$ alkyl; and
D has the formula (II) or (III):

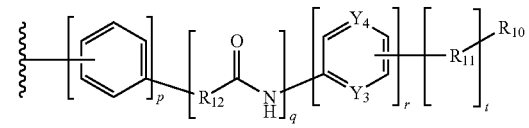

p is 0 or 1;
q is 1, 2, 3, 4, 5 or 6;
r is 0 or 1;
t is 0 or 1
$Y_3$ is N or CH;
$Y_4$ is N or CH; wherein at least one of $Y_3$ and $Y_4$ is CH;
$R_{10}$ is H, Z—R", Z—$CO_2R"$, Z—C(=O)—NH—$(CH_2)_{1-6}$—NR"R'", and Z—C(=O)—NH—$(CH_2)_{16}$—C(=NH)NR"R'";
Z is absent or is selected from $C_{3-20}$ heteroaryl, $C_{1-6}$ alkyl substituted $C_{3-20}$ heteroaryl, —$(CH_2)_n$—$C_{3-20}$ heterocyclyl, and O—$(CH_2)_n$—$C_{3-20}$ heterocyclyl group;
n is 0, 1, 2, 3 or 4;
$R_{1l}$ is an optionally substituted $C_{3-20}$ heteroaryl; and
$R_{12}$ is an optionally substituted $C_{3-20}$ heteroaryl.

In a further aspect, there is provided a compound of the present invention for use in a method of therapy.

In a further aspect, there is provided a compound of the present invention for use in the treatment of a proliferative disease.

In a further aspect, there is provided a pharmaceutical composition comprising a compound of the present invention and a pharmaceutically acceptable carrier or diluent.

In a further aspect, the present invention provides the use of a compound of the present invention in the manufacture of a medicament for treating a proliferative disease.

Definitions

The following abbreviations are used throughout the specification: Alloc allyloxycarbonyl; BAIB bis(acetoxy) iodobenzene; Boc tert-butoxycarbonyl; CBz benzyloxycarbonyl; DBU 1,8-diazabicyclo[5.4.0]undec-7-ene; DHP dihydropyran; DMAP 4-dimethylaminopyridine; DMF dimethylformamide; DMSO dimethylsulfoxide; EDCl 1-Ethyl-3-(3-dimethylaminopropyl)carbodiimide; Et ethyl; $Et_2O$ diethyl ether; EtOAc ethyl acetate; EtOH ethanol; HMDST hexamethyldisilathiane; KOtBu potassium t-butoxide; Me methyl; MeOH methanol; PBDs pyrrolo[2,1-c][1,4]benzodiazepines; PIFA phenyliodine (III) bis[trifluoroacetate]; Ph phenyl; PTSA p-Toluenesulfonic acid; TBAF tetrabutylammonium fluoride; TBDMSCl tert-butyldimethylsilyl chloride; TEA triethylamine; TEMPO (2,2,6,6-tetramethyl-piperidin-1-yl)oxyl; THF tetrahydrofuran; and Troc 2,2,2-Trichloroethyl carbonate.

"Optionally substituted" refers to a parent group which may be unsubstituted or which may be substituted with one or more substituents. Suitably when optional substituents are present the optional substituted parent group comprises from one to three optional substituents.

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Independently selected" is used in the context of statement that, for example, "R and R' are independently selected from $C_{1-12}$ alkyl, $C_{2-12}$ alkenyl, etc." and means that each instance of the functional group R or R' is selected from the listed options independently of any other instance of R or R' in the compound. Hence, for example, a $C_{1-12}$ alkyl may be selected for the first instance of R in the compound and a $C_{2-12}$ alkenyl may be selected for the next instance of R in the compound.

Examples of optional substituents include $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, acetal, acyl, acylamido, acyloxy, amidino, amido, amino, aminocarbonyloxy, azido, carboxy, cyanato, cyano, disulphide, ether, formyl, guanidino, halo, hemiacetal, hemiketal, hydroxamic acid, hydroxyl, imidic acid, imino, isocyano, isocyanato, isothiocyano, ketal, nitro, nitroso, oxo, oxycarbonyl, oxycarboyloxy, phosphate, phosphino, phosphinyl, phosphite, phospho, phosphonate, phosphono, phosphonooxy, phosphorous acid, phosphoramidate, phosphoramidite, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, thioamido, thiocarboxy, thiocyano, thioether, thiolocarboxy, thione, thionocarboxy, uredio, hydroxyl protecting groups and nitrogen protecting groups.

More suitably, the optional substituents may be selected from $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, acetal, acyl, acylamido, acyloxy, amidino, amido, amino, aminocarbonyloxy, azido, carboxy, cyano, ether, formyl, guanidino, halo, hemiacetal, hemiketal, hydroxamic acid, hydroxyl, imidic acid, imino, ketal, nitro, nitroso, oxo, oxycarbonyl, oxycarboyloxy, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, uredio, hydroxyl protecting groups and nitrogen protecting groups.

Examples of substituents are described in more detail below.

$C_{1-7}$ alkyl: refers to straight chain and branched saturated hydrocarbon groups, generally having from 1 to 7 carbon atoms. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

"Alkylene" refers to a divalent radical derived from an alkane which may be a straight chain or branched, as exemplified by —$CH_2CH_2CH_2CH_2$—.

$C_{2-7}$ alkenyl: refers to a hydrocarbon radical having from 2 to 7 carbon atoms and at least one double bond including, but not limited to, ethenyl, 1-propenyl, 2-propenyl, isopropenyl, 1-butenyl, 2-butenyl, 3-butenyl, pentenyl and hexenyl and the like.

The term "alkenylene" refers to a divalent radical derived from an alkenyl which may be a straight chain or branched, containing one or more double bonds, as exemplified by, —$CH_2CH=CH$—, or —$CH_2CH(CH_3)CH=CH—CH_2$—.

$C_{2-7}$ alkynyl: refers to a hydrocarbon radical having from to 2 to 7 carbon atoms and at least one triple bond including, but not limited to, ethynyl, 2-propynyl, 1-butynyl, 2-butynyl and the like.

$C_{5-20}$ aryl: refers to fully unsaturated monocyclic, bicyclic and polycyclic aromatic hydrocarbons having at least one aromatic ring and having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, naphthalenyl, benzocycloheptenyl, azulenyl, biphenylenyl, anthracenyl, phenanthrenyl, naphthacenyl, pyrenyl, groups derived from cycloheptatriene cation, and the like. Examples of aryl groups which comprise fused rings, at least one of which is an aromatic ring, include, but are not limited to, groups derived from indanyl, indenyl, isoindenyl, tetralinyl, acenaphthenyl, fluorenyl, phenalenyl, acephenanthrenyl and aceanthrenyl.

$C_{3-10}$ cycloalkyl: refers to saturated monocyclic and bicyclic hydrocarbon groups, having from 3 to 10 carbon atoms that comprise the ring or rings. Thus, a cycloalkyl represents a cyclic version of an "alkyl". Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached to a parent group or to a substrate at any ring atom unless such attachment would violate valence requirements. Suitably the $C_{3-10}$ cycloalkyl is a monocyclic cycloalkyl group, more suitably a $C_{3-7}$ cycloalkyl is a monocyclic cycloalkyl group.

Examples of monocyclic cycloalkyl groups include cyclopropyl, cyclobutyl, cyclopentyl, cyclohexyl, cycloheptyl, methylcyclopropyl, dimethylcyclopropyl, methylcyclobutyl, dimethylcyclobutyl, methylcyclopentyl, dimethylcyclopentyl and methylcyclohexyl and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]

nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, etc.

$C_{3-10}$ cycloalkenyl: represents a cycloalkyl that contains at least one double bond, including unsaturated monocyclic hydrocarbon compounds such as cyclopropenyl, cyclobutenyl, cyclopentenyl, cyclohexenyl, methylcyclopropenyl, dimethylcyclopropenyl, methylcydobutenyl, dimethylcydobutenyl, methylcydopentenyl, dimethylcydopentenyl and methylcydohexenyl $C_{3-10}$ cycloalkynyl: represents a cylcoalkyl that contains at least one triple bond, including unsaturated monocyclic hydrocarbon compounds such as cyclopropynyl, cyclobutynyl, cyclopentynyl, cyclohexynyl and the like.

"$C_{3-20}$ heterocyclyl": refers to saturated or partially unsaturated monocyclic, bicyclic or polycyclic groups having ring atoms composed of 3 to 20 ring atoms, whether carbon atoms or heteroatoms, of which from 1 to 10 are ring heteroatoms. Suitably, each ring has from 3 to 7 ring atoms and from 1 to 4 ring heteroatoms (e.g., suitably $C_{3-5}$ heterocyclyl refers to a heterocyclyl group having 3 to 5 ring atoms and 1 to 4 heteroatoms as ring members). The ring heteroatoms are independently selected from nitrogen, oxygen, and sulphur.

As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound.

Examples of monocyclic heterocyclyl groups include, but are not limited to, those derived from:
$N_1$: aziridine, azetidine, pyrrolidine, pyrroline, 2H-pyrrole or 3H-pyrrole, piperidine, dihydropyridine, tetrahydropyridine, azepine;
$O_1$: oxirane, oxetane, tetrahydrofuran, dihydrofuran, tetrahydropyran, dihydropyran, pyran, oxepin;
$S_1$: thiirane, thietane, tetrahydrothiophene, tetrahydrothiopyran, thiepane;
$O_2$: dioxoiane, dioxane, and dioxepane;
$O_3$: trioxane;
$N_2$: imidazoiidine, pyrazolidine, imidazoline, pyrazoline, piperazine:
$N_1O_1$: tetrahydrooxazole, dihydrooxazole, tetrahydroisoxazole, dihydroisoxazole, morpholine, tetrahydrooxazine, dihydrooxazine, oxazine;
$N_1S_1$: thiazoline, thiazolidine, thiomorpholine;
$N_2O_1$: oxadiazine;
$O_1S_1$: oxathiole and oxathiane (thioxane); and
$N_1O_1S_1$: oxathiazine.

Examples of substituted monocyclic heterocyclyl groups include those derived from saccharides, in cyclic form, for example, furanoses, such as arabinofuranose, lyxofuranose, ribofuranose, and xylofuranse, and pyranoses, such as aliopyranose, altropyranose, glucopyranose, mannopyranose, gulopyranose, idopyranose, galactopyranose, and talopyranose.

"$C_{3-20}$ Heteroaryl": refers to unsaturated monocyclic, bicyclic or polycyclic aromatic groups comprising from 3 to 20 ring atoms, whether carbon or heteroatoms, of which from 1 to 10 are ring heteroatoms. Suitably, each ring has from 3 to 7 ring atoms and from 1 to 4 ring heteroatoms. Suitably each ring heteroatom is independently selected from nitrogen, oxygen, and sulfur. The bicyclic and polycyclic may include any bicyclic or polycyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:
$N_1$: pyrrole, pyridine;
$O_1$: furan;
$S_1$: thiophene;
$N_1O_1$: oxazole, isoxazole, isoxazine;
$N_2O_1$: oxadiazole (e.g. 1-oxa-2,3-diazolyl, 1-oxa-2,4-diazolyl, 1-oxa-2,5-diazolyl, 1-oxa-3,4-diazolyl);
$N_3O_1$: oxatriazole;
$N_1S_1$: thiazole, isothiazole;
$N_2$: imidazole, pyrazole, pyridazine, pyrimidine (e.g., cytosine, thymine, uracil), pyrazine;
$N_3$: triazole, triazine; and,
$N_4$: tetrazole.

Examples of heteroaryl which comprise fused rings, include, but are not limited to, those derived from:
$O_1$: benzofuran, isobenzofuran, chromene, isochromene, chroman, isochroman, dibenzofuran, xanthene;
$N_1$: indole, isoindole, indolizine, isoindoline, quinoline, isoquinoline, quinolizine, carbazole, acridine, phenanthridine;
$S_1$: benzothiofuran, dibenzothiophene, thioxanthene;
$N_1O_1$: benzoxazole, benzisoxazole, benzoxazine, phenoxazine;
$N_1S_1$: benzothiazole, phenothiazine;
$O_1S_1$: phenoxathiin;
$N_2$: benzimidazole, indazole, benzodiazine, pyridopyridine, quinoxaline, quinazoline, cinnoline, phthalazine, naphthyridine, benzodiazepine, carboline, perimidine, pyridoindole, phenazine, phenanthroline, phenazine;
$O_2$: benzodioxole, benzodioxan, oxanthrene;
$S_2$: thianthrene
$N_2O_1$: benzofurazan;
$N_2S_1$: benzothiadiazole
$N_3$: benzotriazole
$N_4$: purine (e.g., adenine, guanine), pteridine;

The optional substituents $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, whether alone or part of another substituent, may themselves optionally be substituted with one or more groups (suitably, optionally substituted with from one to three) selected from themselves and from acetal, acyl, acylamido, acyloxy, amidino, amido, amino, aminocarbonyloxy, azido, carboxy, cyanato, cyano, disulphide, ether, formyl, guanidino, halo, hemiacetal, hemiketal, hydroxamic acid, hydroxyl, imidic acid, imino, isocyano, isocyanato, isothiocyano, ketal, nitro, nitroso, oxo, oxycarbonyl, oxycarboyloxy, phosphate, phosphino, phosphinyl, phosphite, phospho, phosphonate, phosphono, phosphonooxy, phosphorous acid, phosphoramidate, phosphoramidite, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, thioamido, thiocarboxy, thiocyano, thioether, thiolocarboxy, thione, thionocarboxy, uredio, hydroxyl protecting groups and nitrogen protecting groups.

For example, when an alkyl group is optionally substituted with one or more aryl groups it forms aralkyl group. Suitably a $C_{6-32}$ aralkyl where the alkyl group and aryl group(s) combined have from 6 to 32 carbon atoms. Similarly, when an alkyl group is optionally substituted with one or more heteroaryl groups it forms heteroaralkyl group.

Suitably a $C_{4-32}$ heteroaralkyl group where number of ring atoms in the heteroaryl group plus the number of carbon atoms in the alkyl group is from 4 to 32.

Examples of substituents are described in more detail below.

Acetal: $-CHC(OR^{X1})(OR^{X2})$, wherein $R^{X1}$ and $R^{X2}$ are independently acetal substituents, for example, a $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably a $C_{1-7}$ alkyl, or, in the case of a "cyclic" acetal group, $R^{X1}$ and $R^{X2}$, taken together with the two oxygen atoms to which they are attached, and the carbon atoms to which they are attached, form a heterocyclic ring having from 4 to 8 ring atoms. Examples of acetal groups include, but are not limited to, $-CH(OCH_3)_2$, $-CH(OCH_2CH_3)_2$, and $-CH(OCH_3)(OCH_2CH_3)$.

Acyl: $-C(=O)R^{X3}$, wherein $R^{X3}$ is an acyl substituent, for example, a $C_{1-7}$ alkyl (also referred to as $C_{1-7}$ alkylacyl or $C_{1-7}$ alkanoyl), $C_{2-7}$ alkenyl, $C_{2-7}$ alkynyl, $C_{5-20}$ aryl (also referred to as $C_{5-20}$ arylacyl), $C_{3-10}$ cycloalkyl, $C_{3-10}$ cycloalkenyl, $C_{3-10}$ cycloalkynyl, $C_{3-20}$ heterocyclyl (also referred to as $C_{3-20}$ heterocyclyl acyl), $C_{3-20}$ heteroaryl (also referred to as $C_{3-20}$ heteroarylacyl), more suitably a $C_{1-7}$ alkyl. Examples of acyl groups include, but are not limited to, $-C(=O)CH_3$ (acetyl), $-C(=O)CH_2CH_3$ (propionyl), $-C(=O)C(CH_3)_3$ (t-butyryl), and $-C(=O)Ph$ (benzoyl, phenone).

Acylamido: $-NR^{X4}C(=O)R^{X5}$, wherein $R^{X4}$ and $R^{X5}$ are suitably independently selected from a hydrogen, a $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably a hydrogen or a $C_{1-7}$ alkyl, or, in the case of a "cyclic" acylamido group, $R^{X4}$ and $R^{X5}$, taken together with the nitrogen atom to which they are attached, and the carbon atoms to which they are attached, form a heterocyclic ring having from 4 to 8 ring atoms. Examples of acylamido groups include, but are not limited to, $-NHC(=O)CH_3$, $-NHC(=O)CH_2CH_3$, $-NHC(=O)Ph$; and the cyclic groups succinimidyl, maleimidyl, and phthalimidyl:

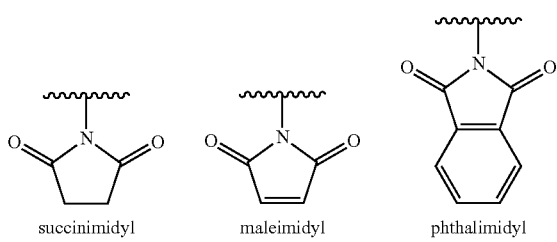

succinimidyl  maleimidyl  phthalimidyl

Acyloxy (reverse ester): $-OC(=O)R^{X3}$, wherein $R^{X3}$ is an acyloxy substituent and suitably has any of the options listed above with regard to acyl groups. Examples of acyloxy groups include, but are not limited to, $-OC(=O)CH_3$ (acetoxy), $-OC(=O)CH_2CH_3$, $-OC(=O)C(CH_3)_3$, $-OC(=O)Ph$, and $-OC(=O)CH_2Ph$.

Amidino: $-C(=NR^{X6})NR^{X4}R^{X5}$, wherein $R^{X4}$ and $R^{X5}$ are suitably independently selected from the groups as listed above for acylamido, and wherein $R^{X6}$ is selected from a hydrogen, a $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-20}$ heteroaryl, suitably a hydrogen or a $C_{1-7}$ alkyl. Examples of amidine groups include, but are not limited to, $-C(=NH)NH_2$, $-C(=NH)N(CH_3)_2$ and $-C(=NCH_3)N(CH_3)_2$.

Amido: $-C(=O)NR^{X4}R^{X5}$, wherein $R^{X4}$ and $R^{X5}$ are suitably independently selected from the groups as listed above for acylamido. Examples of amido groups include, but are not limited to, $-C(=O)NH_2$, $-C(=O)NHCH_3$, $-C(=O)N(CH_3)_2$, $-C(=O)NHCH_2CH_3$, and $-C(=O)N(CH_2CH_3)_2$, as well as amido groups in which $R^{X4}$ and $R^{X5}$, together with the nitrogen atom to which they are attached, form a heterocyclic structure as in, for example, piperidinocarbonyl, morpholinocarbonyl, thiomorpholinocarbonyl, and piperazinocarbonyl.

Amino: $-NR^{X4}R^{X5}$, wherein $R^{X4}$ and $R^{X5}$ are suitably independently selected from the groups as listed above for acylamido. Amino groups may be primary (both $R^{X4}$ and $R^{X5}$ are H), secondary (only one of $R^{X4}$ and $R^{X5}$ is H), or tertiary (neither $R^{X4}$ and $R^{X5}$ is H), and in cationic form, may be quaternary ($-^{+}NR^{X4}R^{X5}R^{X6}$ wherein $R^{X6}$ is suitably selected from the same groups as listed above for amidino). Examples of amino groups include, but are not limited to, $-NH_2$, $-NHCH_3$, $-NHC(CH_3)_2$, $-N(CH_3)_2$, $-N(CH_2CH_3)_2$, and $-NHPh$. Examples of cyclic amino groups include, but are not limited to, aziridino, azetidino, pyrrolidino, piperidino, piperazino, morpholino, and thiomorpholino.

Aminocarbonyloxy: $-OC(=O)NR^{X4}R^{X5}$, wherein $R^{X4}$ and $R^{X5}$ are suitably independently selected from the groups as listed above for acylamido. Examples of aminocarbonyloxy groups include, but are not limited to, $-OC(=O)NH_2$, $-OC(=O)NHCH_3$, $-OC(=O)N(CH_3)_2$, and $-OC(=O)N(CH_2CH_3)_2$.

Azido: $-N_3$.

Carboxy: $-C(=O)OH$

Cyanato: $-OCN$.

Cyano: $-CN$.

Disulfide: $-SS-R^{X3}$, wherein $R^{X3}$ is suitably selected from the groups as listed above for acyl. Examples of disulphide groups include $C_{1-7}$ alkyl disulfide groups which include, but are not limited to, $-SSCH_3$ and $-SSCH_2CH_3$.

Ether: $-OR^{X3}$, wherein $R^{X3}$ is suitably selected from the groups as listed above for acyl. More suitably, $R^{X3}$ is an alkyl group, for example, a $C_{1-7}$ alkyl group, resulting in $-OR^{X3}$ being an alkoxy group. Examples of $C_{1-7}$ alkoxy groups include, but are not limited to, $-OCH_3$ (methoxy), $-OCH_2CH_3$ (ethoxy), $-OCH_2CH_2CH_3$ (n-propoxy), $-OCH_2(CH_3)_2$ (isopropoxy), $-OCH_2CH_2CH_2CH_3$ (n-butoxy), $-O(OCH(CH_3)-CH_2CH_3$ (sec-butoxy), $-OCH_2CH(CH_3)_2$ (isobutoxy), and $-OC(CH_3)_3$ (tert-butoxy).

Formyl: $-C(=O)H$.

Guanidino: $-NH-C(=NH)NH_2$.

Halo: $-F$, $-Cl$, $-Br$, and $-I$.

Hemiacetal: $-CH(OH)(OR^{X3})$, wherein $R^{X3}$ is suitably selected from the groups as listed above for acyl. Examples of hemiacetal groups include, but are not limited to, $-CH(OH)(OCH_3)$ and $-CH(OH)(OCH_2CH_3)$.

Hemiketal: —CR$^{X3}$(OH)(OR$^{X3}$), wherein each R$^{X3}$ is suitably independently selected from the groups as listed above for acyl. Examples of hemiketal groups include, but are not limited to, —C(CH$_3$)(OH)(OCH$_3$), —C(CH$_2$CH$_3$)(OH)(OCH$_3$), —C(CH$_3$)(OH)(OCH$_2$CH$_3$), and —C(CH$_2$CH$_3$)(OH)(OCH$_2$CH$_3$).

Hydroxamic acid: —C(=NOH)OH.

Hydroxyl: —OH.

Imidic acid: —C(=NH)OH.

Imino: =NR$^{X4}$, wherein R$^{X4}$ is suitably selected from the groups as listed above for acylamido. Examples of imino groups include, but are not limited to, =NH, =NCH$_3$, =NCH$_2$CH$_3$, and =NPh.

Isocyano: —NC.

Isocyanato: —NCO.

Isothiocyano: —NCS.

Ketal: —CR$^{X3}$(OR$^{X1}$)(OR$^{X2}$), where R$^{X1}$ and R$^{X2}$ are suitably selected from the groups as listed above for acetals, and R$^{X3}$ is suitably selected from the groups as listed above for acyl. Examples ketal groups include, but are not limited to, —C(CH$_3$)(OCH$_3$)$_2$, —C(CH$_3$)(OCH$_2$CH$_3$)$_2$, —C(CH$_3$)(OCH$_3$)(OCH$_2$CH$_3$), —C(CH$_2$CH$_3$)(OCH$_3$)$_2$, —C(CH$_2$CH$_3$)(OCH$_2$CH$_3$)$_2$, and —C(CH$_2$CH$_3$)(OCH$_3$)(OCH$_2$CH$_3$).

Nitro: —NO$_2$.

Nitroso: —NO.

Oxo: =O.

Oxycarbonyl (ester): —C(=O)OR$^{X3}$, wherein R$^{X3}$ is suitably selected from the groups as listed above for acyl. Examples of ester groups include, but are not limited to, —C(=O)OCH$_3$, —C(=O)OCH$_2$CH$_3$, —C(=O)OC(CH$_3$)$_3$, and —C(=O)OPh.

Oxycarboyloxy: —OC(=O)OR$^{X3}$, where R$^{X3}$ is suitably selected from the groups as listed above for acyl. Examples of oxycarboyloxy groups include, but are not limited to, —OC(=O)OCH$_3$, —OC(=O)OCH$_2$CH$_3$, —OC(=O)OC(CH$_3$)$_3$, and —OC(=O)OPh.

Phosphate: OP(=O)(OR$^{X7}$)(OR$^{X8}$), wherein R$^{X7}$ and R$^{X8}$ are suitably independently selected from hydrogen, C$_{1-7}$ alkyl, C$_{2-7}$ alkenyl, C$_{2-7}$ alkynyl, C$_{5-20}$ aryl, C$_{3-10}$ cycloalkyl, C$_{3-10}$ cycloalkenyl, C$_{3-10}$ cycloalkynyl, C$_{3-20}$ heterocyclyl, C$_{3-20}$ heteroaryl, suitably hydrogen, C$_{1-7}$ alkyl, C$_{5-20}$ aryl or C$_{3-20}$ heteroaryl. Examples of phosphate groups include, but are not limited to, —OP(=O)(OCH$_3$)$_2$, —OP(=O)(OCH$_2$CH$_3$)$_2$, —OP(=O)[OC(CH$_3$)$_3$]$_2$ and —OP(=O)(OPh)$_2$.

Phosphino: —PR$^{X7}$R$^{X8}$, wherein R$^{X7}$ and R$^{X8}$ are suitably selected from the groups as listed above for phosphate. Examples of phosphino groups include, but are not limited to, —PH$_2$, —P(CH$_3$)$_2$, —P(CH$_2$CH$_3$)$_2$, —P(C(CH$_3$)$_3$)$_2$, and —P(Ph)$_2$.

Phosphinyl: P(=O)R$^{X9}$R$^{X10}$), wherein R$^{X9}$ and R$^{X10}$ are suitably independently selected from C$_{1-7}$ alkyl, C$_{2-7}$ alkenyl, C$_{2-7}$ alkynyl, C$_{5-20}$ aryl, C$_{3-10}$ cycloalkyl, C$_{3-10}$ cycloalkenyl, C$_{3-10}$ cycloalkynyl, C$_{3-20}$ heterocyclyl, C$_{3-20}$ heteroaryl, suitably C$_{1-7}$ alkyl, C$_{5-20}$ aryl or C$_{3-20}$ heteroaryl. Examples of phosphinyl groups include, but are not limited to, —P(=O)(CH$_3$)$_2$, —P(=O)(CH$_2$CH$_3$)$_2$, —P(=O)[C(CH$_3$)$_3$]$_2$ and —P(=O)(Ph)$_2$. —

Phosphite: —OP(OR$^{X7}$)(OR$^{X8}$), wherein R$^{X7}$ and R$^{X8}$ are suitably selected from the groups as listed above for phosphate. Examples of phosphite groups include, but are not limited to, —OP(OCH$_3$)$_2$, —OP(OCH$_2$CH$_3$)$_2$, —OP[OC(CH$_3$)$_3$]$_2$ and —OP(OPh)$_2$—

Phospho: —P(=O)$_2$.

Phosphonate: —P(=O(OR$^{X7}$)(OR$^{X8}$), wherein R$^{X7}$ and R$^{X8}$ are suitably selected from the groups as listed above for phosphate. Examples of phosphonate groups include, but are not limited to, —P(=O)(OCH$_3$)$_2$, —P(=O)(OCH$_2$CH$_3$)$_2$, —P(=O)[OC(CH$_3$)$_3$]$_2$ and —P(=O)(OPh)$_2$.

Phosphono: —P(=O)(OH)$_2$.

Phosphonooxy: —OP(=O)(OH)$_2$.

Phosphorous acid: —OP(OH)$_2$.

Phosphoramidate: —OP(=O)(OR$^{X11}$)—NR$^{X12}$R$^{X13}$, where R$^{X11}$, R$^{X12}$ and R$^{X13}$ are phosphoramidate substituents, for example, H, C$_{1-7}$ alkyl (optionally substituted), C$_{2-7}$ alkenyl (optionally substituted), C$_{2-7}$ alkynyl (optionally substituted), C$_{5-20}$ aryl, C$_{3-10}$ cycloalkyl, C$_{3-10}$ cycloalkenyl, C$_{3-10}$ cycloalkynyl, C$_{3-20}$ heterocyclyl, C$_{3-20}$ heteroaryl, suitably H, C$_{1-7}$ alkyl, a C$_{5-20}$ aryl or a C$_{3-20}$ heteroaryl. Examples of phosphoramidate groups include, but are not limited to, —OP(=O)(OCH$_2$CH$_3$)—N(CH$_3$)$_2$, —OP(=O)(OCH$_2$CH$_3$)—N[CH(CH$_3$)$_2$]$_2$, and —OP(=O)(OCH$_2$CH$_2$CN)—N[CH(CH$_3$)$_2$]$_2$.

Phosphoramidite: —OP(OR$^{X11}$)—NR$^{X12}$R$^{X13}$, where R$^{X11}$, R$^{X12}$ and R$^{X13}$ are suitably selected from the groups as listed above for phosphoramidate. Examples of phosphoramidite groups include, but are not limited to, —OP(OCH$_2$CH$_3$)—N(CH$_3$)$_2$, —OP(OCH$_2$CH$_3$)—N[CH(CH$_3$)$_2$]$_2$, and —OP(OCH$_2$CH$_2$CN)—N[CH(CH$_3$)$_2$]$_2$.

Sulfamino: —NR$^{X3}$S(=O)$_2$OH, wherein R$^{X3}$ is suitably selected from the groups as listed above for acyl groups. Examples of sulfamino groups include, but are not limited to, —NHS(=O)$_2$OH and —N(CH$_3$)S(=O)$_2$OH.

Sulfamyl: —S(=O)NR$^{X4}$R$^{X5}$, wherein R$^{X4}$ and R$^{X5}$ are suitably independently selected from the groups as listed above for acylamido. Examples of sulfamyl groups include, but are not limited to, —S(=O)NH$_2$, —S(=O)NHCH$_3$, —S(=O)N(CH$_3$)$_2$, —S(=O)NHCH$_2$CH$_3$, —S(=O)N(CH$_2$CH$_3$)$_2$, and —S(=O)NHPh.

Sulfate: —OS(=O)$_2$OR$^{X3}$; wherein R$^{X3}$ is suitably selected from the groups as listed above for acyl groups. Examples of sulfate groups include, but are not limited to, —OS(=O)$_2$OCH$_3$ and —OS(=O)$_2$OCH$_2$CH$_3$.

Sulfhydryl: —SH.

Sulfinamino: —NR$^{X3}$S(=O)R$^{X4}$, wherein R$^{X3}$ is suitably selected from the groups as listed above for acyl groups, and R$^{X4}$ is suitably selected from the groups as listed above for acylamido. Examples of sulfinamino groups include, but are not limited to, —NHS(=O)CH$_3$ and —N(CH$_3$)S(=O)Ph.

Sulfinate: —S(=O)OR$^{X3}$; wherein R$^{X3}$ is suitably selected from the groups as listed above for acyl groups. Examples of sulfinate groups include, but are not limited to, —S(=O)OCH$_3$ and —S(=O)OCH$_2$CH$_3$.

Sulfino: —S(=O)OH, —SO$_2$H.

Sulfinyl: —S(=O)R$^{X3}$; wherein R$^{X3}$ is suitably selected from the groups as listed above for acyl groups. Examples of sulfinyl groups include, but are not limited to, —S(=O)CH$_3$ and —S(=O)CH$_2$CH$_3$.

Sulfinyloxy: —OS(=O)R$^{X3}$; wherein R$^{X3}$ is suitably selected from the groups as listed above for acyl groups. Examples of sulfinyloxy groups include, but are not limited to, —OS(=O)CH$_3$ and —OS(=O)CH$_2$CH$_3$.

Sulfo: —S(=O)$_2$OH, —SO$_3$H.

Sulfonamido: —S(=O)$_2$NR$^{X4}$R$^{X5}$, wherein R$^{X4}$ and R$^{X5}$ are suitably independently selected from the groups as listed above for acylamido. Examples of sulfonamido groups include, but are not limited to, —S(=O)$_2$NH$_2$, —S(=O)$_2$NHCH$_3$, —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfonamino: —NR$^{X4}$S(=O)$_2$R$^{X3}$, where R$^{X3}$ is suitably selected from the groups as listed above for acyl groups and R$^{X4}$ is suitably selected from the groups as listed above for acylamido. Examples of sulfonamino groups include, but are not limited to, —NHS(=O)$_2$CH$_3$ and —N(CH$_3$)S(=O)$_2$Ph.

Sulfonate: —S(=O)$_2$R$^{X3}$, where R$^{X3}$ is suitably selected from the groups as listed above for acyl groups. Examples of sulfonate groups include, but are not limited to, —S(=O)$_2$ OCH$_3$ and —S(=O)$_2$OCH$_2$CH$_3$.

Sulfonyl: —S(=O)$_2$R$^{X3}$, where R$^{X3}$ is suitably selected from the groups as listed above for acyl groups. More suitably R$^{X3}$ is a C$_{1-7}$ alkyl group, including, for example, a fluorinated or perfluorinated C$_{1-7}$ alkyl group. Examples of sulfone groups include, but are not limited to, —S(=O)$_2$CH$_3$, —S(=O)$_2$CF$_3$, —S(=O)$_2$CH$_2$CH$_3$, —S(=O)$_2$C$_4$F$_9$, —S(=O)$_2$CH$_2$CF$_3$, —S(=O)$_2$CH$_2$CH$_2$NH$_2$, —S(=O)$_2$Ph, 4-methylphenylsulfonyl (tosyl), 4-chlorophenyl-sulfonyl (closyl), 4-bromophenylsulfonyl (brosyl), 4-nitrophenyl (nosyl), 2-naphthalenesulfonate (napsyl), and 5-dimethyl-aminonaphthalen-1-ylsulfonate (dansyl).

Sulfonyloxy: —OS(=O)$_2$R$^{X3}$, where R$^{X3}$ is suitably selected from the groups as listed above for acyl groups. Examples of sulfonyloxy groups include, but are not limited to, —OS(=O)$_2$CH$_3$ and —OS(=O)$_2$ CH$_2$CH$_3$.

Thioamido: —C(=S)NR$^{X4}$R$^{X5}$, where R$^{X4}$ and R$^{X5}$ are suitably independently selected from the groups as listed above for acylamido. Examples of amido groups include, but are not limited to, —C(=S)NH$_2$, —C(=S)NHCH$_3$, —C(=S)N(CH$_3$)$_2$, —C(=S)NHCH$_2$CH$_3$, and —C(=S)N(CH$_2$CH$_3$)$_2$.

Thiocarboxy: —C(=S)SH.

Thiocyano: —SCN.

Thioether: —SR$^{X3}$, wherein R$^{X3}$ is suitably selected from the groups as listed above for acyl. Examples of thioether groups include, but are not limited to, —SCH$_3$ and SCH$_2$CH$_3$.

Thiolocarboxy: —C(=O)SH.

Thione: =S.

Thionocarboxy: —C(=S)OH.

Ureido: —N(R$^{X6}$)CONR$^{X4}$R$^{X5}$, wherein R$^{X4}$ and R$^{X5}$ are suitably independently selected from the groups as listed above for acylamido, and R$^{X6}$ is suitably selected from the groups listed above for amidino. Examples of ureido groups include, but are not limited to, —NHCONH$_2$, —NHCONHCH$_3$, —NHCONHCH$_2$CH$_3$, NHCON(CH$_3$)$_2$, NHCON(CH$_2$CH$_3$)$_2$, —NCH$_3$CONH$_2$, —NCH$_3$CONHCH$_3$, —NCH$_3$CONHCH$_2$CH$_3$, —NCH$_3$CON(CH$_3$)$_2$, and —NCH$_3$CON(CH$_2$CH$_3$)$_2$.

Nitrogen Protecting Groups

Nitrogen protecting groups are well known in the art. Preferred nitrogen protecting groups are carbamate protecting groups that have the general formula:

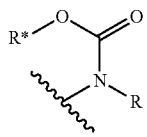

A large number of possible carbamate nitrogen protecting groups are listed on pages 706 to 771 of Wuts, P. G. M. and Greene, T. W., Protective Groups in Organic Synthesis, 4$^{th}$ Edition, Wiley-Interscience, 2007, and in P. Kocienski, Protective Groups, 3rd Edition (2005) which are incorporated herein by reference.

Particularly preferred protecting groups include Alloc (allyloxycarbonyl), Troc (2,2,2-Trichloroethyl carbonate), Teoc [2-(Trimethylsily)ethoxycarbony], BOC (tert-butyloxycarbonyl), Doc (2,4-dimethylpent-3-yloxycarbonyl), Hoc (cyclohexyloxy-carbonyl), TcBOC (2,2,2-trichloro-tert-butyloxycarbonyl), Fmoc (9-fluoroenylmethyloxycarbonyl), 1-Adoc (1-Adamantyloxycarbonyl) and 2-Adoc (2-adamantyloxycarbonyl).

Hydroxyl Protecting Groups

Hydroxyl protecting groups are well known in the art, a large number of suitable groups are described on pages 16 to 366 of Wuts, P. G. M. and Greene, T. W., Protective Groups in Organic Synthesis, 4$^{th}$ Edition, Wiley-Interscience, 2007, and in P. Kocienski, Protective Groups, 3rd Edition (2005) which are incorporated herein by reference.

Classes of particular interest include silyl ethers, methyl ethers, alkyl ethers, benzyl ethers, esters, benzoates, carbonates, and sulfonates.

Particularly preferred protecting groups include THP (tetrahydropyranyl ether).

"Drug", "drug substance", "active pharmaceutical ingredient", and the like, refer to a compound (e.g., compounds of Formula 1 and compounds specifically named above) that may be used for treating a subject in need of treatment.

"Excipient" refers to any substance that may influence the bioavailability of a drug, but is otherwise pharmacologically inactive.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

The term "subject" as used herein refers to a human or non-human mammal. Examples of non-human mammals include livestock animals such as sheep, horses, cows, pigs, goats, rabbits and deer; and companion animals such as cats, dogs, rodents, and horses.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

As used herein the term "comprising" means "consisting at least in part of". When interpreting each statement in this specification that includes the term "comprising", features other than that or those prefaced by the term may also be present. Related terms such as "comprise" and "comprises" are to be interpreted in the same manner.

The present invention relates to a compound of formula (I):

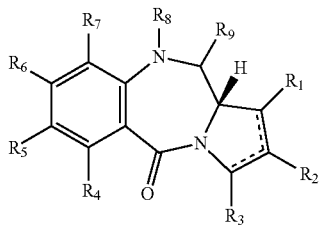

(I)

and salts or solvates thereof.

$R_2$

Suitably $R_2$ is selected from H, R, OH, $NH_2$, NHR, NRR', $CO_2R$, $CH_2$—$CO_2R$, $CO_2H$, $CH_2$—$CO_2H$, $CH_2OH$ and $CH_2OR$.

Suitably $R_2$ is selected from H, $NH_2$, NHR, $CO_2R$, $CH_2$—$CO_2R$, $CO_2H$, $CH_2$—$CO_2H$ and an optionally substituted alkenyl, aryl, heteroaryl, aralkyl or heteroaralkyl group which contains at least one double bond which forms part of a conjugated system with a double bond of the c-ring.

More suitably, $R_2$ is selected from H, $NH_2$, NHR, $CO_2R$, $CH_2$—$CO_2R$, $CO_2H$, $CH_2$—$CO_2H$ and an optionally substituted $C_{3-8}$ heteroaryl and $C_{5-10}$ aryl group.

More suitably $R_2$ is selected from H, $NH_2$, NHR, $CO_2R$, $CH_2$—$CO_2R$, $CO_2H$, $CH_2$—$CO_2H$, and an optionally substituted furanyl, pyrrolyl, thiophenyl, phenyl or napthyl group.

More suitably $R_2$ is selected from H, $NH_2$, $NH(C_{1-6}$ alkyl), $CO_2(C_{1-6}$ alkyl), $CH_2$—$CO_2(C_{1-6}$ alkyl), $CO_2H$ and $CH_2$—$CO_2H$.

$R_3$

Suitably $R_3$ are independently selected from H, $C_{1-12}$ alkyl, $C_{2-12}$ alkenyl, OH, O—$C_{1-12}$ alkyl, $NH_2$, NHR, NRR', $CH_2$—$CO_2C_{1-12}$ alkyl, $CO_2H$, $CH_2$—$CO_2H$, $CO_2C_{1-12}$ alkyl, $COC_{1-12}$ alkyl and CN.

Suitably $R_3$ is selected from H, $C_{1-6}$ alkyl, $C_{2-12}$ alkenyl, OH, O—$C_{1-6}$ alkyl, $NH_2$, $NH(C_{1-6}$ alkyl), $CO_2C_{1-6}$ alkyl, $CH_2$—$CO_2C_{1-6}$ alkyl, $CO_2H$ and $CH_2$—$CO_2H$.

More suitably $R_3$ is selected from H, $NH_2$, $NH(C_{1-6}$ alkyl), $CO_2C_{1-6}$ alkyl, $CH_2$—$CO_2C_{1-6}$ alkyl, $CO_2H$ and $CH_2$—$CO_2H$.

$R_4$

Suitably $R_4$ is selected from H, R, OH, OR, $NH_2$, NHR, NRR', $CO_2H$, $CH_2$—$CO_2H$, $CO_2R$, $CH_2$—$CO_2R$ and halo.

Suitably $R_4$ is selected from H, $C_{1-12}$ alkyl, $C_{3-20}$ heteroaryl, $C_{4-32}$ heteroaralkyl, $C_{5-20}$ aryl groups, $C_{7-32}$ aralkenyl, OH, O—$C_{1-12}$ alkyl, $NH_2$, NHR, $CO_2H$, $CH_2$—$CO_2H$, $CO_2R$, $CH_2$—$CO_2R$ and halo.

More suitably $R_4$ is selected from H, $C_{1-6}$ alkyl, $C_{3-8}$ heteroaryl, $C_{6-12}$ aryl groups, O—$C_{1-6}$ alkyl, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

More suitably $R_4$ is selected from H, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

$R_5$

Suitably $R_5$ is selected from H, R, OH, OR, $NH_2$, NHR, NRR', $CO_2H$, $CH_2$—$CO_2H$, $CO_2R$, $CH_2$—$CO_2R$ and halo.

Suitably $R_5$ is selected from H, $C_{1-12}$ alkyl, OH, O—$C_{1-12}$ alkyl, $OCH_2Ph$, $NH_2$, NHR, NRR', $CO_2H$, $CH_2$—$CO_2H$, $CO_2R$, $CH_2$—$CO_2R$ and halo.

More suitably $R_5$ is selected from H, $C_{1-6}$ alkyl, OH, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

More suitably $R_5$ is selected from H, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

$R_6$

Suitably $R_6$ is selected from H, R, OH, OR, $NH_2$, NHR, NRR', $CO_2H$, $CH_2$—$CO_2H$, $CO_2R$, $CH_2$—$CO_2R$ and halo.

Suitably $R_6$ is selected from H, $C_{1-12}$ alkyl, OH, O—$C_{1-12}$ alkyl, $OCH_2Ph$, $NH_2$, NHR, $CO_2H$, $CH_2$—$CO_2H$, $CO_2R$, $CH_2$—$CO_2R$ and halo.

More suitably $R_6$ is selected from H, $C_{1-6}$ alkyl, OH, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

More suitably $R_6$ is selected from H, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

$R_7$

Suitably $R_7$ is selected from H, R, OH, OR, $NH_2$, NHR, NRR', $CO_2H$, $CH_2$—$CO_2H$, $CO_2R$, $CH_2$—$CO_2R'$ and halo.

Suitably $R_7$ is selected from H, $C_{1-12}$ alkyl, OH, O—$C_{1-12}$ alkyl, $NH_2$, NHR, $CO_2H$, $CH_2$—$CO_2H$, $CO_2R$, $CH_2$—$CO_2R$ and halo.

More suitably $R_7$ is selected from H, $C_{1-6}$ alkyl, O—$C_{1-6}$ alkyl, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

More suitably $R_7$ is selected from H, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl).

Combination of Substituents

Suitably, at least 3 of $R_2$ to $R_7$ are H. Suitably, at least 4 of $R_2$ to $R_7$ are H.

In one aspect, one of $R_2$ to $R_7$ is selected from $NH_2$, $NH(C_{1-6}$ alkyl), $CO_2(C_{1-6}$ alkyl), $CH_2$—$CO_2(C_{1-6}$ alkyl), $CO_2H$ and $CH_2$—$CO_2H$; and the remaining of $R_2$ to $R_7$ are independently selected from H, $C_{1-6}$ alkyl and O—$C_{1-6}$ alkyl.

R and R'

Suitably R and R' are independently selected from optionally substituted $C_{1-8}$ alkyl, $C_{2-8}$ alkenyl, $C_{3-15}$ heterocyclyl, $C_{4-16}$ heterocyclalkyl, $C_{5-17}$ heterocyclalkenyl, $C_{3-10}$ heteroaryl, $C_{4-22}$ heteroaralkyl, $C_{5-23}$ heteroaralkenyl, $C_{5-16}$ aryl groups $C_{6-22}$ aralkyl and $C_{7-22}$ aralkenyl.

Suitably R and R' are independently selected from optionally substituted $C_{1-8}$ alkyl, $C_{2-8}$ alkenyl, $C_{3-12}$ heterocyclyl, $C_{3-10}$ heteroaryl, $C_{4-22}$ heteroaralkyl, $C_{6-14}$ aryl groups and $C_{6-22}$ aralkyl.

More suitably R and R' are independently selected from optionally substituted $C_{1-6}$ alkyl, $C_{2-6}$ alkenyl, $C_{3-11}$ heterocyclyl, $C_{3-8}$ heteroaryl, $C_{4-14}$ heteroaralkyl, $C_{6-12}$ aryl groups and $C_{6-18}$ aralkyl.

$R_1$

In one embodiment, $R_1$ has the formula:

-X-L-X'-D the resulting compound may be represented by the following structure:

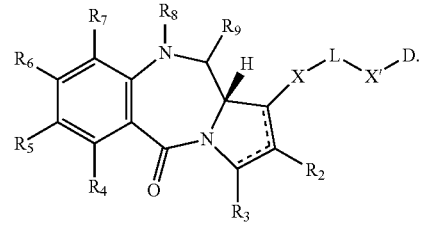

The possible options for the presence or absence of double bonds and for stereoisomers of the above compound are set out below in the structures section and are illustrated by structures (XIII) to (XVI).

X

Suitably X is selected from O, NR", =CR"—, CR"R"'O, C(=O), C(=O)NR", NR"C(=O), O—C(O) and C(O)—O.

Suitably, X is selected from O, =CR"—, C(=O)NR" and NR"C(=O).

More suitably X is selected from O, =CH—, C(=O)NH and NHC(=O).

X'

Suitably X, is selected from O, NR", =CR"—, CR"R"'O, C(=O), C(=O)NR", NR"C(=O), O—C(O) and C(O)—O or is absent.

Suitably X' is selected from O, =CR"—, C(=O)NR" and NR"C(=O).

More suitably X is selected from O, =CH—, C(=O)NH and NHC(=O).

Suitably X is the same as X'.

L

Suitably, any of the peptide chain, alkylene chain, paraformaldehyde chain or polyethylene glycol chain is interrupted by one or more hetero-atoms (e.g., N, O and S) and/or one or more $C_{3-20}$ heteroaryl groups (e.g., pyrrolyl, pyrazolyl, pyrazolyl, 1,2,3-triazolyl, pyridinyl) and/or one or more $C_{5-20}$ aryl groups (e.g. phenyl). More suitably, the chains may be interrupted by from one to three hetero-atoms and/or from one to three $C_{3-20}$ heteroaryl groups and/or from one to three $C_{5-20}$ aryl groups.

Suitably L is selected from a peptide chain having from 2 to 5 amino acids, from 2 to 4 amino acids, from 2 to 3 amino acids; an alkylene chain containing from 3 to 11 carbon atoms, from 3 to 10 carbon atoms, from 3 to 9 carbon atoms, from 3 to 8 carbon atoms, from 3 to 7 carbon atoms, from 3 to 6 carbon atoms, which may contain one or more carbon-carbon double or triple bonds; a paraformaldehyde chain —(OCH$_2$)$_{1-12}$, —(OCH$_2$)$_{1-11}$, —(OCH$_2$)$_{1-10}$, —(OCH$_2$)$_{1-9}$, —(OCH$_2$)$_{1-8}$, —(OCH$_2$)$_{1-7}$, —(OCH$_2$)$_{1-6}$, —(OCH$_2$)$_{1-5}$, —(OCH$_2$)$_{1-4}$, —(OCH$_2$)$_{1-3}$ a polyethylene glycol chain —(OCH$_2$CH$_2$)$_{1-5}$—, chain —(OCH$_2$CH$_2$)$_{1-4}$—, chain —(OCH$_2$CH$_2$)$_{1-3}$—; which chain may be interrupted by one or more hetero-atoms and/or $C_{3-20}$ heteroaryl groups and/or $C_{5-20}$ aryl groups.

More suitably, L may be selected from CH=CH, CH$_2$CH$_2$CH$_2$, CH$_2$CH$_2$CH$_2$CH$_2$ and CH$_2$CH$_2$CH$_2$CH$_2$CH$_2$.

D

Suitably D has the formula (II) or (III) and R$_{11}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

Suitably D has the formula (II) or (III) and R$_{11}$ is selected from N-methylpyrrolylene, furanylene, thiophenylene, N-methylimidazolylene, oxazolylene and thiazolylene.

Suitably D has the formula (II) or (III) and R$_{11}$ is selected from indolylene, N-methylindolylene, benzofuranylene, benzothiophenylene, benzimidazolylene, N-methylbenzoimidazolylene, benzooxazolylene and benzothiazolylene.

Suitably D has the formula (II) or (III) and R$_{12}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

Suitably D has the formula (II) or (III) and R$_{12}$ is selected from N-methylpyrrolylene, furanylene, thiophenylene, N-methylimidazolylene, oxazolylene and thiazolylene.

Suitably D has the formula (II) or (III) and R$_{12}$ is selected from indolylene, N-methylindolylene, benzofuranylene, benzothiophenylene, benzimidazolylene, N-methylbenzoimidazolylene, benzooxazolylene and benzothiazolylene.

Suitably D is selected from formula (IV):

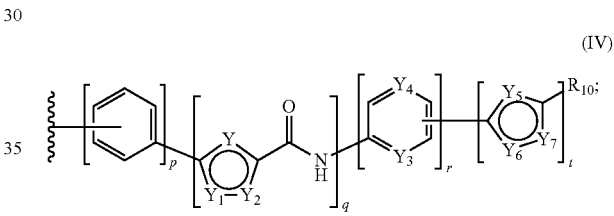

formula (V):

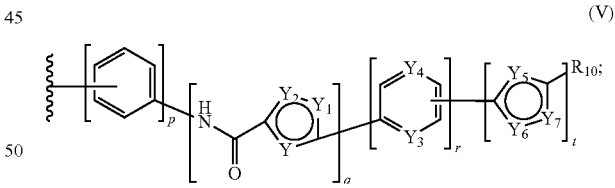

formula (VI):

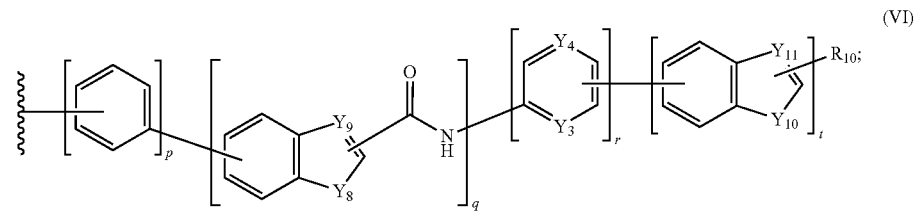

formula (VII):

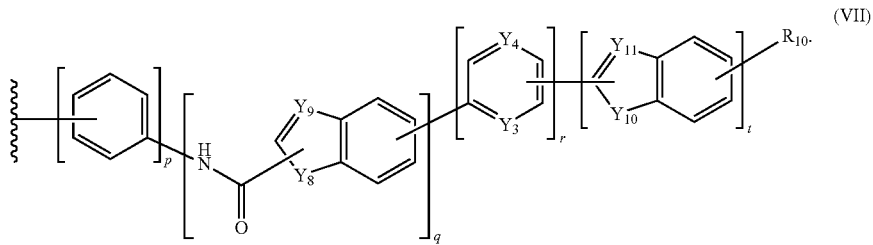

wherein:
- p is 0 or 1;
- q is 1, 2, 3, 4, 5 or 6;
- r is 0 or 1;
- t is 0 or 1
- Y, $Y_1$ and $Y_2$ are selected from CH, CH and N—$CH_3$; CH, N—$CH_3$ and CH; N, CH and N—$CH_3$; N, N—$CH_3$ and CH; CH, S and CH; CH, CH and S; N, S and CH; N, CH and S; N, O and CH; N, CH and O; CH, CH and O; CH O and CH; COH, N—$CH_3$ and CH; and COH, CH and N—$CH_3$;
- $Y_3$ is N or CH;
- $Y_4$ is N or CH; wherein at least one of $Y_3$ and $Y_4$ is CH;
- $Y_5$, $Y_6$ and $Y_7$ are selected from CH, CH and N—$CH_3$; CH, N—$CH_3$ and CH; N, CH and N—$CH_3$; N, N—$CH_3$ and CH; CH, S and CH; CH, CH and S; N, S and CH; N, CH and S; N, O and CH; N, CH and O; CH, CH and O; CH O and CH; COH, N—$CH_3$ and CH; and COH, CH and N—$CH_3$;
- $Y_8$ and $Y_9$ are selected from NH and CH; NH and N; N—$CH_3$ and CH; N—$CH_3$ and N; O and CH; O and N; S and CH; and S and N;
- $Y_{10}$ and $Y_{11}$ are selected from NH and CH; NH and N; N—$CH_3$ and CH; N—$CH_3$ and N; O and CH; O and N; S and CH; and S and N;
- $R_{10}$ is H, Z—R″, Z—$CO_2$R″, Z—C(=O)—NH—$(CH_2)_{1-6}$—NR″R‴, and Z—C(=O)—NH—$(CH_2)_{1-6}$—C(=NH)NR″R‴;
- Z is absent or is selected from $C_{3-20}$ heteroaryl, $C_{1-6}$ alkyl substituted $C_{3-20}$ heteroaryl, —$(CH_2)_n$—$C_{3-20}$ heterocyclyl, and O—$(CH_2)_n$—$C_{3-20}$ heterocyclyl group; and
- n is 0, 1, 2, 3 or 4.

Hence, the heteroaryl rings containing Y, $Y_1$ and $Y_2$ and $Y_5$, $Y_6$ and $Y_7$ are independently selected from one of the following groups:

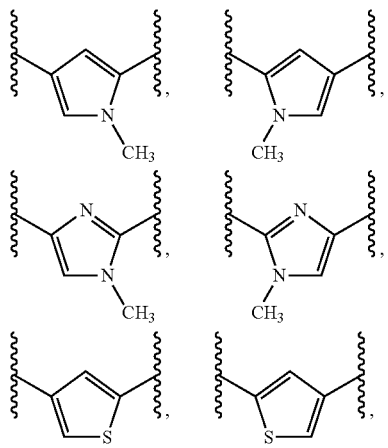

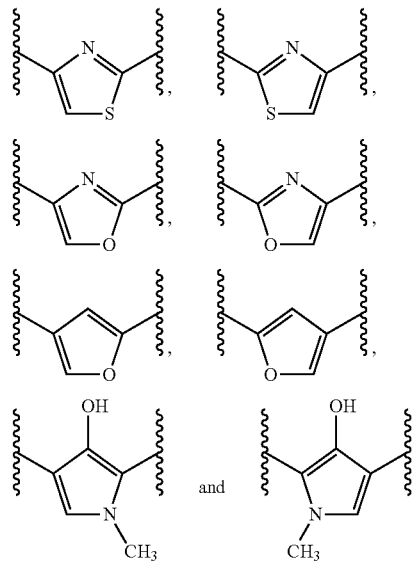

Hence, the heteroaryl rings containing $Y_8$ and $Y_9$, $Y_{10}$ and $Y_{11}$ are independently selected from one of the following groups:

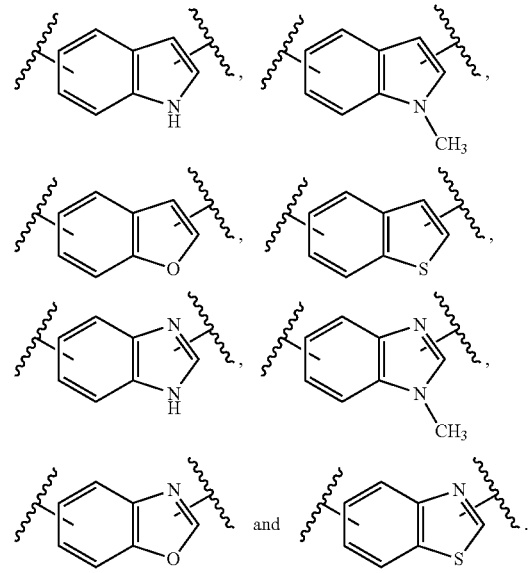

Suitably heteroaryl groups containing the $Y_8$ and $Y_9$ groups and those containing $Y_{10}$ and $Y_{11}$ groups are attached to the rest of the compound at the C-2 and C-5 positions as shown below:

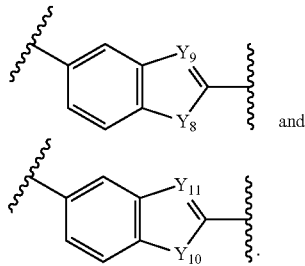

The aromatic ring containing $Y_3$ and $Y_4$ is a phenylene or pyridinylene group.

Suitably D is of formula (IV) or (V) and p is 0, such that D may be represented by formula (VIII) or (IX):

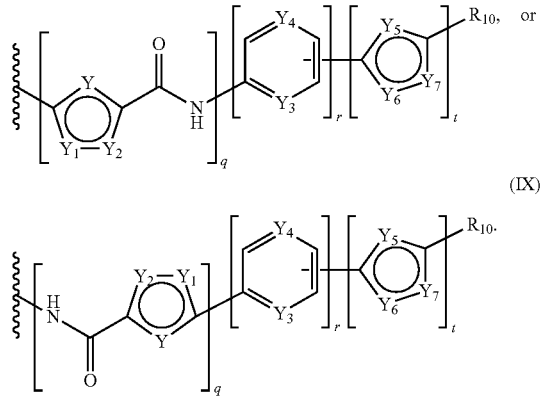

Suitably Y, $Y_1$ and $Y_2$ are selected from CH, CH and N—$CH_3$; CH, N—$CH_3$ and CH; N, CH and N—$CH_3$; N, N—$CH_3$ and CH. Suitably Y, $Y_1$ and $Y_2$ is N, N—$CH_3$ and CH.

Suitably r is 1 and $Y_3$ and $Y_4$ are CH.

Suitably $Y_5$, $Y_6$ and $Y_7$ are selected from CH, CH and N—$CH_3$; CH, N—$CH_3$ and CH; N, CH and N—$CH_3$; N, N—$CH_3$ and CH. Suitably $Y_5$, $Y_6$ and $Y_7$ is CH, N—$CH_3$ and CH.

Suitably, $R_{10}$ is H, Z—R" and Z—$CO_2$R". Suitably, $R_{10}$ is H, Z—H, Z—$C_{1-6}$ alkyl, Z—$CO_2$H and Z—$CO_2C_{1-6}$ alkyl.

Suitably, Z is selected from $C_{3-20}$ heteroaryl and $C_{1-6}$ alkyl substituted $C_{3-20}$ heteroaryl;

suitably, Z is selected from $C_{3-10}$ heteroaryl and $C_{1-6}$ alkyl substituted $C_{3-10}$ heteroaryl;

suitably, Z is selected from $C_{3-8}$ heteroaryl and $C_{1-6}$ alkyl substituted $C_{3-8}$ heteroaryl.

More suitably, Z is a $C_8$ heteroaryl or a methyl substituted $C_8$ heteroaryl selected from benzofuranyl, benzothiophenyl, indolyl and N-methyl indolyl.

More suitably Z is absent and $R_{10}$ is $CO_2$R".

More suitably Z is absent and $R_{10}$ is $CO_2C_{1-6}$ alkyl.

More suitably D is formula (X):

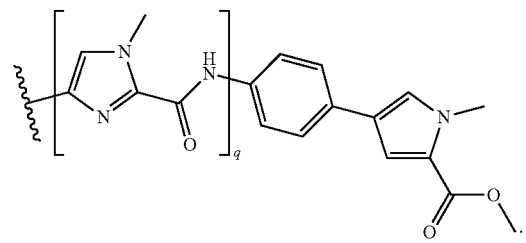

Suitably D is of formula (VI) or (VII) and p is 0, such that D may be represented by formula (XI) or (XII):

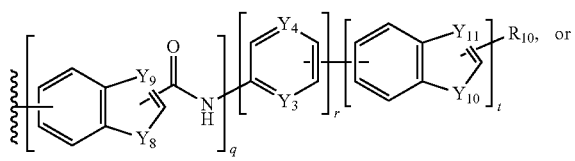

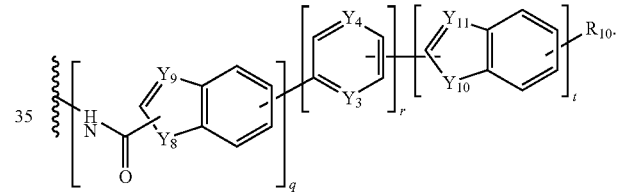

Suitably $Y_8$ and $Y_9$ are selected from NH and CH; NH and N; N—$CH_3$ and CH; N—$CH_3$ and N; O and CH; O and N. Suitably $Y_8$ and $Y_9$ are N—$CH_3$ and CH.

$Y_{10}$ and $Y_{11}$ are selected from NH and CH; NH and N; N—$CH_3$ and CH; N—$CH_3$ and N; O and CH; and O and N. Suitably $Y_{10}$ and $Y_{11}$ are N—$CH_3$ and CH.

Suitably r is 1 and $Y_3$ and $Y_4$ are CH.

Suitably, $R_{10}$ is H, Z—R" and Z—$CO_2$R".

Suitably, $R_{10}$ is H, Z—H, Z—$C_{1-6}$ alkyl, Z—$CO_2$H and Z—$CO_2C_{1-6}$ alkyl.

Suitably, Z is selected from $C_{3-20}$ heteroaryl and $C_{1-6}$ alkyl substituted $C_{3-20}$ heteroaryl;

suitably, Z is selected from $C_{3-10}$ heteroaryl and $C_{1-6}$ alkyl substituted $C_{3-10}$ heteroaryl; suitably, Z is selected from $C_{3-8}$ heteroaryl and $C_{1-6}$ alkyl substituted $C_{3-8}$ heteroaryl.

More suitably, Z is a $C_8$ heteroaryl or a methyl substituted $C_8$ heteroaryl selected from benzofuranyl, benzothiophenyl, indolyl and N-methyl indolyl.

More suitably Z is absent and $R_{10}$ is $CO_2$R".

More suitably Z is absent and $R_{10}$ is $CO_2C_{1-6}$ alkyl.

Structures

In some aspects, the compound of formula (I) has no double bonds in the C-ring and may be represented by the following structures (XIII):

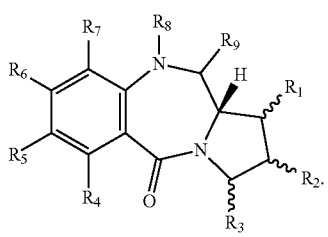
(XIII)

Suitably, the compound of formula (XIII) may be prepared with controlled stereochemistry and may be selected from:

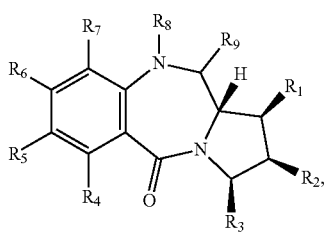
(XIIIa)

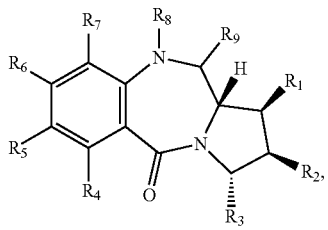
(XIIIb)

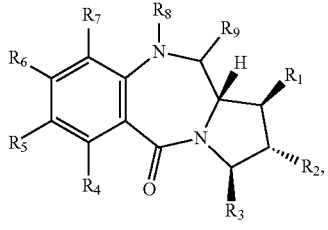
(XIIIc)

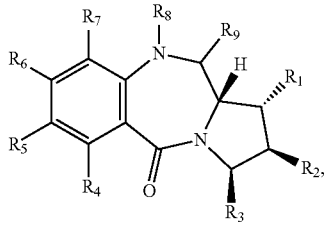
(XIIId)

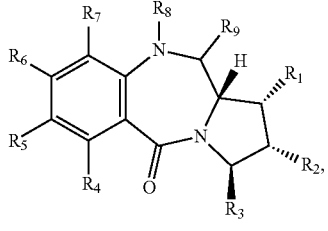
(XIIIe)

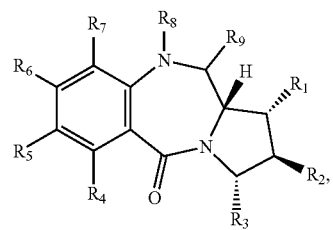
(XIIIf)

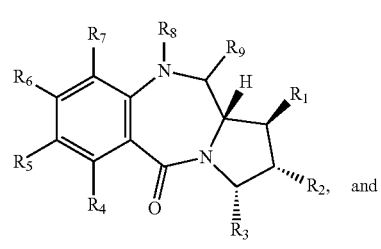
(XIIIg) and

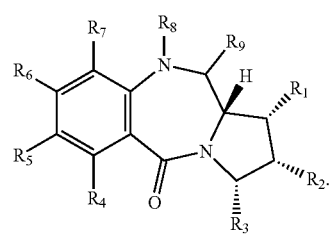
(XIIIh)

In some aspects, the compound of formula (I) has a double bond between C1 and C2 and may be represented by the following structure (XIV):

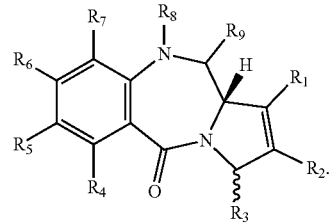
(XIV)

Suitably, the compound of formula (XIV) may be prepared with controlled stereochemistry and may be selected from:

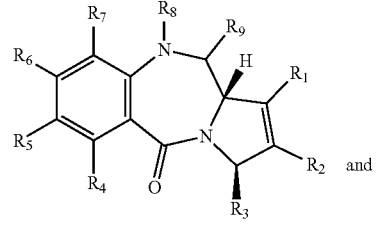
(XIVa) and

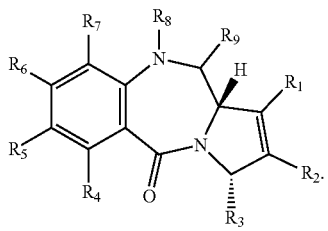

(XIVb)

In some aspects, the compound of formula (I) has a double bond between C2 and C3 and may be represented by the following structure (XV):

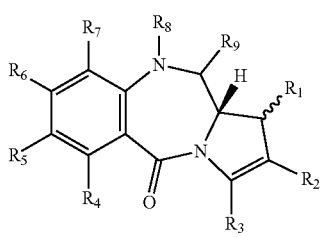

(XV)

Suitably, the compound of formula (XV) may be prepared with controlled stereochemistry and may be selected from:

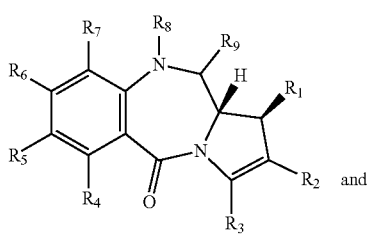

(XVa) and

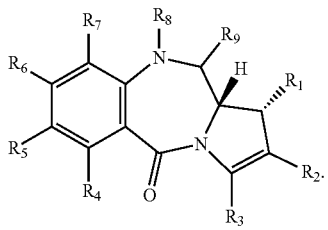

(XVb)

In some aspects, the compound of formula (I) has $R_3=R_4=R_7=H$ and may be represented by the following structure (XVI):

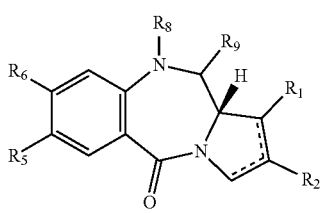

(XVI)

Monomeric Compounds

Suitably the compound of formula (I) is:

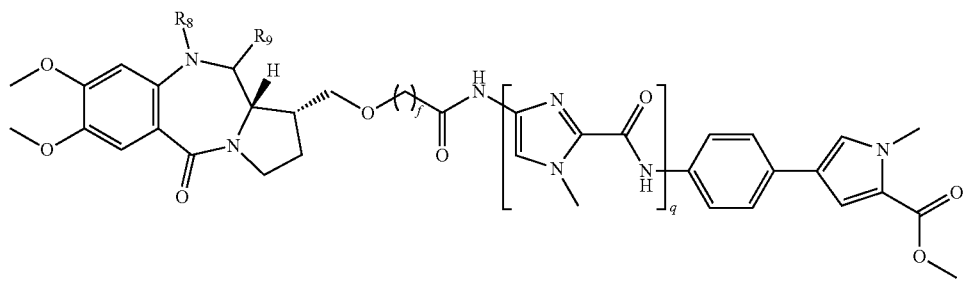

wherein f is selected from 1, 2, 3, 4, 5, 6, 7, 8, 9 and 10; and q is selected from 1, 2, 3, 4, 5 and 6.

Suitably the compound of formula (I) is:

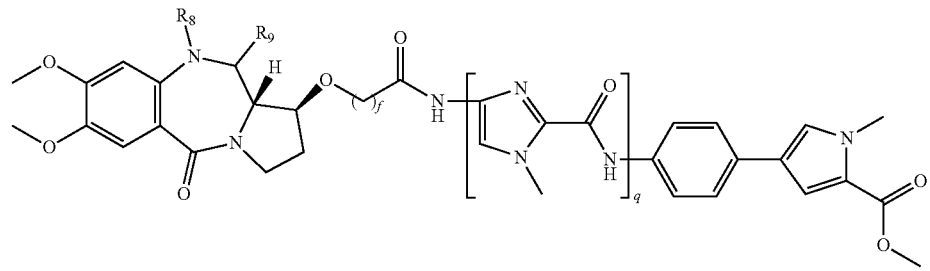

wherein f is selected from 1, 2, 3, 4, 5, 6, 7, 8, 9 and 10; and q is selected from 1, 2, 3, 4, 5 and 6.

Dimer

In another embodiment the compound is a dimer where R, of the first monomer and R'$_6$ of the second monomer form together a bridge having the formula -X-L-X'-linking the monomers, the resulting dimer may be represented by the structure (XVII):

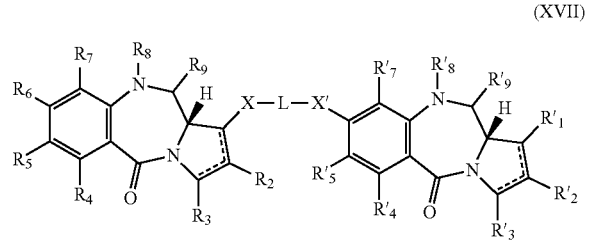

(XVII)

wherein X', R'$_2$, R'$_3$, R'$_4$, R'$_5$, R'$_7$, R'$_8$ and R'$_9$ are independently selected from groups with the same meanings as for X, R$_2$, R$_3$, R$_4$, R$_5$, R$_7$, R$_8$ and R$_9$ respectively, and L is as described above, and R'$_1$ of the second monomer is selected from H, R, OH, OR, NH$_2$, NHR, NRR', CH$_2$—OR, =O, =CH—R, =CH$_2$, CH$_2$—CO$_2$R, CH$_2$—CO$_2$H, CH$_2$—SO$_2$R, O—SO$_2$R, CO$_2$H, CO$_2$R, COR, CN, (C$_{1-12}$ alkylene)-C(O)NR'',R''' and (C$_{2-12}$ alkenylene)-C(O)NR'R'' and halo.

Suitably R'1 of the second monomer is selected from H, R, OR, NH$_2$, NHR, NRR', =CH—R, =CH$_2$, (C$_{1-12}$ alkylene)-C(O)NR'',R''' and (C$_{2-12}$ alkenylene)-C(O)NR'R'' and halo.

Suitably R'1 of the second monomer is selected from H, C$_{1-12}$ alkyl, O—C$_{1-12}$ alkyl, OCH$_2$Ph, NH$_2$, NHR, NRR', =CH—C$_{1-12}$ alkyl, =CH$_2$, CH$_2$—CO$_2$R, CH$_2$—CO$_2$H, CO$_2$H, CO$_2$R, (C$_{1-12}$ alkylene)-C(O)NR'',R''' and (C$_{2-12}$ alkenylene)-C(O)NR'R'' and halo.

Suitably, the compound of formula (XVII) may be prepared with no double bond between C1 and C2 and with controlled stereochemistry for the bridge and may be selected from:

(XVIIa)

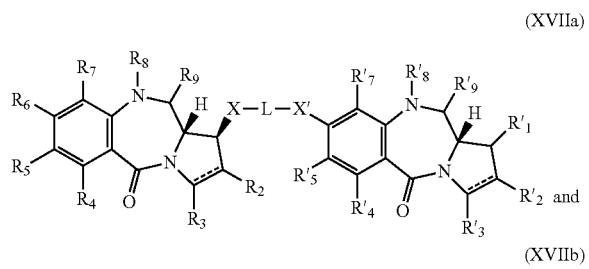

and (XVIIb)

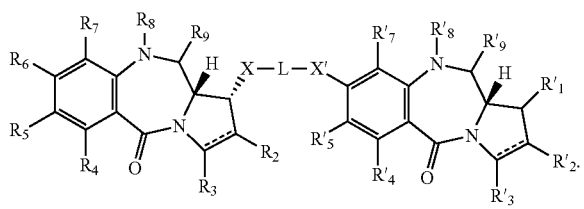

The possible options for the presence or absence of double bonds in the C-ring and for stereoisomers of each monomer that make up the dimers (XVII) to (XVIIb) are set out above in formulas (XIII) to (XVb) in the suitable structures section.

In another embodiment the compound is a dimer where R$_6$ of the first monomer and R'$_1$, of the second monomer form together a bridge having the formula -X-L-X'-linking the monomers, the resulting dimer may be represented by the structure (XVIII):

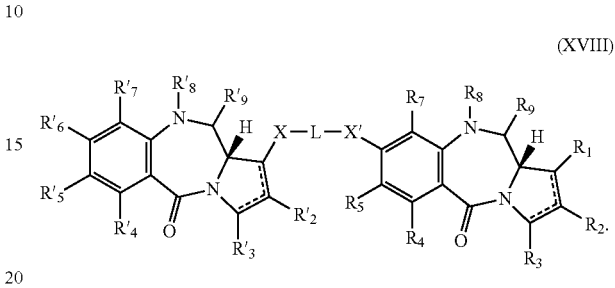

(XVIII)

wherein X', R'$_2$, R'$_3$, R'$_4$, R'$_5$, R'$_7$, R'$_8$ and R'$_9$ are independently selected from groups with the same meanings as for X, R$_2$, R$_3$, R$_4$, R$_5$, R$_7$, R$_8$ and R$_9$ respectively, and L is as described above, and R'$_6$ of the second monomer is selected from H, R, OH, OR, SH, SR, NH$_2$, NHR, NRR', CO$_2$H, CH$_2$—CO$_2$H, CO$_2$R, CH$_2$—CO$_2$R, NO$_2$, Me$_3$Sn and halo.

Suitably R'$_6$ of the second monomer is selected from H, R, OH, OR, NH$_2$, NHR, NRR', CO$_2$H, CH$_2$—CO$_2$H, CO$_2$R, CH$_2$—CO$_2$R and halo.

Suitably, the compound of formula (XVIII) may be prepared with no double bond between C1 and C2 and with controlled stereochemistry for the bridge and may be selected from:

(XVIIIa)

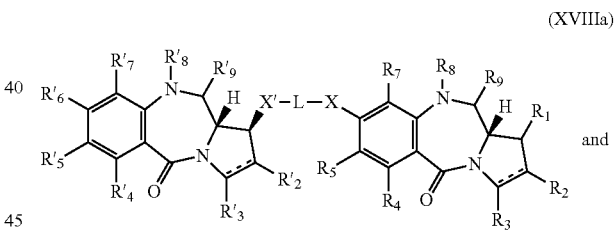

and (XVIIIb)

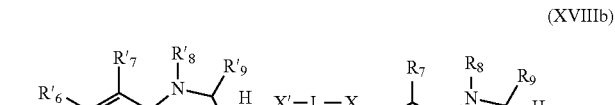

The possible options for the presence or absence of double bonds in the C-ring and for stereoisomers of each monomer that make up the dimers (XVIII) to (XVIIIb) are set out above in formulas (XIII) to (XVb) in the suitable structures section.

In a further embodiment the compound is a dimer with each monomer being the same or different and being of formula (I) where R, of the first monomer and R', of the second monomer form together a bridge having the formula -X-L-X'-linking the monomers, the resulting dimer may be represented by the following structure (XIX:

(XIX)

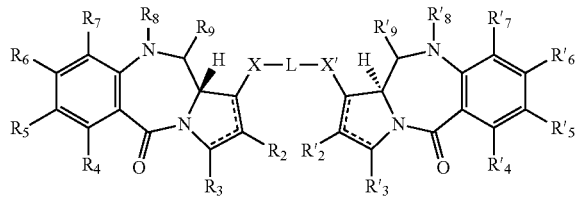

wherein X', R'$_2$, R'$_3$, R'$_4$, R'$_5$, R'$_6$, R'$_7$, R'$_8$ and R'$_9$ are independently selected from groups with the same meanings as for X, R$_2$, R$_3$, R$_4$, R$_5$, R$_6$, R$_7$, R$_8$ and R$_9$ respectively, and L is as described above.

Suitably, the compound of formula (XIX) may be prepared with no double bond between C1 and C2 and with controlled stereochemistry for the bridge and may be selected from:

(XIXa)

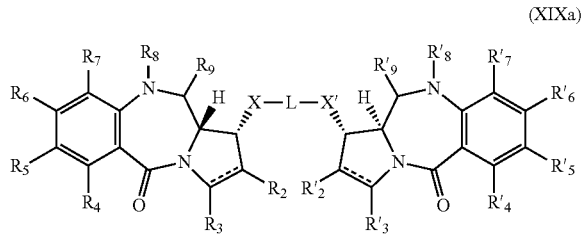

(XIXb)

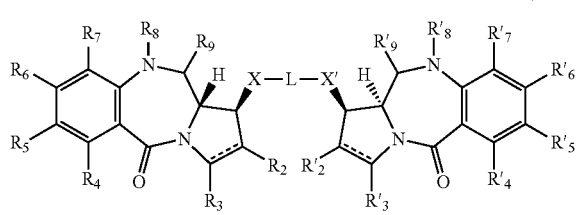

(XIXc)

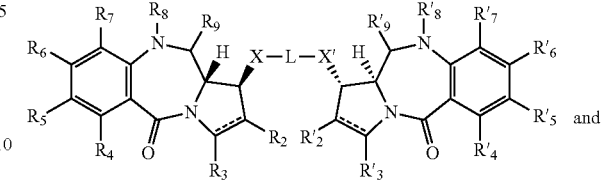

and (XIXd)

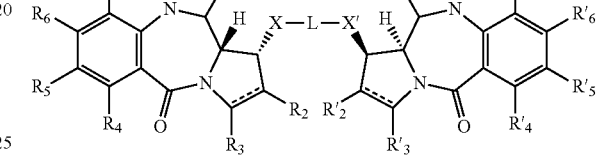

The possible options for the presence or absence of double bonds in the C-ring and for stereoisomers of each monomer that make up the dimers (XIX) to (XIXd) are set out above in formulas (XIII) to (XVb) in the suitable structures section.

Suitably the compound of formula (I) is a dimer with each monomer being the same and being of formula (I) where the R, groups of the monomers form together a bridge having the formula -X-L-X'-linking the monomers.

Suitably, the dimer has the structure:

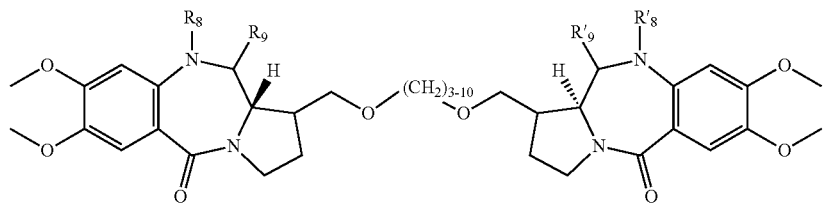

More suitably, the dimer has the structure:

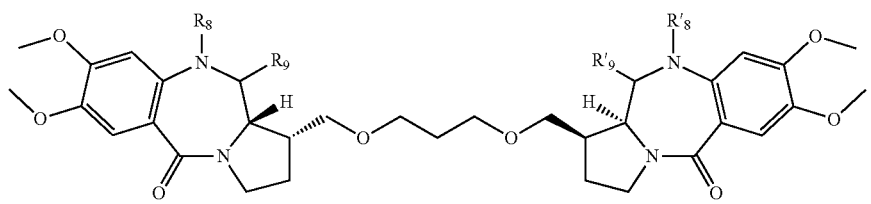

and either:
  (i) $R_8$ and $R_9$ together form a double bond;
  (ii) $R_8$ is H and $R_9$ is OH; or
  (iii) $R_8$ is H and $R_9$ is $OR^A$ and $R^A$ is $C_{1-6}$ alkyl.

Applications

The invention finds application in the treatment of proliferative diseases.

The term "proliferative disease" refers to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, hepatocellular cancer, gastric or stomach cancer including gastrointestinal cancer, bowel cancer, colon cancer, hepatoma, breast cancer, glioblastoma, cervical cancer, ovarian cancer, prostate cancer, testicular cancer, liver cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Cancers of particular interest include, but are not limited to, breast cancer (both ER positive and ER negative), pancreatic cancer, lung cancer and leukaemia.

A skilled person is readily able to determine whether or not a candidate compound treats a proliferative condition for any particular cell type.

Suitably subjects are human, livestock animals and companion animals.

Administration & Dose

Compounds of formula I may be administered alone or in combination with one or another or with one or more pharmacologically active compounds which are different from the compounds of formula I.

Compounds of the invention may suitably be combined with various components to produce compositions of the invention. Suitably the compositions are combined with a pharmaceutically acceptable carrier or diluent to produce a pharmaceutical composition (which may be for human or animal use). Suitable carriers and diluents include isotonic saline solutions, for example phosphate-buffered saline. Useful pharmaceutical compositions and methods for their preparation may be found in standard pharmaceutical texts. See, for example, *Handbook for Pharmaceutical Additives*, 3rd Edition (eds. M. Ash and I. Ash), 2007 (Synapse Information Resources, Inc., Endicott, N.Y., USA) and *Remington: The Science and Practice of Pharmacy*, 21st Edition (ed. D. B. Troy) 2006 (Lippincott, Williams and Wilkins, Philadelphia, USA) which are incorporated herein by reference.

The compounds of the invention may be administered by any suitable route. Suitably the compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form.

The compounds of the invention, their pharmaceutically acceptable salts, and pharmaceutically acceptable solvates of either entity can be administered alone but will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intravenously, intra-arterially, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Suitably formulation of the invention is optimised for the route of administration e.g. oral, intravenously, etc.

Administration may be in one dose, continuously or intermittently (e.g. in divided doses at appropriate intervals) during the course of treatment. Methods of determining the most effective means and dosage are well known to a skilled person and will vary with the formulation used for therapy, the purpose of the therapy, the target cell(s) being treated, and the subject being treated. Single or multiple administrations can be carried out with the dose level and the dose regimen being selected by the treating physician, veterinarian, or clinician.

Depending upon the disorder and patient to be treated, as well as the route of administration, the compositions may be administered at varying doses. For example, a typical dosage for an adult human may be 100 ng to 25 mg (suitably about 1 micro g to about 10 mg) per kg body weight of the subject per day.

Suitably guidance may be taken from studies in test animals when estimating an initial dose for human subjects. For example when a particular dose is identified for mice, suitably an initial test dose for humans may be approx. 0.5× to 2× the mg/Kg value given to mice.

Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH.

A reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

Compounds of Formula 1, which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —NH₂ may be —NH₃⁺), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO⁻), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium ($Na^+$) potassium ($K^+$), magnesium ($Mg^{2+}$), calcium ($Ca^{2+}$), zinc ($Zn^{2+}$), and aluminum ($Al^{3+}$). Examples of suitable organic cations include, but are not limited to, ammonium ion (i.e. $NH4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011).

Pharmaceutically acceptable salts may be prepared using various methods. For example, one may react a compound of Formula 1 with an appropriate acid or base to give the desired salt. One may also react a precursor of the compound of Formula 1 with an acid or base to remove an acid- or base-labile protecting group or to open a lactone or lactam group of the precursor. Additionally, one may convert a salt of the compound of Formula 1 to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of formula I include imine, carbinolamine and carbinolamine ether forms of the PBD. The carbinolamine or the carbinolamine ether is formed when a nucleophilic solvent ($H_2O$, ROH) adds across the imine bond of the PBD moiety. The balance of these equilibria between these forms depend on the conditions in which the compounds are found, as well as the nature of the moiety itself.

These compounds may be isolated in solid form, for example, by lyophilisation.

Further particular and preferred aspects are set out in the accompanying independent and dependent claims. Features of the dependent claims may be combined with features of the independent claims as appropriate, and in combinations other than those explicitly set out in the claims.

Synthetic Strategies

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations, A Guide to Functional Group Preparations*, 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry,* 4th Edition, (2006) and P. Kocienski, *Protective Groups,* 3rd Edition (2005).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., $-78°$ C. to $0°$ C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

Preferred General Synthetic Strategies

A wide range of synthetic strategies are known in the art to prepare PBD compounds (1, 21).

Synthetic Strategies Involving Reduction of a Dilactam

Several of these synthetic strategies for preparing PBD compounds are based on forming a key PBD dilactam that can then undergo a reduction reaction to provide the desired PBD compound.

Route A

A 2-nitrobenzoic acid derivative [A1] may be condensed with a pyrrolidine 2-carboxylic ester [A2] building block to produce an amide compound [A3]. The nitro group of [A3] may be reduced to a nucleophilic anilinic amine [A4] which may then react with an electrophilic substituent from the pyrolidine ring to produce the B-ring of the PBD dilactam [A5] by a 7-exotrig ring closure. Catalytic hydrogenation in the presence of palladium on charcoal may be used to carry out the reduction (WO 2004/043963) followed by acid catalysed cyclisation (39), with e.g. HCl, to produce the key PBD dilactam [A5]. Other reagents and conditions may be used for carrying out the reduction (37-40). $R_1$-$R_7$ below represent the desired final substituents, or the precursors or protected forms thereof.

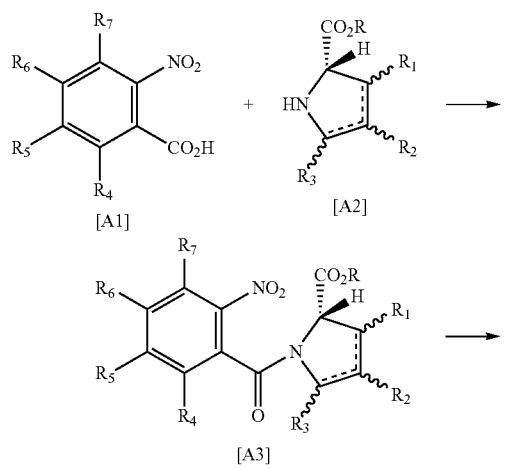

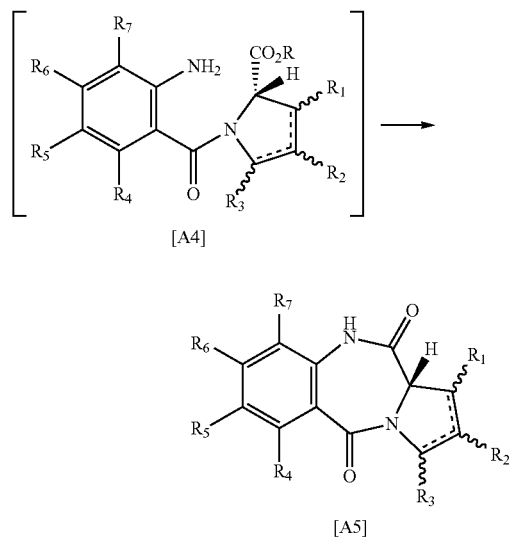

The amide group of the PBD dilactam [A5] formed in the cyclisation step may be reduced to provide the desired PBD compound [A6] using covalent hydrides, such as LiAlH$_4$ or NaBH$_4$ (21, 41). The desired PBD compound [A6] is shown below as an imine but, as discussed above, the imine may also exist as a carbinolamine [NH—CH(OH)], or as a carbinolamine alkyl ether. The efficiency of the regioselective reduction of the carbonyl is affected by factors such as A-ring substitution pattern, nitrogen-protecting groups, the C-ring substitution pattern and the source of the hydride. In addition, protection of the nitrogen with an appropriate nitrogen protecting group may assist the dilactam reduction. A protecting group may be added by treating the dilactam [A5] with a kinetic base (e.g. NaH), followed by addition of an electrophile (e.g. CH$_3$—O—CH$_2$—Cl [MOM-Cl] as shown below) which does not affect the S-stereochemistry of the pyrrolidine (41).

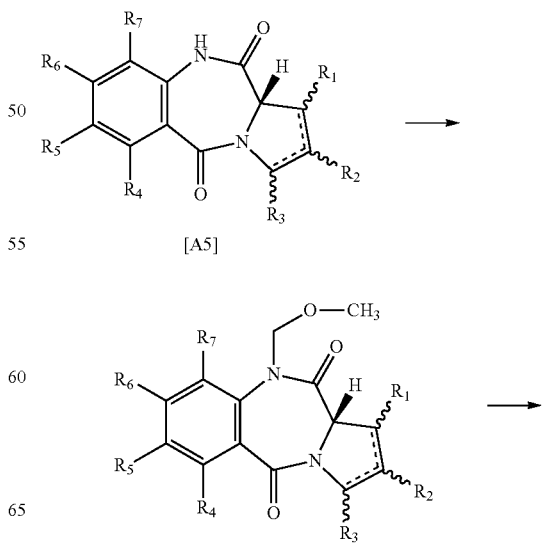

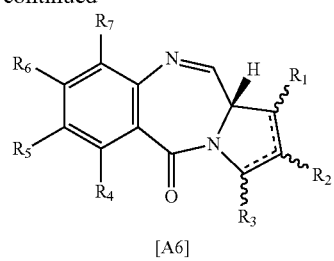
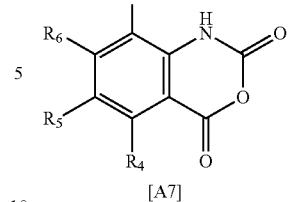
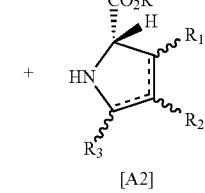

Route B

The PBD dilactam [A5] may also be produced by a reductive cyclization of N-(azidobenzoyl)pyrrolidine-2 carboxylate ester [A24]. The azide compound [A24] may be prepared by reacting the corresponding nitro compound with sodium azide, $NaN_3$ (42). The azide reduction may be carried out using silicon-based reagents, e.g. hexamethyldisilathiane [HMDST] (42-44), ferrous sulphate (45) or ferric chloride with sodium iodide (46).

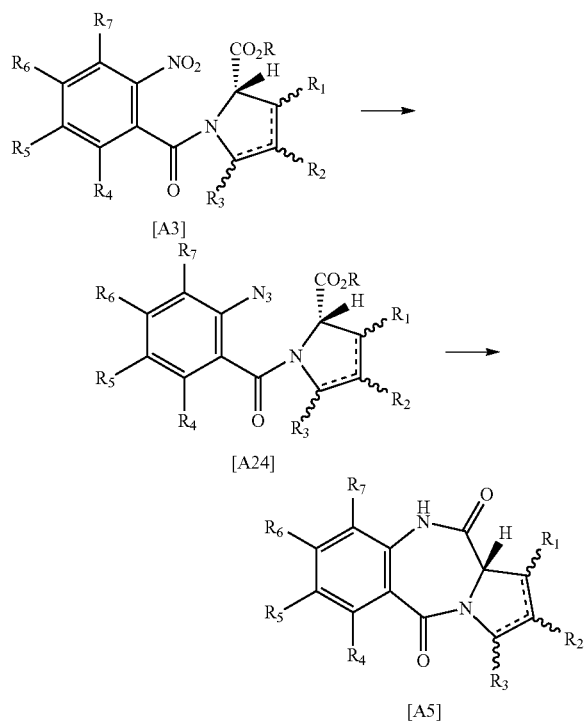

The dilactam [A5] may be reduced to the desired PBD compound [A6] as in Route A above.

Route D

The dilactam [A11] may be prepared using a hypovalent iodine reagent phenyliodine (III) bis(trifluoroacetate) PIFA to cyclize the B-ring (50). Standard peptide coupling conditions may be used to attach a proline derivative [A2], where R is methyl, to a benzoyl derivative [A7]. Saponification with LiOH and amide coupling with methoxamine give the N-alkoxyamide [A9]. Treatment of [A9] with PIFA produce an N-acylnitrenium species [A10] which undergoes an intramolecular electrophilic aromatic substitution to provide the dilactam [A11], where $R_8$ is $OCH_3$. The $R_8$ methoxy group can be removed from dilactam [A11] by treatment with molybdenum hexacarbonyl to give the dilactam [A5], where $R_8$ is H, which may then be reduced to the desired PBD compound [A6] as in Route A above.

In contrast to the nitro reduction strategy (Route A), the azide reductive cyclization has the advantage that it occurs without the need for a second acid-catalysed step. The dilactam [A5] formed by the azide reductive cyclization can then be reduced to the desired PBD compound [A6] as discussed in relation to Route A above.

Route C

An isatoic anhydride [A7] may be condensed with a proline derivative [A2], where R is H, to produce a PBD dilactam [A5] (41, 47, 48). Isatoic anhydrides are commercially available but may also be prepared from the corresponding anthranilic acid derivative and triphosgene as disclosed in U.S. Pat. No. 6,660,856.

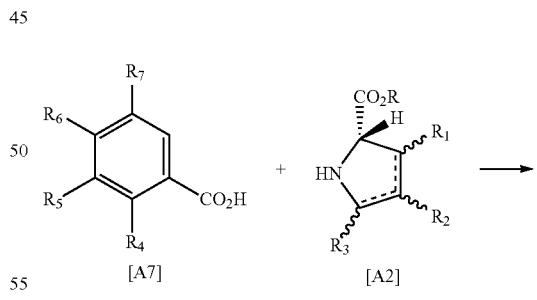
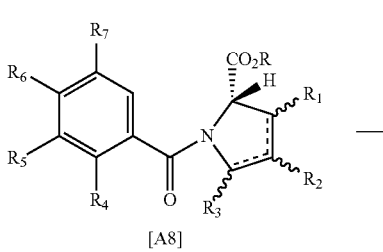

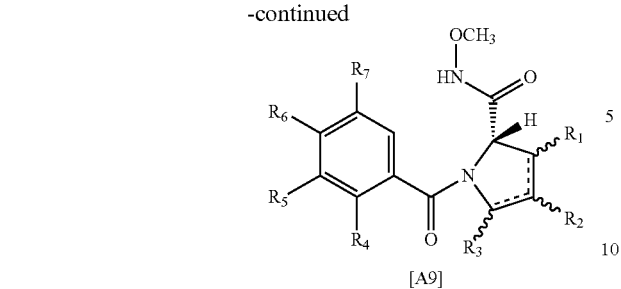

[A9]

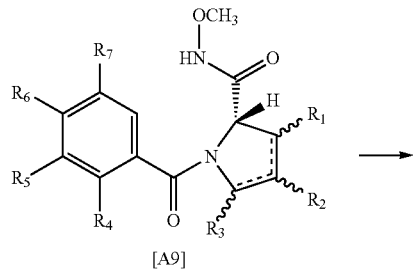

[A9]

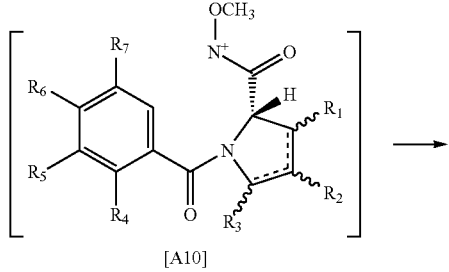

[A10]

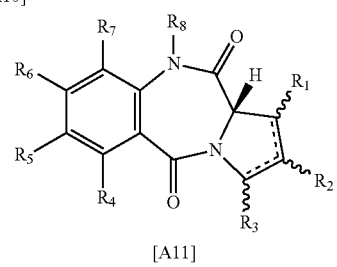

[A11]

The nucleophilic character of the phenyl ring is critical to the cyclization and electron-donating groups, such as alkoxy groups e.g. $CH_3O—$, at $R_5$ and $R_6$ are important to provide the required nucleophilic character.

Route E

Intramolecular cyclization of an aryl triflate [A12] using an external $NH_3$-based reagent, such as ammonium hydroxide and ammonium chloride, that displaces the aryl triflate may be used to form the dilactam [A5] (51). However, some racemization can occur at the carbon that forms part of both the B- and C-rings.

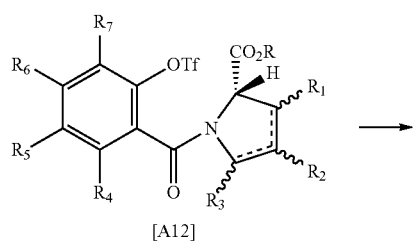

[A12]

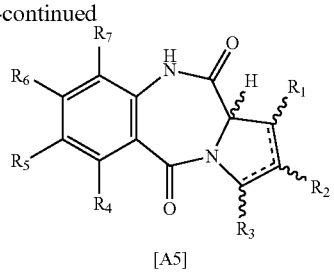

[A5]

The dilactam [A5] may be reduced to the desired PBD compound [A6] as in Route A above.

Synthetic Strategies Involving Cyclization of PBD Precursor

These synthetic strategies form the B-ring by cyclization using an aldehyde, a protected aldehyde (e.g. acetal or thioacetal) or a hydroxyl group (which can be oxidised to the aldehyde) as an electrophilic group in the PBD precursor.

Route G

Route G involves reduction of a nitro group on the A-ring of the precursor [A13] to give the amine [A14] which then undergoes a cyclization with the aldehyde group to form the B-ring. The reductive cyclization may be carried out using catalytic hydrogenation with palladium on charcoal (52, 53) or with Raney-nickel (54, 55), although other reductive cyclization conditions are known (56, WO2007/085930).

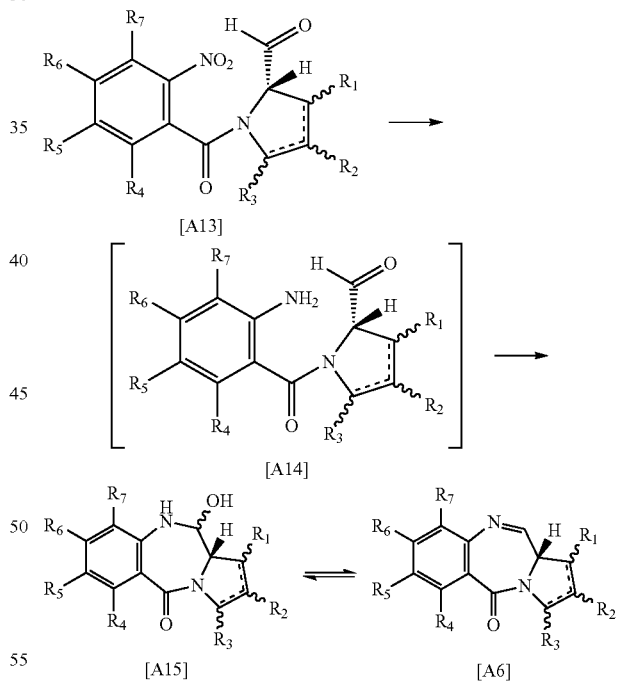

The precursor [A13] may be prepared by condensing a 2-nitrobenzoic acid derivative [A1], see above, with a pyrrolidine derivative. The pyrrolidine derivative may contain an aldehyde precursor, such as alcohol —CHOH, at the pre-C11 position. In which case the alcohol is oxidized to the aldehyde, e.g. by means of TPAP or DMSO (Swern oxidation), to form the precursor [A13].

Route H

One of the most widely used strategies to form PBD compounds is to use a thioacetal as a protected aldehyde.

Protection of the aldehyde can be carried out after A- to C-ring coupling, or alternatively a C-ring carrying a thioacetal may be coupled to the A-ring.

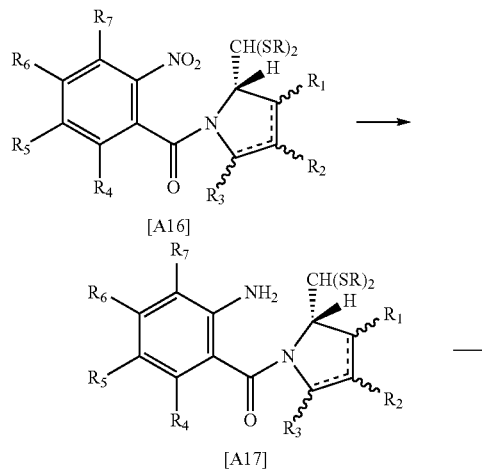

[A16]

[A17]

The amine [A17] may be prepared by reduction of the nitro group of [A16], subsequent removal of the thioacetal and cyclization provides the desired PBD compound [A6]. Mercury (II) chloride may be used as the reagent for removing the thioacetal and effecting cyclization (57), although other reagents may also be used (58, 59).

Generally, the thioacetal group —CH(SR)$_2$ has C1-C7 alkyl groups, such as methyl or ethyl, as the R groups and suitable thioacetal protected C-rings may be prepared via a literature method (60).

The thioacetal protecting group is robust and a wide variety of reactions may be carried out on the nitro thioacetal scaffold [A16]. This strategy has been used to make both monomeric PBD conjugates, such as those involving polypyrrole moieties (61), and dimeric PBD species (33, 62, 63).

Route I

Acetals [A18] where R is a C1-C7 alkyl group, such as methyl or ethyl, may be used as a protected aldehyde and, following deprotection under mild acidic conditions, may be cyclized to form the B-ring of PBDs [A6] (21).

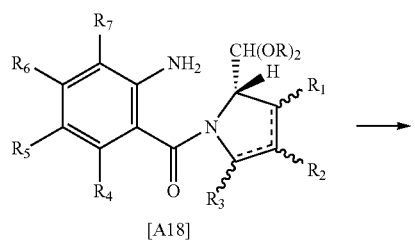

[A18]

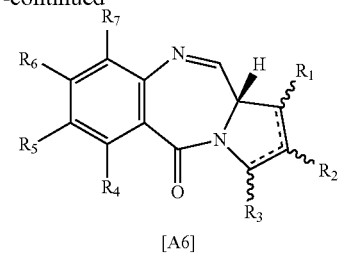

[A6]

Zinc chloride and chlorotrimethylsilane may provide a stereoselective cyclization (64, 65).

Route J

The PBD [A6] may be prepared by consecutive Staudinger/intramolecular aza-Wittig reactions of N-(2-azidobenzoyl)-pyrrolidine-2-carboxaldehyde derivatives [A19] that proceed via an iminophosphorane intermediate [A20] (66, 67).

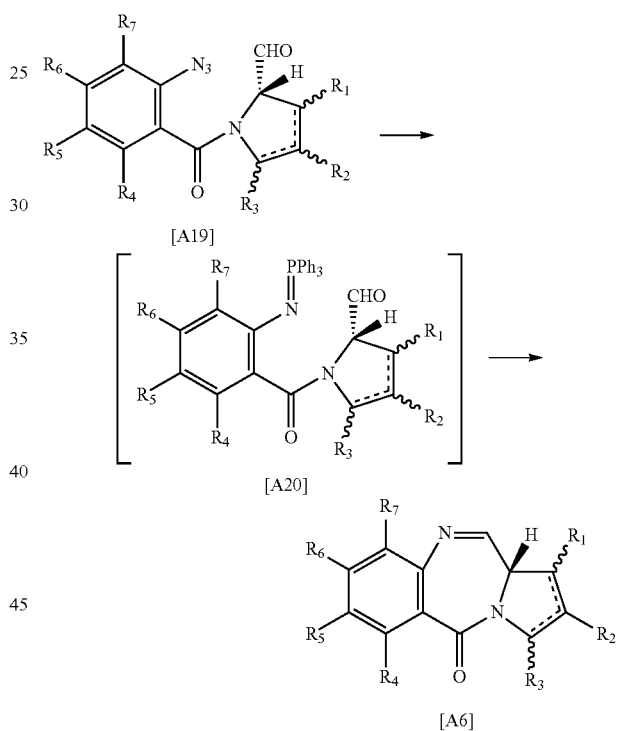

The N-(2-azidobenzoye-pyrrolidine-2-carboxaldehyde derivatives [A19] may be prepared from 2-nitrobenzoic acid derivatives [A1] and pyrrolidine 2-carboxylic ester [A2] or prolinol derivatives. The aldehyde functionality is produced by either reduction of the ester group or oxidation of the alcohol group introduced by [A2] or the prolinol derivative.

Route K

Cyclization of the B-ring may be achieved using a precursor [A21] containing an amine group that has a protecting group at $R_8$ (30, 68-72, WO 00/12508, WO2005/085260). The hydroxyl group in [A21] is oxidised to an aldehyde [A22] which may be reacted with the protected amine to form the carbinolamine [A23]. The protecting group $R_8$ in the carbinolamine [A23] prevents imine formation through elimination, which allows a range of further modifications to be carried out on the compound without any complications from an imine. Thus, [A23] may undergo addition of side chain substituents before formation of the imine. Deprotection of the nitrogen can be carried out as the last step to give the imine [A6].

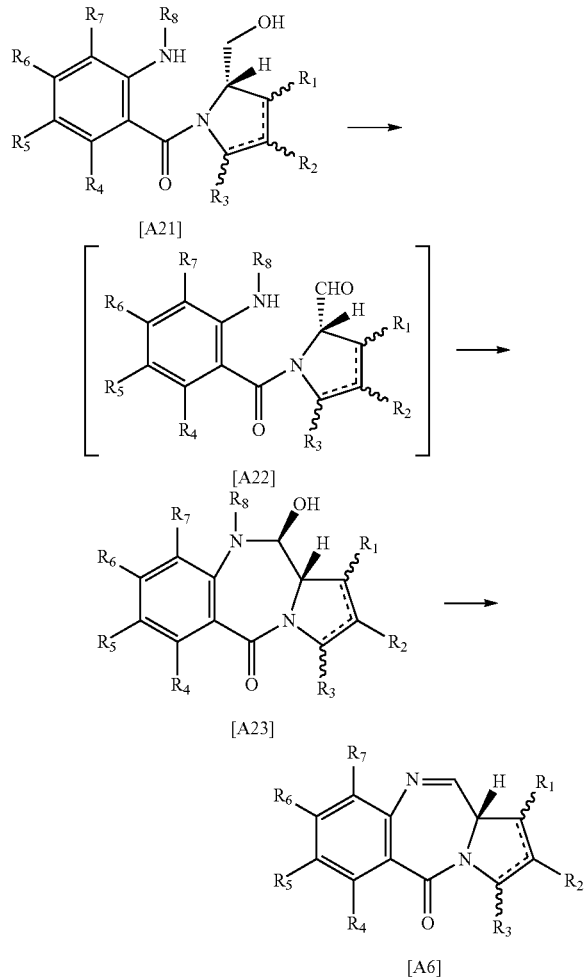

When alloc is used as the protecting group $R_8$, then the deprotection to remove the nitrogen protecting group of [A23] is carried out using palladium, followed by the elimination of water to give the imine.

BRIEF DESCRIPTION OF THE DRAWINGS

Embodiments of the present invention will now be described further, with reference to the accompanying drawings, in which.

EXAMPLES

Figure 1:
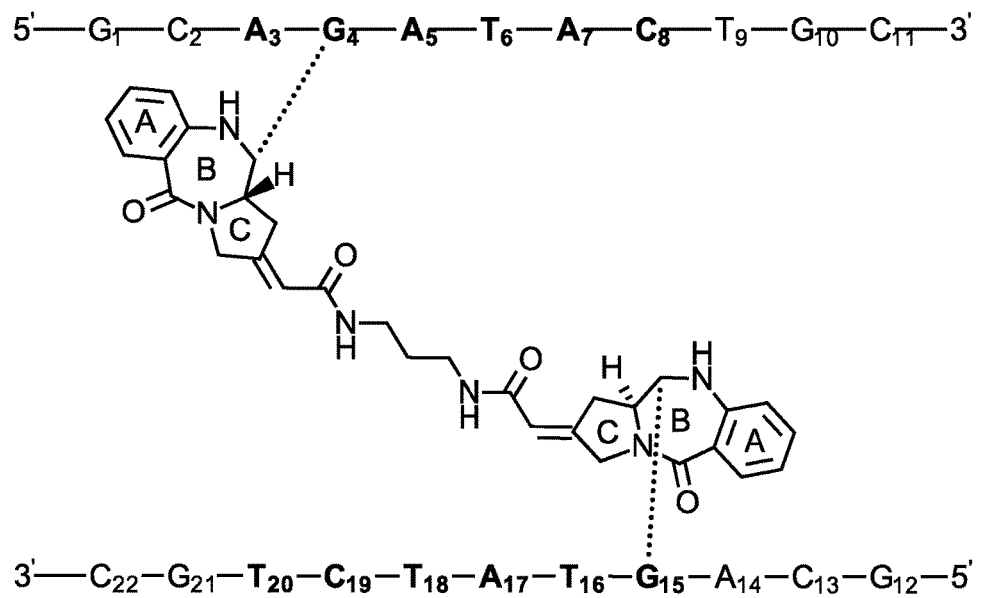
FIG. 1: Schematic showing interaction of a C2-linked PBD dimer with 5'-GCAGATACTGC-3'. The A-ring points in 3' direction, as opposed to C8-linked dimers where it orients in 5' direction.

Synthetic building blocks and reagents were purchased from Maybridge Chemicals (UK), Fluorochem (USA), ChemShuttle Inc (USA) and Sigma-Aldrich (UK). Solvents were purchased from Sigma-Aldrich (UK) and Fisher Scientific (UK). Anhydrous reactions were carried out in pre-oven-dried glassware under an inert atmosphere of nitrogen. Thin Layer Chromatography (TLC) was performed on silica gel aluminum plates (Merck 60, $F_{254}$), and column chromatography was carried out using silica gel (Merck 9385, 230-400 mesh ASTM, 40-63 μM) whilst monitoring by thin layer chromatography: UV (254 nm) and an aqueous alkaline solution of potassium permanganate as stain. All NMR spectra were obtained at room temperature using a Bruker DPX400 spectrometer, for which chemical shifts are expressed in ppm relative to the solvent and coupling constants are expressed in Hz. All Liquid Chromatography Mass Spectroscopy (LCMS) analysis were performed on a Waters Alliance 2695 with water (A) and acetonitrile (B) comprising the mobile phases. Formic acid (0.1%) was added to the acetonitrile to ensure acidic conditions throughout the analysis. The gradient conditions were: 95% A/5% B for 2 mins. which was increased to 50% B over 3 mins. The gradient was then held at 50% B for 1 mins. and then increased to 95% B over 1.5 mins. The quantity of B was then returned to 5% over 1.5 mins. and held constant for 0.5 mins. (the total duration of each run being 10 mins.) The flow rate was 0.5 mL/mins., 200 μL was split via a zero dead volume T piece which passed into the mass spectrometer. The wavelength range of the UV detector was 220-400 nm. Function type: Diode array (535 scans). Column type: Monolithic C18 50×4.60 mm. Mass spectrometry data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. Microwave reactions were carried out on an Anton Paar Monowave 300 microwave synthesis reactor. Yields refer to isolated material (homogeneous by TLC or NMR) unless otherwise stated and names are assigned according to IUPAC nomenclature.

General Methods: Molecular Dynamics (MD) Simulations

Molecular dynamics simulations consist of the calculation of the time-dependent behaviour of molecular systems, and have provided valuable information on the changes in conformations of biomolecules (for example proteins or nucleic acids) as predicted over a certain time-course.

Classical MD simulations can be performed in explicit or implicit solvent, with explicit containing solvent molecules (and thus dramatically increasing the necessary computational power), and implicit solvent containing a representation of solvent in the form of a continuous medium.

In explicit solvent simulations, all atoms contained in the system (i.e. all nucleic acid, ligand and water atoms in a DNA sequence) are moved in short time-steps (e.g. 2fs), each step is saved and the forces acting on the atoms are calculated and an atom's position and velocity are updated using Newton's Laws. This process is repeated billions of times for every atom in the system, resulting in the production of a dynamic simulation trajectory, illustrating an atom's movements within a system. An identical process is undertaken for implicit solvent simulations, except without solvent molecules and as such the complex, on its own, is simulated.

Molecular dynamics simulations were conducted using AMBER (vii) (73, 74) software. Each DNA sequence was constructed using nab, antechamber was used to convert the structures to mol2 files with the application of Gasteiger charges, and missing parameters were generated for each ligand using parmchk. The gaff and DNA optimized parm99bsco (75) force-fields were loaded for DNA and xleap was used to manually position each ligand into each sequence individually by creating the covalent bond between the exocyclic $NH_2$ of the reacting guanine and each ligand, using parameters previously derived through molecular mechanics calculations. Parm99bsco was used as it is a refined version of parm99, where α/γ rotation of nucleic acids is considered (75). $Na^+$ ions were placed along the DNA backbone using xleap to neutralize the DNA, and adducts were solvated using a truncated octahedron TIP3P water box of maximum dimension 10 Å. Each adduct was minimized in a gradient manner by initially placing the DNA under a high force constraint to enable the ligand to find its local energy minimum, followed by a reduction in force in a periodic manner and a relaxation of restraints. Once the full system was minimized, it was heated slowly to 300 K over 20 ps using the SHAKE algorithm to restrict vibrations of C—H bonds (76), followed by an unrestrained equilibration step of 100 ps to relax the density of water. Once in equilibrium, production simulations were run for a period of 10 ns and atomic coordinates were saved at 1-ps intervals. A second set of production simulations of 10 ns were conducted using an identical protocol, with structures non-covalently bound and positioned 2 Å away from the exocyclic amine of the intended reacting guanine.

Simulations of 10 ns duration were undertaken and free energy calculated using the MM-PBSA method in AMBER 11, a method shown to be most accurate in free energy estimation in explicit solvent simulations (77).

Binding free energy can be calculated as follows:

$$\Delta G°_{bind} = \Delta G°_{bind\ vacuum} + \Delta G°_{complex} - (\Delta G°_{ligand} + \Delta G°_{receptor})$$

where $\Delta G°_{bind}$ is determined by solving the linearized Poisson-Boltzmann equation (78)

$$\Delta G°_{complex} = E_{MM} + G_{polar\ solvation\ energy} + G_{nonpolar\ solvation\ energy} - TS$$

Solvation energies (both polar and non-polar) are considered, $E_{MM}$ corresponds to internal, electrostatic and vdW interactions and S is solute entropy.

The final binding energy is represented as:

$$\Delta G°_{bind} = \Delta E_{MM} + \Delta G°_{solv} - T\Delta S$$

Entropy contribution can be calculated using normal mode analysis. However, this is impractical as normal mode analysis calculations introduce significant error into final values and are computationally expensive. As states of similar entropy are being assessed and therefore comparable, these calculations were not undertaken.

$$G = E_{MM} + G_{PBSA} - TS_{MM}$$

$$E_{MM} = E_{bond} + E_{angle} + E_{tors} + E_{vdw} + E_{elec}$$

where:
G=calculated average free energy (kcal/mol),
$G_{PBSA}$=solvation free energy (Poisson Boltzmann equation with estimate of non-polar free energy)
$TS_{mm}$=solute entropy
$E_{MM}$=average molecular mechanical energy
(consisting of energies for bond, angle, torsion, van der Waals and electrostatics One hundred snapshots of the MD simulations were taken at equal intervals over the 10 ns duration, and molecular mechanics (MM) calculations were performed using pbsa (74).

Non-Covalent Simulations

PBDs locate the minor groove of DNA through a combination of hydrophobic and non-covalent interactions, before forming an essential hydrogen bond between N10 of the molecule and the exocyclic C2-amino of guanine. Once this hydrogen bond is formed, the PBD is pulled into the minor groove and undergoes nucleophilic attack to form the covalent attachment. As such, it is necessary to perform non-covalently bound simulations to assess the DNA-interactive potential of DNA-targeting molecules such as PBDs. Free energy of binding calculations performed on these simulations help in the assessment of DNA-binding potential.

Free energy of binding (kcal/mol) calculations are used to ascertain the degree of affinity of a ligand for its receptor. Hydrogen bonding analysis and the examination of non-bonded interactions also support the evaluation of binding of ligands to sequences of DNA. As ligands recognize the minor groove through these interactions, quantitative and qualitative analysis of each provides a valuable insight into the strength of DNA:ligand interaction.

Example 1: MD Simulations of a C2 Dimer

The extended C2 side-chain of a PBD molecule [for example, the polyacrilamide tail in anthramycin (16)] is important for DNA interactivity, with the structure forming stabilizing van der Waals interactions and sequence-specific hydrogen bonds with the minor groove floor. Early studies postulated that without the acrylamide side chain, anthramycin might not be so DNA-interactive (80, 81).

However, the C2 position has been investigated in dimer structures as a potential linking point, with limited success. Examples of this include a C2 dimer produced by Lown et al. (33) (FIG. 1), which showed poor DNA binding relative to C8/C8'-linked dimers. Furthermore, C8/C2' conjugates produced by Kamal et al. (34, 35), showed similarly poor binding with DNA calf thymus melting studies producing results on par with natural monomer structures.

MD simulations of the C2-linked dimer structure (FIG. 2) covalently bound to the binding site 5'-GC<u>AGATAC</u>TGC-3' (5'-pu-GATAC-py-3' underlined) indicated the structure caused DNA distortion due to the steric interaction of the C2 methylene linker with the DNA floor. The A-ring of both PBDs was also contorted and interfered with binding of the ligand to DNA.

C8-linked PBD dimers orient with the A-ring in 3' direction, whereas C2-linked PBD dimers orient with their C-ring pointing in 3' direction. The reversal of directionality may interfere with the ability of the PBD to undergo nucleophilic addition with the C2-amino group of guanine bases, which is reflected in non-covalently bound simulations where the PBD did not form a "pre-covalent" hydrogen bond between its N10 and guanine bases. This may have also occurred due to a lack of non-covalent interaction between the C2-dimer and DNA minor groove floor.

Furthermore the reversal in orientation of the PBD from A-ring pointing in 3' direction [in the case of the active C8-linked molecules (30, 82)] to A-ring pointing in 5' direction may introduce a stereochemical issue. In A-ring 3' orientation (i.e. C8 and C7-linked PBDs), the C11aS configuration ensures the C11a hydrogen group points into the centre of the minor groove, away from the DNA wall, and does not interfere with PBD binding. In the case of C2-linked PBD structures, the C11aS orientation of the PBD is reversed as the PBD itself is rotated 180° on a vertical axis. Simulations suggest that the change in orientation of the C11a hydrogen from pointing away from the minor groove wall, to pointing towards it may impact on the ability of the PBD to interact with DNA by introducing steric interference.

Figure 3:
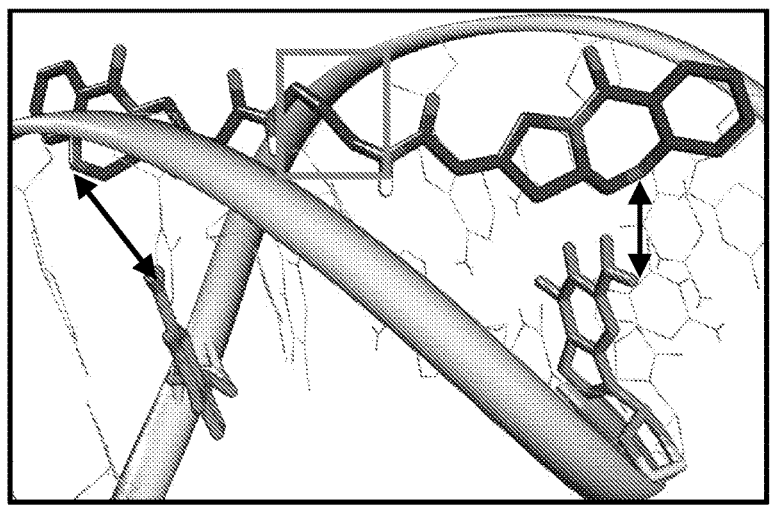
FIG. 3: Shows a snapshot of C2/C2' dimer non-covalently bound to 5'-GCAGATACTGC-3' showing a large distance between potential reacting guanines (magenta) and imine groups of PBD molecules (indicated with arrows). The structure has a distorted linker (green box), is not isohelical and is an inverted crescent shape and therefore does not interact with the minor groove floor.

Simulations of the PBD dimer with one free end and one end covalently attached to the C2-amino group of G4 of 5'-GCA$\underline{G}$ATACTCGC-3' indicated the C2-C2' linker of the structure does not follow the floor of the minor groove, and as such is not DNA interactive, and the second free PBD of the PBD dimer was not in the correct orientation to interact with G15. Non-covalently bound simulations suggested similar characteristics, with a non-isohelical C2-C2' linked structure failing to form non-covalent interactions with the minor groove floor (FIG. 3).

Example 2: MD Simulations of a C1-Dimer

Simulations of the C1-linked PBD dimer suggested enhanced DNA binding ability over the C2-linked structure. In non-covalently bound simulations, the C1-linked dimer maintained a position directly over the reacting guanine for the duration of the simulation (i.e. $G_4$ of 5'-GCA$\underline{G}$ATACTGC-3'). It is important to note the linking group between each C1 of the PBD dimer is in the correct orientation to interact with the minor groove floor in non-covalent simulations, exemplified by favourable free energy of binding values (−7.6 kcal/mol difference in favour of C1-linked dimer structure).

TABLE 1

Structures and Free Energy of Binding Values of $C_1$-Linked and $C_2$-Linked Dimers with 5'-GCGATACTCGC-3'

| Structure | Free Energy of Binding (kcal/mol) |
|---|---|
| C1-linked dimer | −50.42 |
| C2-linked dimer | −42.74 |

In a similar manner to the C2-linked dimer, the second free PBD is not in the correct orientation to interact with its binding guanine (G16) in simulations of single covalent attachment or non-covalently bound simulations, suggesting a single covalent attachment is favoured.

Figure 2:
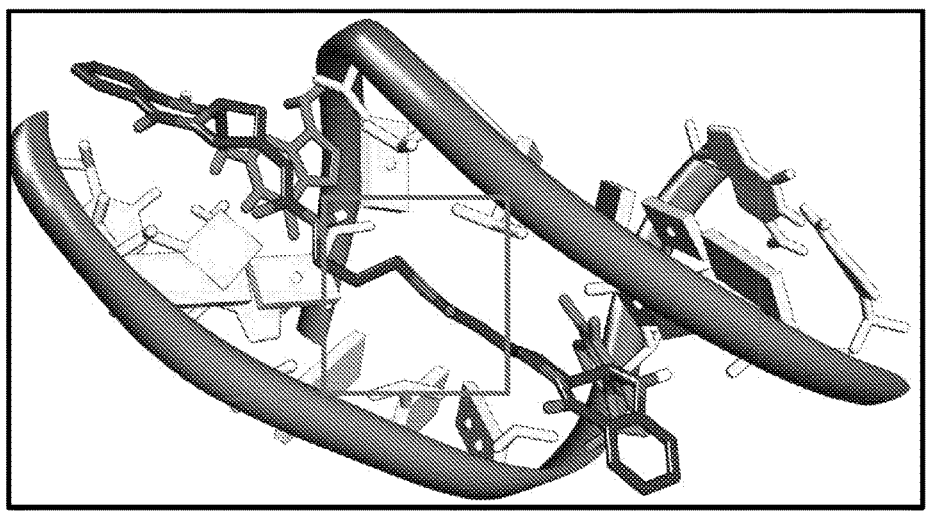
FIG. 2: Shows a snapshot of a C2/C2' dimer covalently bound to G4 and G14 (both magenta) of 5'-GCAGATACTGC-3'. Distortion of DNA is evident with base pair (yellow nucleotide objects) displacement occurring in the central ATA region (red box)
Figure 4:
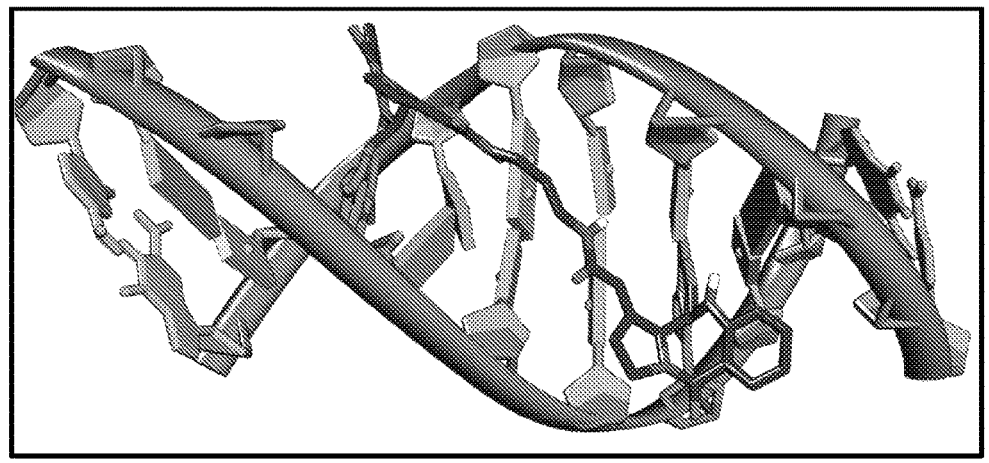
FIG. 4: Shows a snapshot of molecular dynamics simulation of C1/C1' linked PBD structure (blue) covalently bound to G4 and G15 (both magenta) of 5'-GCAGATACTGC-3'. There is a lack of DNA distortion compared to the C2-linked dimer (FIG. 2) with DNA bases (orange nucleotide objects) remaining ordered.

A snapshot of the MD simulation for a C1/C1' linked PBD structure (shown in FIG. 4) lacks DNA distortion as compared to the C2/C2' linked dimer (shown in FIG. 2).

As simulations progressed, covalently bound simulations of C1-linked dimer suggested some degree of DNA distortion which may be caused by unfavourable interactions between an inappropriate linker and the DNA floor.

Example 3: MD Simulations of C1-Conjugates

The C8-linked PBD monomeric conjugate KMR-28-39 has femtomolar activity against some cancer cell lines. The structure, when linked to an imidazole group, is known to be GC-selective when interacting with DNA, a feature thought to contribute to its enhanced DNA binding affinity and cytotoxicity. The MPB moiety provides the structure with its GC-selectivity (82).

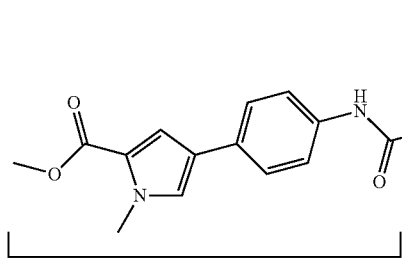

GC-selective MPB moiety

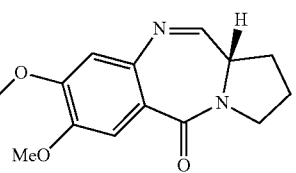

KMR 28-39 (PBD-C8-Imidazole-MPB)

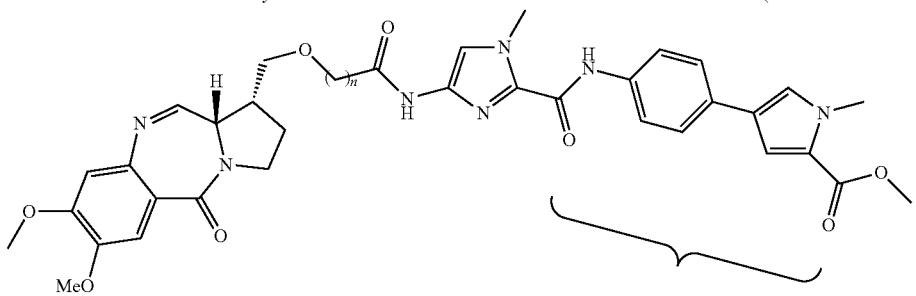

PBD Conjugate-PBD-C1-Imidazole-MPB       GC-selective MPB moiety

When the Imidazole-MPB moiety is tethered to the C1 position, the new PBD-C1-Imidazole-MPB structure produces the same interactions with DNA as KMR-28-39 (PBD-C8-Imidazole-MPB). This is exemplified in snapshots of MD simulations of KMR-28-39 (PBDC8-Imidazole-MPB) and PBDC1-Imidazole-MPB which shows identical hydrogen bonding interactions are formed between each structure and the DNA sequence (FIG. 3).

Figure 5:
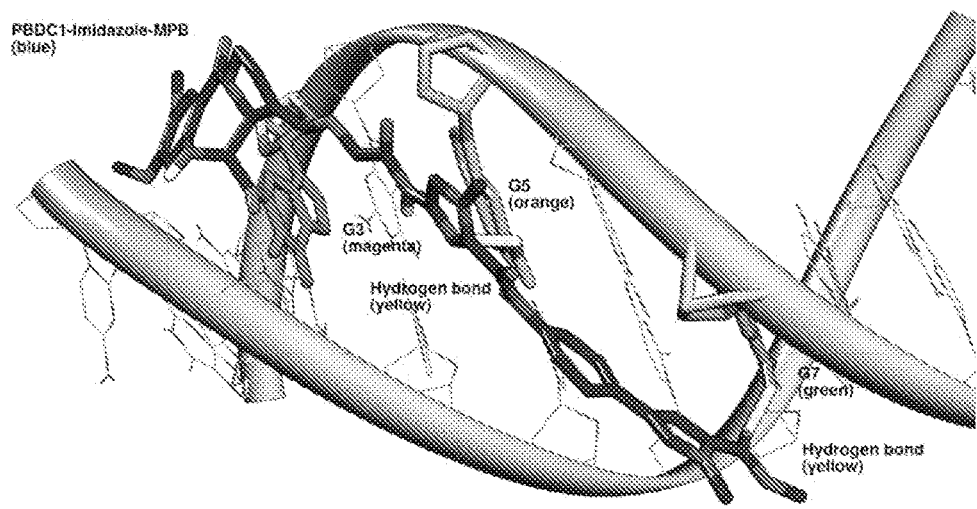
FIG. 5: Shows a snapshot of MD Simulation of PBD-C1-Imidazole-MPB interacting with 5'-GGGGGGGGCC-3' with the formation of two sequence selective H bonds (yellow)
Figure 6:
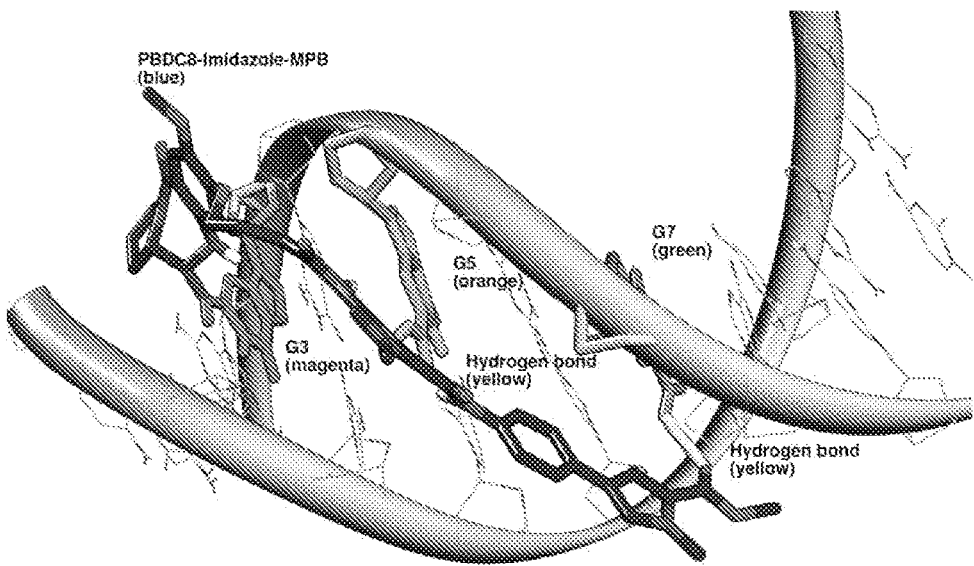
FIG. 6: Shows a snapshot of MD Simulation of the highly cytotoxic KMR-28-39 (PBD-C8-Imidazole-MPB) interacting with 5'-GGGGGGGGCC-3' in an identical manner to PBD-C1-Imidazole-MPB as shown in FIG. 5.

When modelled with the poly-guanine DNA sequence 5'-GGGGGGGGCC-3' and covalently bound to G3 (underlined), hydrogen bonding interactions are formed between the ring nitrogen of imidazole and G5, and the terminal carbonyl and G7 in the case of both PBD-C1-Imidazole-MPB and PBD-C8-Imidazole-MPB (FIGS. 5 and 6). As such, C1-linked PBD conjugates are expected to produce similarly high cytotoxicity to C8-linked PBD structures.

Example 4: Synthesis of C-Ring Precursor

The C-ring precursor 6 may be prepared as shown in the reaction scheme above. Commercially available trans-3-hydroxy-L-proline (Sigma-Aldrich) is N-protected (69, 84, 85) as the benzyl carbamate 2 and the carboxylic acid is then esterified and subsequently is reduced to the alcohol 4 (30). One of the alcohol groups may be protected with using TBDMS chloride and the N-protecting group may be removed to give the C-ring precursor 6 (84, 85). The following reagents and conditions may be used.

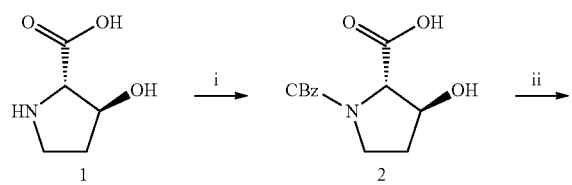

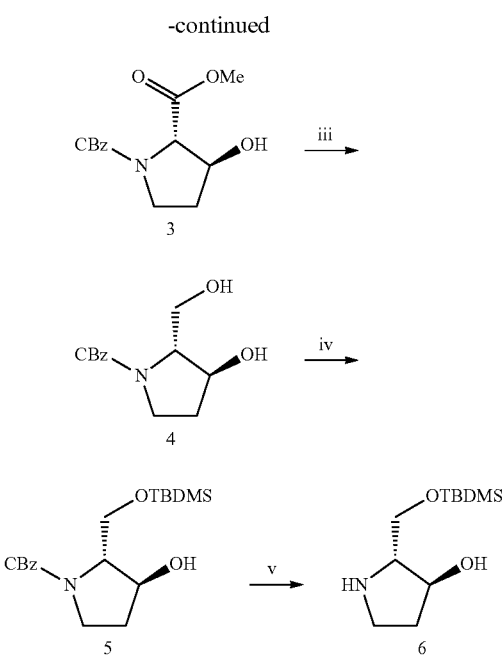

Reagents and Conditions:

(i) CBzCl, NaHCO$_3$, Et$_2$O; (ii) MeOH, H$_2$SO$_4$, Reflux; (iii) LiBH$_4$, THF, 0° C.; (iv) TBDMSCl, TEA, DBU, CH$_2$Cl$_2$; (v) 10% Pd/C, H$_2$, EtOH.

Example 5

A suitable PBD scaffold is prepared by reacting the C-ring precursor 6 from Example 4 in the following reaction scheme:

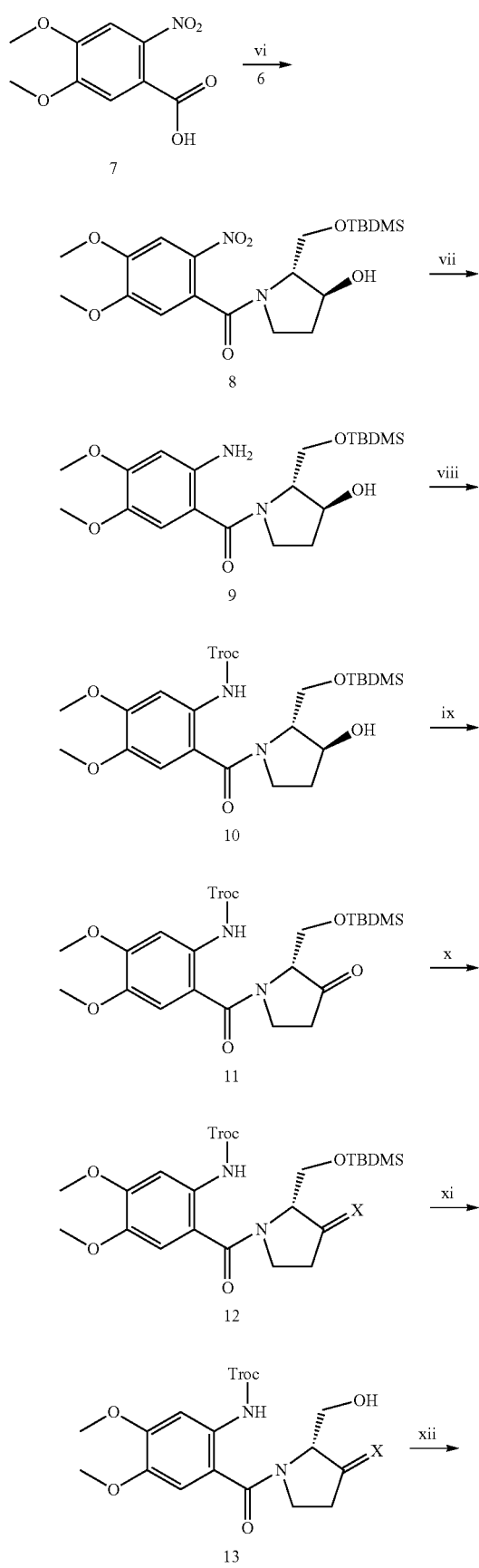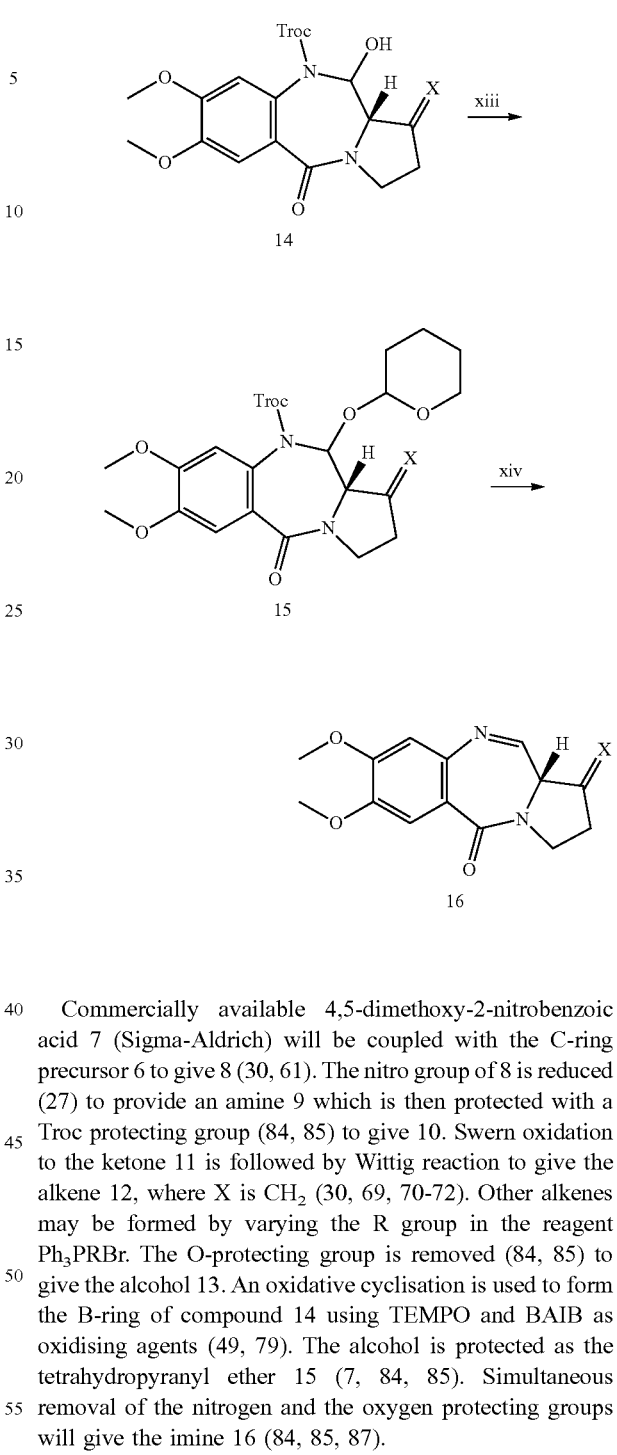

Commercially available 4,5-dimethoxy-2-nitrobenzoic acid 7 (Sigma-Aldrich) will be coupled with the C-ring precursor 6 to give 8 (30, 61). The nitro group of 8 is reduced (27) to provide an amine 9 which is then protected with a Troc protecting group (84, 85) to give 10. Swern oxidation to the ketone 11 is followed by Wittig reaction to give the alkene 12, where X is $CH_2$ (30, 69, 70-72). Other alkenes may be formed by varying the R group in the reagent $Ph_3PRBr$. The O-protecting group is removed (84, 85) to give the alcohol 13. An oxidative cyclisation is used to form the B-ring of compound 14 using TEMPO and BAIB as oxidising agents (49, 79). The alcohol is protected as the tetrahydropyranyl ether 15 (7, 84, 85). Simultaneous removal of the nitrogen and the oxygen protecting groups will give the imine 16 (84, 85, 87).

Reagents and Conditions:

(vi) $(COCl)_2$, DMF, $CH_2Cl_2$, then 6, TEA, $CH_2Cl_2$, 0° C.; (vii) Raney Ni, $H_2NNH_2$, MeOH or $H_2$/Pd—C; (viii) Trichloroethyl chloroformate, pyridine, $CH_2Cl_2$, 0° C.; (ix) $(COCl)_2$, DMSO, TEA, $CH_2Cl_2$, −60° C.; (x) $Ph_3PRBr$, KOtBu, THF, 0° C. (R=alkylene=$CH_2$); (xi) TBAF, THF, 0° C.; (xii) TEMPO, BAIB, $CH_2Cl_2$, RT; (xiii) DHP, PTSA, EtOAc, RT; (xiv) 10% Cd—Pd or 10% Cd—Pb.

Example 6
Structure type
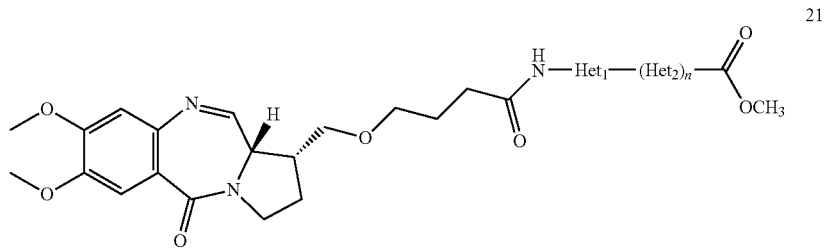
A monomeric compound 21 as shown above, where Het$_1$ is a heteroarylene group (e.g. 1-methyl-1H-imidazole) and Het$_2$ is a unit, which may be a repeating unit with n=1–10, comprising a linking group and a heteroaryl group, e.g. —(C(O)—NH-phenylene-N-methylpyrrolylene)-, is prepared by the following reaction scheme using the C-ring precursor from Example 4.
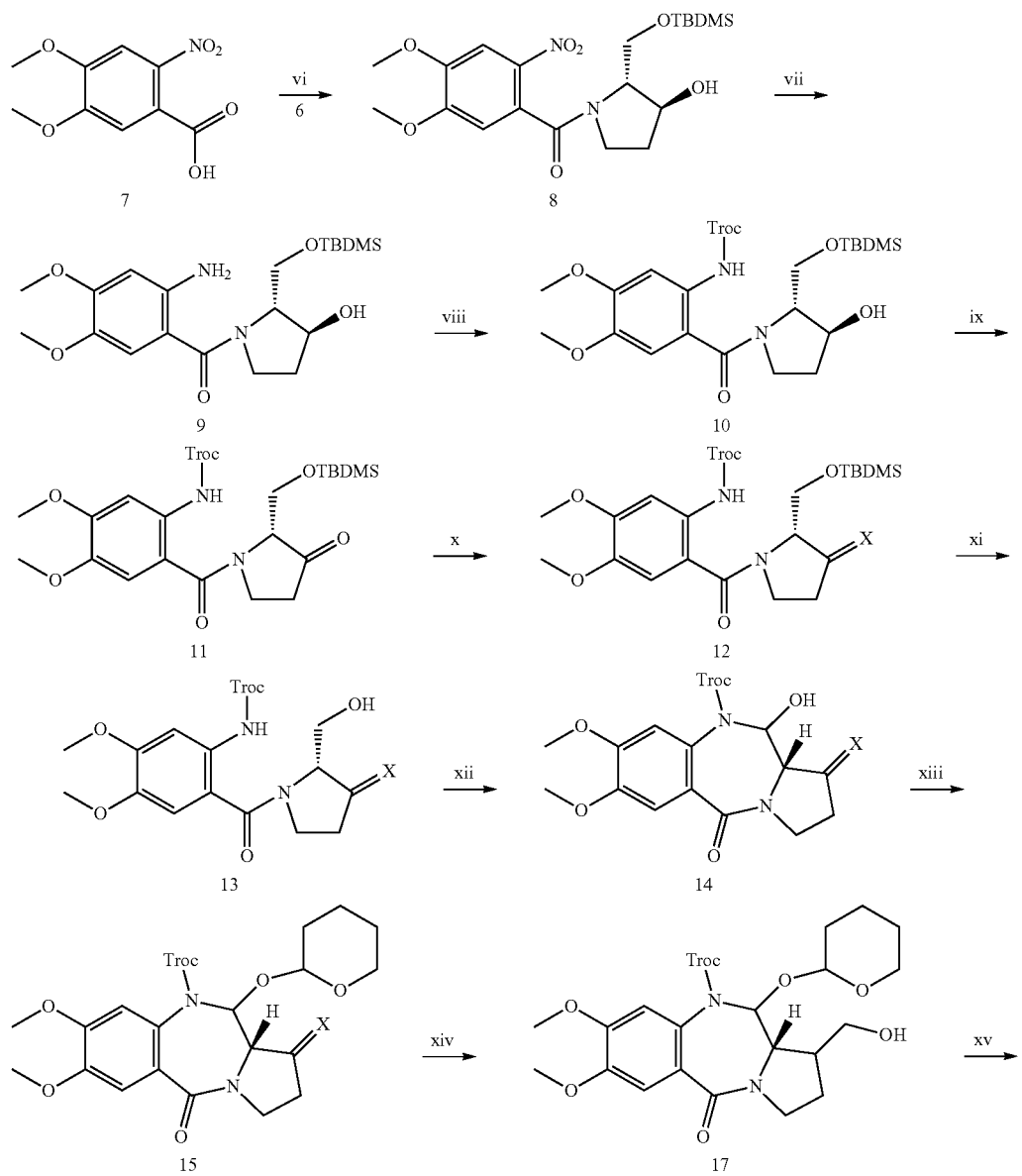

-continued

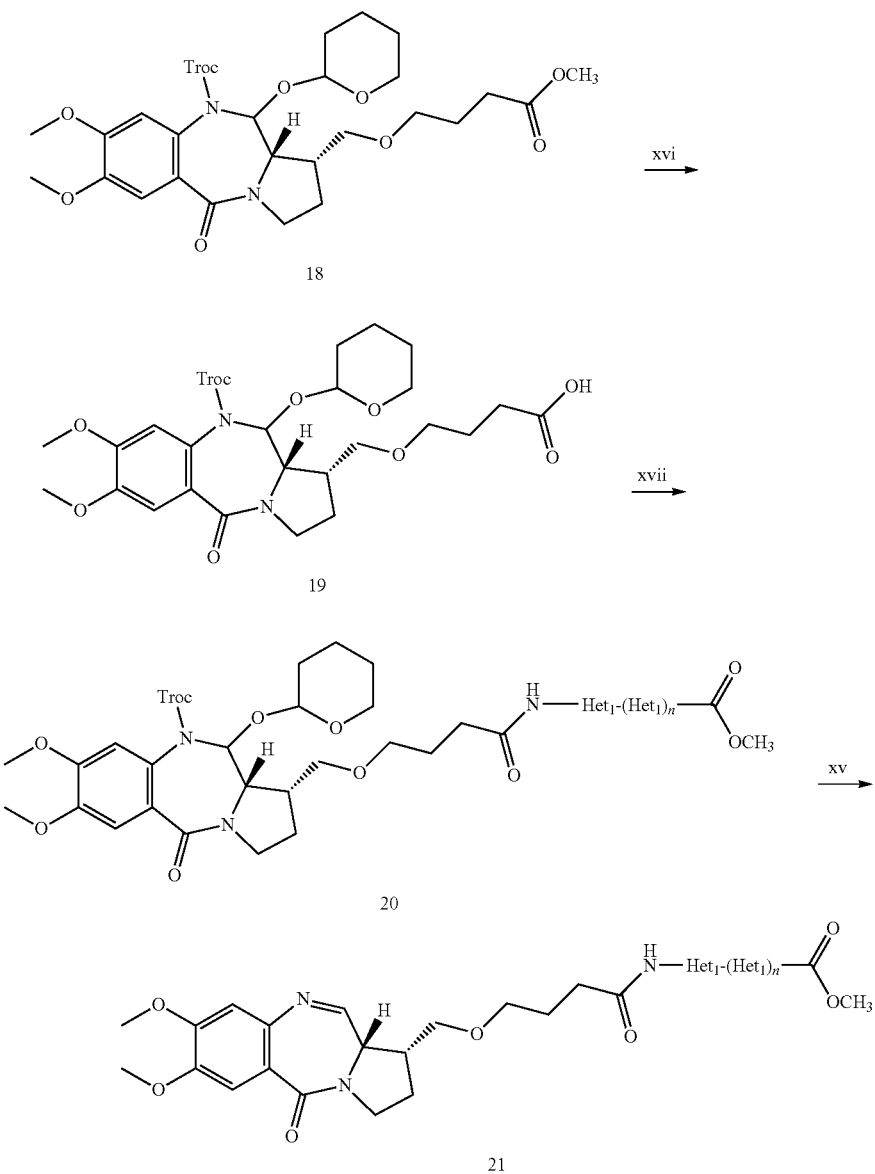

Commercially available 4,5-dimethoxy-2-nitrobenzoic acid 7 (Sigma-Aldrich) will be converted into the tetrahydropyranyl ether 15 where X is CH$_2$, as described above in Example 5. The alkene group in 15 is converted by hydroboration-oxidation into the alcohol 17 (88). The alcohol is coupled with methyl 4-bromobutyrate (Alfa Aesar) to give the product 18 (7, 83). Hydrolysis of the ester is carried out under basic conditions to give the acid 19. The acid is coupled (83, 86) with a suitable heterocyclic amine (22-26, 83, 86) such as methyl 4-[(4-amino-1-methyl-1H-imidazole-2-carboxamino)phenyl]-1-methyl-/H-pyrrole-2-carboxylate [which is designated as Im-MPB and is prepared as described in Ex. 2 of (86)] to give the protected product 20. Simultaneous removal of the nitrogen and the oxygen protecting groups will give the imine 21 (84, 85, 87).

Reagents and Conditions:
(vi) (COCl)$_2$, DMF, CH$_2$Cl$_2$, then 6, TEA, CH$_2$Cl$_2$, 0° C.; (vii) Raney Ni, H$_2$NNH$_2$, MeOH or H$_2$/Pd—C; (viii) Trichloroethyl chloroformate, pyridine, CH$_2$Cl$_2$, 0° C.; (ix) (COCl)$_2$, DMSO, TEA, CH$_2$Cl$_2$, −60° C.; (x) Ph$_3$PRBr, KOtBu, THF, 0° C. (R=alkyl); (xi) TBAF, THF, 0° C.; (xii) TEMPO, BAIB, CH$_2$Cl$_2$, RT; (xiii) DHP, PTSA, EtOAc, RT; (xiv) BH$_3$, THF followed by H$_2$O$_2$, NaOH; (xv) K$_2$CO$_3$, DMF, CH$_3$OC(O)—(CH$_2$)$_3$Br, 90° C.; (xvi) NaOH, Dioxane, RT; (xvii) CH$_3$OC(O)-(Het$_2$)$_n$-Het$_1$-NH$_2$, EDCl, DMAP, DMF; (xviii) 10% Cd—Pd or 10% Cd—Pb.

Example 7

A further monomeric compound as shown below, where Het$_1$ is a heteroarylene group (e.g. 1-methyl-1H-imidazole) and Het$_2$ is a unit, which may be a repeating unit with n=1-10, comprising a linking group and a heteroaryl group, e.g. —(C(O)—NH-phenylene-N-methylpyrrolylene)—, is prepared by the following reaction scheme.

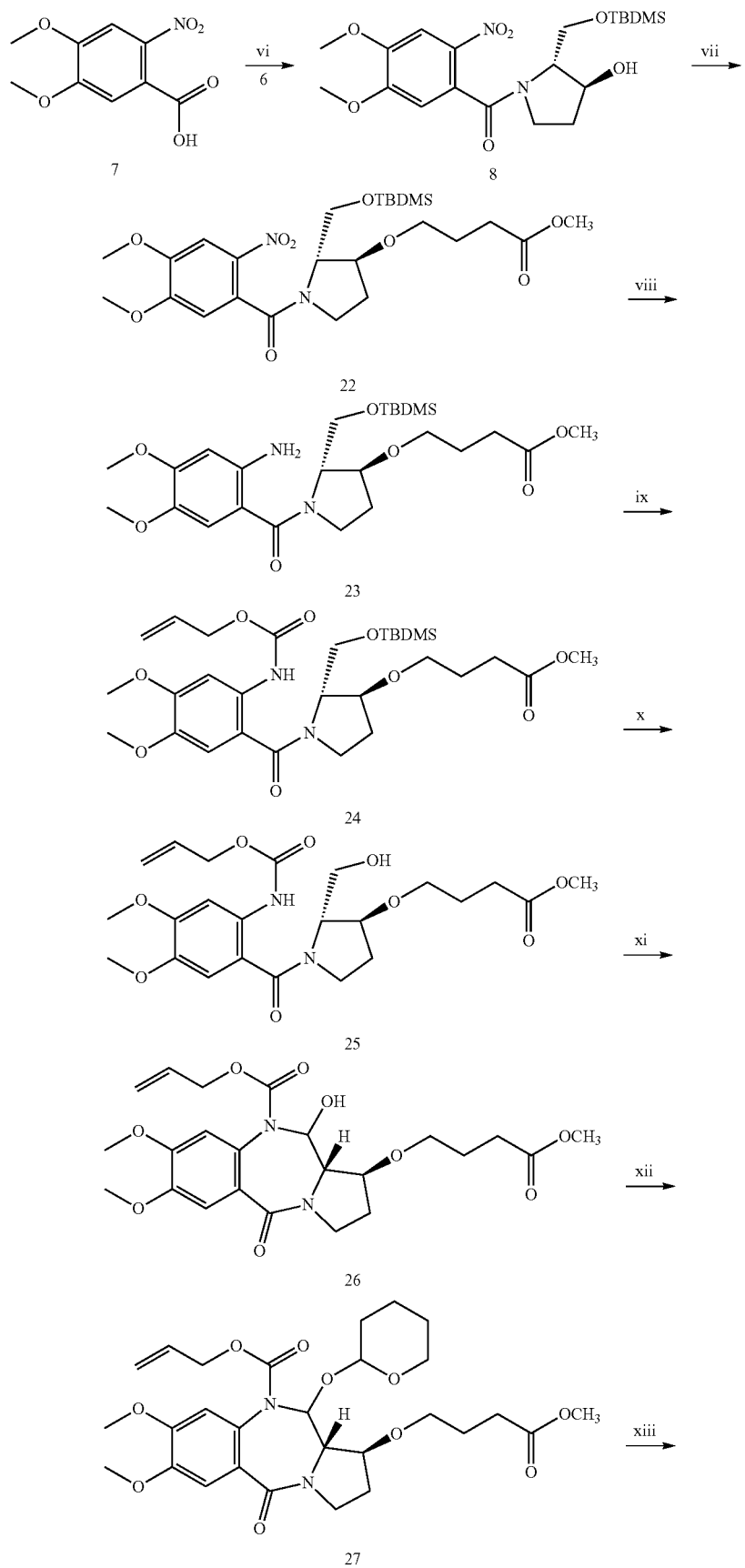

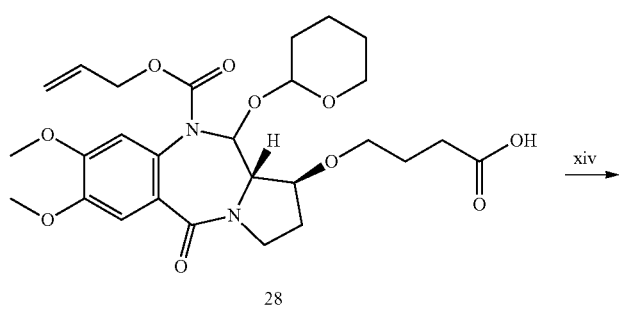

28

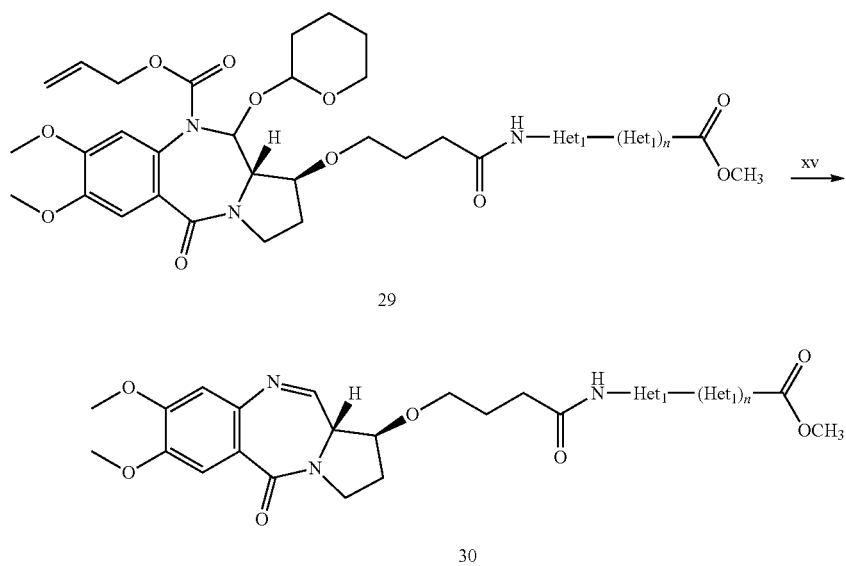

29

30

Commercially available 4,5-dimethoxy-2-nitrobenzoic acid 7 (Sigma-Aldrich) will be coupled with the C-ring precursor 6 to give 8 (30, 61). The alcohol is coupled with methyl 4-bromobutyrate (Alfa Aesar) to give the product 22 (7, 83). The nitro group of 22 is reduced (27) to provide an amine 23 which is then protected with an alloc protecting group (84, 85) to give 24. The O-protecting group is removed (84, 85) to give the alcohol 25. An oxidative cyclisation is used to form the B-ring of compound 14 using TEMPO and BAIB as oxidising agents (49, 79). The alcohol is protected as the tetrahydropyranyl ether 27 (7, 84, 85). Hydrolysis of the ester is carried out under basic conditions to give the acid 28. The acid is coupled (83, 86) with a suitable heterocyclic amine (22-26, 83, 86) such as methyl 4-[(4-amino-1-methyl-1H-imidazole-2-carboxamino)phenyl]-1-methyl-1H-pyrrole-2-carboxylate [which is designated as Im-MPB and is prepared as described in Ex. 2 of (86)] to give the protected product 29. Simultaneous removal of the nitrogen and the oxygen protecting groups will give the imine 30 (7, 83, 84, 85).

Reagents and Conditions:

(vi) $(COCl)_2$, DMF, $CH_2Cl_2$, then 6, TEA, $CH_2Cl_2$, 0° C.; (vii) $K_2CO_3$, DMF, $CH_3OC(O)—(CH_2)_3Br$, 90° C.; (viii) Raney Ni, $H_2NNH_2$, MeOH or $H_2/Pd—C$; (ix) Allylchloroformate, pyridine, $CH_2Cl_2$, 0° C.; (x) TBAF, THF, 0° C.; (xi) TEMPO, BAIB, $CH_2Cl_2$, RT; (xii) DHP, PTSA, EtOAc, RT; (xiii) NaOH, Dioxane, RT; (xiv) $CH_3OC(O)$-$(Het_2)_n$-$Het_1$-$NH_2$, EDCl, DMAP, DMF; (xv) $Pd(PPh_3)_4$, $PPh_3$, pyrrolidine, $CH_2Cl_2$.

Example 8

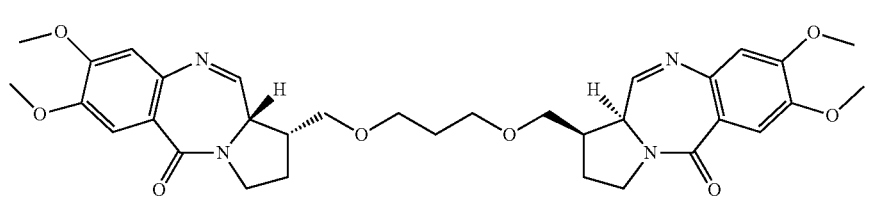

32

A dimer compound 32 of the structure type shown above is prepared by reacting the C-ring precursor 6 from Example 4 in the following reaction scheme:
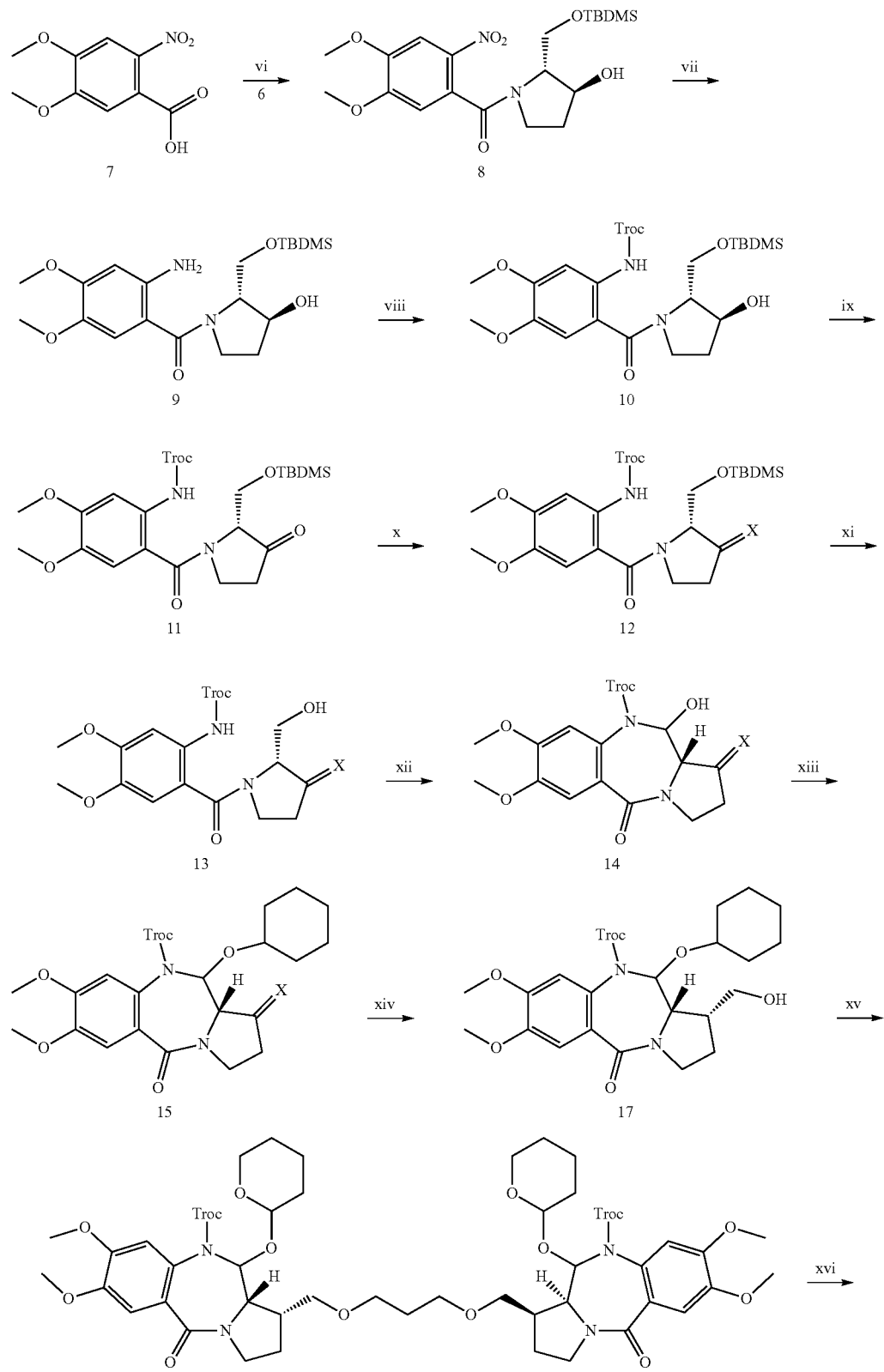

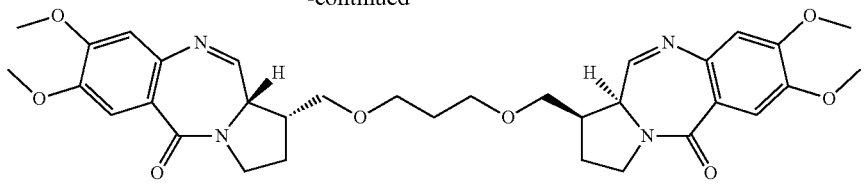

32

Commercially available 4,5-dimethoxy-2-nitrobenzoic acid 7 (Sigma-Aldrich) will be converted into the alcohol 17, as described above in Example 6. Reflux of alcohol 17 with a diiodoalkane gives the protected dimeric compound 31 (61). Simultaneous removal of the nitrogen and the oxygen protecting groups will give the imine 32 (84, 85, 87).
Reagents and Conditions:

(vi) $(COCl)_2$, DMF, $CH_2Cl_2$, then 6, TEA, $CH_2Cl_2$, 0° C.; (vii) Raney Ni, $H_2NNH_2$, MeOH or $H_2$/Pd—C; (viii) Trichloroethyl chloroformate, pyridine, $CH_2Cl_2$, 0° C.; (ix) $(COCl)_2$, DMSO, TEA, $CH_2Cl_2$, −60° C.; (x) $Ph_3PRBr$, KOtBu, THF, 0° C. (R=alkyl); (xi) TBAF, THF, 0° C.; (xii) TEMPO, BAIB, $CH_2Cl_2$, RT; (xiii) DHP, PTSA, EtOAc, RT; (xiv) $BH_3$, THF followed by $H_2O_2$, NaOH; (xv) $I(CH_2)_3I$, THF, NaOH, 90° C.; (xvi) 10% Cd—Pd or 10% Cd—Pb.

Example 9: HPLC Assay

Ligand-DNA Complex Preparation:

Ligand-DNA complexes will be prepared by incubating the ligands with hairpin oligonucleotides of chosen sequence in a 4:1 molar ratio at room temperature. Samples will be withdrawn at various time intervals and subjected to Ion-Pair RPLC and mass spectrometry analysis as described below.

Ion-Pair Reversed-Phase Liquid Chromatography:

Chromatography will be performed on a Thermo Electron HPLC system equipped with a 4.6×50 mm Xterra MS C18 column packed with 2.5 μM particles (Waters Ltd, UK), an UV woo detector, an AS3000 autosampler, a SCM1000 vacuum degasser and Chromquest software (Version 4.1). A gradient system of 100 mM triethyl ammonium bicarbonate (TEAB) as buffer A, and 40% acetonitrile in water (HPLC grade, Fischer Scientific UK) as buffer B will be used. For buffer A, a 1 M pre-formulated buffer of TEAB (Sigma-Aldrich, U.K) will be diluted to 100 mM with HPLC grade water (Fischer Scientific, U.K). The gradient will be ramped from 90% A at 0 mins to 50% A at 20 mins, 65% A at 30 mins and finally to 10% A at 45 mins. UV absorbance will be monitored at 254 nm, and fractions containing separated components will be collected manually, combined when appropriate, lyophilized and analyzed using MALDI TOF mass spectrometry as described below.

Mass Spectrometry Analysis (ESI-MS):

ESI-MS spectra will be acquired on a Micromass Q-TOF Global Tandem Mass Spectrometer (Waters, UK) fitted with a NanoSpray ion source. Negative mode will be used for data acquisition, and the instrument will be calibrated with ions produced from a standard solution of taurocholic acid (10 pmole/μl) in acetonitrile. The HPLC fractions will be collected and lyophilized (Speedvac, Thermo Electron, UK) and mixed with a 1:1 v/v mixture of 40% acetonitrile/water and 20 mM triethylamine/water (TEA, Fischer Scientific, UK) which will also be used as electrospray solvent. 3-5 μL of sample will be loaded into a metal-coated borosilicate electrospray needle with an internal diameter of 0.7 mm and a spray orifice of ~10 mm (NanoES spray capillaries, Proxeon Biosystems, UK) which will be positioned at 10 mm from the sample cone to provide a flow rate of ~20 nl/min. Nitrogen will be used as the API gas, and the capillary, cone and RF Lens 1 voltages will be set to values such as 1.8-2.0 kV, ~35 V and 50 V, respectively, to ensure minimum fragmentation of the ligand/DNA adducts. The collision and MCP voltages will be set to values such as 5V and 2200 V, respectively. Spectra will be acquired over the m/z range 1000-3000.

Mass Spectrometry Analysis (MALDI TOF):

Samples will be diluted with matrix (37 mg THAP in 1 mL ACN, 45 mg ammonium citrate in 1 mL water—mixed 1:1 for matrix) either 2:1, 1:1 or 1:5 (sample:matrix) to determine the most effective ratio. 1 μl of sample/matrix mixture will be spotted onto the MALDI target plate and allowed to dry. Analyses will be carried out on a Voyager DE-Pro with a nitrogen laser in positive linear mode using delayed extraction (500 nsec) and an accelerating voltage of 25,000 V. Acquisition will be between 4000-15000 Da with 100 shots/spectrum.

Example 10: Fluorescent Resonance Energy Transfer (FRET) DNA Thermal Denaturation Assay 400 nM solutions of fluorescence-tagged oligonucleotide (e.g., 5'-Fam-TATA-$(X)_n$-TATA-Tamra-3'; where X=any number or combination of bases) in FRET buffer (50 mM potassium cacodylate, pH 7.4) will be prepared by diluting a 20 μM stock solution in water. This solution will be heated at 85° C. for 5 mins before cooling to room temperature over 5 hours to promote annealing. The ligand solution will be prepared initially in a concentration double that required for the final solution, and dilution from the initial 10 mM DMSO stock solution will be carried out using FRET buffer. 50 μL of the annealed DNA and 50 μL of ligand solution will be placed in a well of a 96-well plate (MJ Research Inc, USA) which will be processed in a DNA Engine Opticon (MJ Research). Fluorescence readings will be taken at intervals of 0.5° C. over the range 30-100° C., with a constant temperature maintained for 30 seconds prior to each reading. The incident radiation will be 450-495 nm with detection at 515-545 nm. The raw data will be imported into the Origin program (Version 7.0, OriginLab Corp. USA), and the graphs smoothed using a 10-point running average prior to normalization. Determination of melting temperatures will be based on obtaining values at the maxima of the first derivative of the smoothed melting curves using a script. The difference between the melting temperature of the sample and that of the blank (i.e., the ΔTm) will be used for comparative purposes.

Example 11: Methyl (2S,3S)-3-hydroxypyrrolidine-2-carboxylate hydrochloride (33)

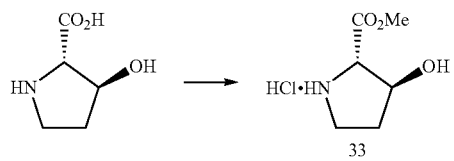

To a stirred suspension of (2S,3S)-3-hydroxypyrrolidine-2-carboxylic acid (2.0 g, 15.2 mmol) in anhydrous methanol (40 mL) at 0° C., thionyl chloride (2.2 mL, 30.4 mmol) was added dropwise. The reaction mixture was stirred at room temperature for 16 h. The reaction mixture was then concentrated in vacuo and the residue was triturated in anhydrous diethyl ether, filtered, washed with extra diethyl ether and concentrated to give the title compound (2.5 g, 91%) as a beige solid. The obtained material was carried through to the next step without any further purification.

$^1$H NMR (400 MHz, MeOD) δ 4.66 (br s, 1H) 4.30 (s, 1H) 3.82-3.91 (m, 3H) 3.46-3.59 (m, 2H) 2.07 (br s, 2H); $^{13}$C NMR (100 MHz, MeOD) δ 169.1, 74.5, 68.6, 54.5, 45.8, 33.2.

Example 12: Methyl (2S,3S)-1-(4,5-dimethoxy-2-nitrobenzoyl)-3-hydroxypyrrolidine-2-carboxylate (34)

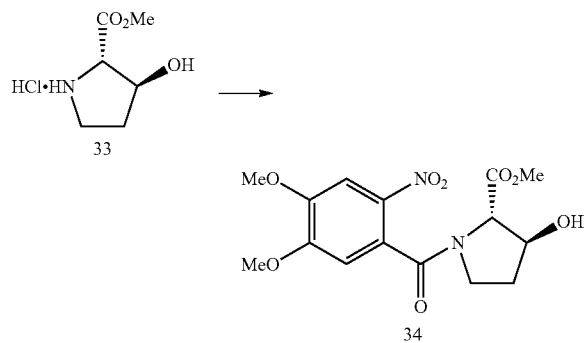

A mixture of 4,5-dimethoxy-2-nitrobenzoic acid (2.4 g, 10.6 mmol), oxalyl chloride (2.7 mL, 31.8 mmol) and anhydrous N,N-dimethylformamide (2 drops) in anhydrous dichloromethane (50 mL) was stirred at room temperature for 1 h. Anhydrous toluene (20 mL) was added to the reaction mixture which was then concentrated in vacuo. A solution of the resulting residue in anhydrous dichloromethane (10 mL) was added dropwise to a solution of methyl (2S,3S)-3-hydroxypyrrolidine-2-carboxylate hydrochloride (33) (2.5 g, 13.8 mmol) and triethylamine (4.4 mL, 31.8 mmol) in anhydrous dichloromethane (40 mL) at 10° C. The reaction mixture was stirred at room temperature for 2 h and then washed with hydrochloric acid (1 M, 50 mL) and brine (50 mL), dried over sodium sulfate, filtered and concentrated. The resulting residue was purified by column chromatography (silica), eluting with methanol/dichloromethane (from 0% to 50%), to give the title compound (3.5 g, 91%) as a yellow solid.

$^1$H NMR (400 MHz, CDCl$_3$) δ 7.70 (s, 1H) 6.89-6.90 (m, 1H) 4.73 (s, 1H) 4.51-4.56 (m, 1H) 4.00 (s, 3H) 3.98 (s, 3H) 3.81 (s, 3H) 3.57 (s, 1H) 3.40-3.47 (m, 1H) 3.34 (td, 1H, J=9.2, 3.0 Hz) 2.07-2.20 (m, 2H); $^{13}$C NMR (100 MHz, CDCl$_3$) δ 170.4, 167.1, 154.4, 149.2, 137.4, 127.0, 109.3, 107.0, 73.6, 67.5, 56.9, 56.5, 52.7, 46.3, 32.7; MS (ES+): m/z=355 (M+H)$^+$; LCMS: t$_R$=5.15 mins.

Example 13: Methyl (2S,3S)-3-((tert-butyldimethylsilyl)oxy)-1-(4,5-dimethoxy-2-nitrobenzoyl)pyrrolidine-2-carboxylate (35)

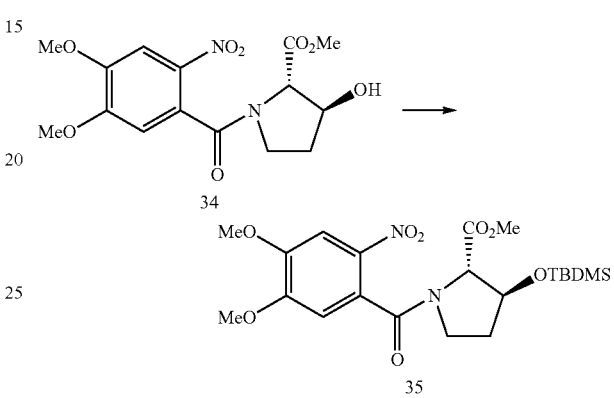

A mixture of methyl (2S,3S)-1-(4,5-dimethoxy-2-nitrobenzoyl)-3-hydroxypyrrolidine-2-carboxylate (34) (1.47 g, 4.15 mmol), tert-butyldimethylsilyl chloride (750 mg, 4.98 mmol) and imidazole (707 mg, 10.4 mmol) in anhydrous dichloromethane (20 mL) was stirred at room temperature for 3 h. The reaction mixture was concentrated in vacuo and partitioned between diethyl ether (3×20 mL) and water (30 mL). The organic layer was dried over sodium sulfate, filtered and concentrated to give the title compound (1.9 g, 91%) as a yellow oil. The resulting material was carried through to the subsequent step without any further purification.

MS (ES+): m/z=469 (M+H)+; LCMS: t$_R$=8.20 mins.

Example 14: ((2R,3S)-3-((tert-Butyldimethylsilyl)oxy)-2-(hydroxymethyl)-pyrrolidin-1-yl)(4,5-dimethoxy-2-nitrophenyl)methanone (36)

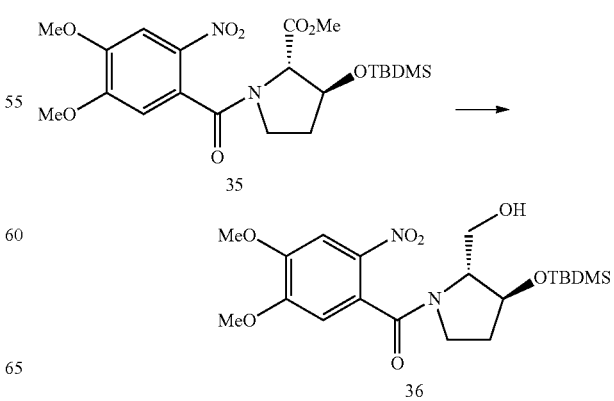

Lithium borohydride (2M in THF, 2.8 mL, 5.6 mmol) was added slowly to a solution of methyl (2S,3S)-3-((tert-butyldimethylsilyl)oxy)-1-(4,5-dimethoxy-2-nitrobenzoyl)-pyrrolidine-2-carboxylate (35) (1.9 g, 3.8 mmol) in anhydrous tetrahydrofuran (20 mL) at 0° C. The reaction mixture was stirred at room temperature for 2 h. Water (80 mL) was then added carefully to the reaction mixture at 0° C. which was extracted with ethyl acetate (3×50 mL). The organic layer was dried over sodium sulfate, filtered and concentrated to give the title compound (1.8 g, 99%) as a yellow oil. The resulting material was carried through to the next step without any further purification.

MS (ES+): m/z=441 (M+H)+; LCMS: $t_R$=7.80 mins.

Example 15: (2-Amino-4,5-dimethoxyphenyl)((2R, 3S)-3-((tert-butyldimethylsilyl)oxy)-2-(hydroxymethyl) pyrrolidin-1-yl)methanone (37)

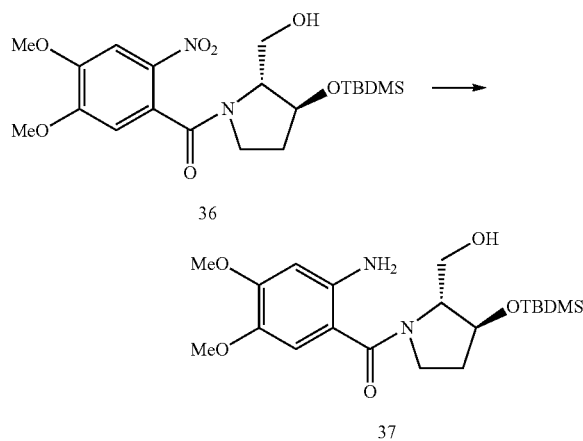

To a solution of ((2R,3S)-3-((tert-butyldimethylsilyl)oxy)-2-(hydroxymethyl)-pyrrolidin-1-yl)(4,5-dimethoxy-2-nitrophenyl)methanone (36) (1.8 g, 3.8 mmol) in ethanol (24 mL) and ethyl acetate (6 mL) was added palladium on activated charcoal (10% wt. basis) (180 mg). The reaction mixture was hydrogenated at 35 psi for 3 h in a Parr apparatus. The reaction mixture was filtered through celite and the resulting cake was washed with ethyl acetate. The filtrate was concentrated in vacuo to give the title compound (1.4 g, 90%) as a pink solid. The resulting material was carried through to the next step without any further purification.

MS (ES+): m/z=411 (M+H)+; LCMS: $t_R$=7.10 mins.

Example 16: Allyl (24(2R,3S)-3-((tert-butyldimethylsilyl)oxy)-2-(hydroxyl-methyl)-pyrrolidine-1-carbonyl)-4,5-dimethoxyphenyl)carbamate (38)

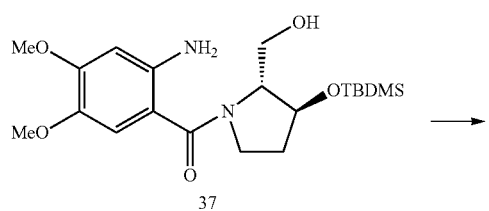

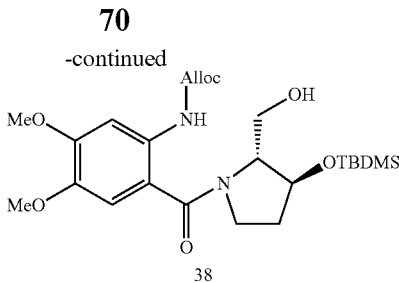

To a solution of (2-amino-4,5-dimethoxyphenyl)((2R, 3S)-3-((tert-butyldimethyl-silyl)oxy)-2-(hydroxymethyl) pyrrolidin-1-yl)methanone (37) (1.4 g, 3.4 mmol) and pyridine (635 μL, 7.8 mmol) in anhydrous dichloromethane (30 mL) at −10° C., a solution of allylchloroformate (380 μL, 3.6 mmol) in dichloromethane (10 mL) was added dropwise. The reaction mixture was then stirred at room temperature for 30 mins. This was then sequentially washed with a saturated aqueous solution of copper (II) sulfate (20 mL), water (20 mL) and a saturated aqueous solution of sodium hydrogen carbonate (20 mL). The organic layer was then dried over sodium sulfate, filtered and concentrated to give the title compound (1.5 g, 89%) as a pink oil. The resulting material was carried through to the next step without any further purification.

MS (ES+): m/z=495 (M+H)+; LCMS: $t_R$=8.03 mins.

Example 17: Allyl (1S)-1-((tert-butyldimethylsilyl)oxy)-11-hydroxy-7,8-dimethoxy-5-oxo-2,3,11,11a-tetrahydro-1H-benzo[e]pyrrolo[1,2-a][1,4]diazepine-10 (5H)-carboxylate (39)

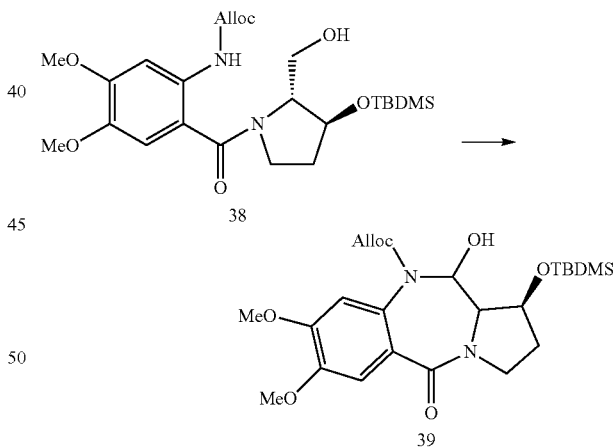

To a solution of allyl (2-((2R,3S)-3-((tert-butyldimethylsilyl)oxy)-2-(hydroxymethyl)-pyrrolidine-1-carbonyl)-4,5-dimethoxyphenyl)carbamate (38) (1.5 g, 3.0 mmol) in dichloromethane (30 mL) was added TEMPO (48 mg, 0.30 mmol) and (diacetoxyiodo)benzene (1.17 g, 3.6 mmol). The reaction mixture was stirred at room temperature for 16 h, and was then sequentially washed with a saturated aqueous solution of sodium metabisulfite (20 mL), a saturated aqueous solution of sodium hydrogen carbonate (20 mL), water (20 mL) and brine (20 mL). The organic layer was then dried over sodium sulfate, filtered and concentrated. The resulting residue was purified by column chromatography (silica), eluting with methanol/dichloromethane (from 0% to 50%), to give the title compound (1.0 g, 54%) as a cream solid.

MS (ES+): m/z=493 (M+H)⁺; LCMS: $t_R$=7.57 mins.

Example 18: Allyl (1S,11aS)-1-((tert-butyldimethylsilyl)oxy)-7,8-dimethoxy-5-oxo-11-((tetrahydro-2H-pyran-2-yl)oxy)-2,3,11,11a-tetrahydro-1H-benzo[e]pyrrolo [1,2-a][1,4]diazepine-10 (5H)-carboxylate (40)

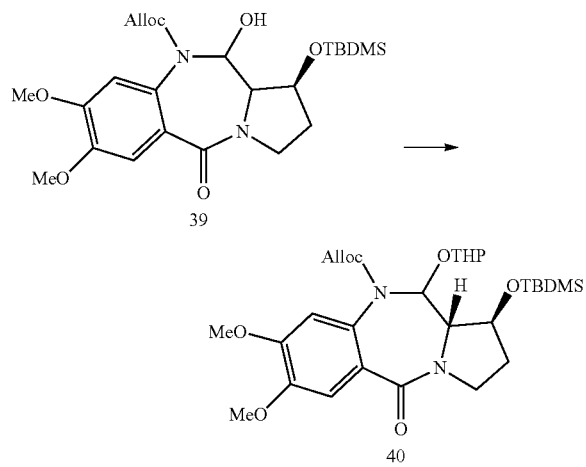

A mixture of allyl (1S)-1-((tert-butyldimethylsilyl)oxy)-11-hydroxy-7,8-dimethoxy-5-oxo-2,3,11,11a-tetrahydro-1H-benzo[e]pyrrolo[1,2-a][1,4]diazepine-10(51-1)-carboxylate (39) (to g, 1.7 mmol), 3,4-dihydro-2H-pyran (1.5 mL, 16.5 mmol) and pTSA (10 mg, 1% w/w) in ethyl acetate (20 mL) was stirred at room temperature for 16 h. The reaction mixture was then diluted with ethyl acetate (50 mL) and washed with a saturated aqueous solution of sodium hydrogen carbonate (20 mL) and brine (30 mL). The organic layer was dried over sodium sulfate, filtered and concentrated to give the title compound (1.0 g, 99%) as a yellow gum. The resulting material was carried through to the next step without any further purification.

MS (ES+): m/z=577 (M+H)⁺; LCMS: $t_R$=8.98 mins.

Example 19: Allyl (1S,11aS)-1-hydroxy-7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (41)

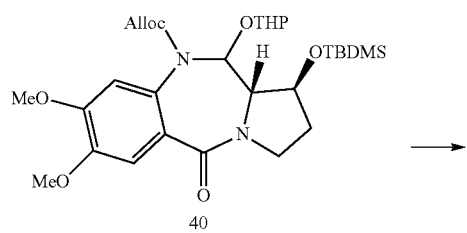

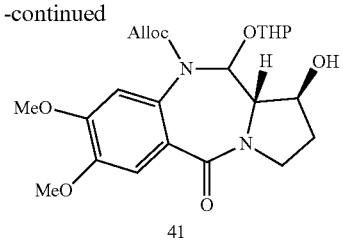

To solution of allyl (1S,11aS)-1-((tert-butyldimethylsilyl)oxy)-7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (40) (1.0 g, 1.65 mmol) in anhydrous tetrahydrofuran (20 mL) at 0° C. was added tetrabutylammonium fluoride (1 M in THF) (2.5 mL, 2.5 mmol). The reaction mixture was stirred at room temperature for 2 h. The reaction mixture was concentrated in vacuo and the residue was diluted with water (30 mL) and extracted with ethyl acetate (3×50 mL). The organic layer was then washed with brine (50 mL), dried over sodium sulfate, filtered and concentrated. The resulting residue was purified by column chromatography (silica), eluting with methanol/dichloromethane (from 0% to 10%), to give the title compound (840 mg, 98%) as a cream solid.

MS (ES+): m/z=463 (M+H)⁺; LCMS: $t_R$=6.13 mins.

Example 20: (1S,11aR)-1-Hydroxy-7,8-dimethoxy-1,2,3,11a-tetrahydro-5H-benzo[e]pyrrolo[1,2-a][1,4]diazepin-5-one (42)

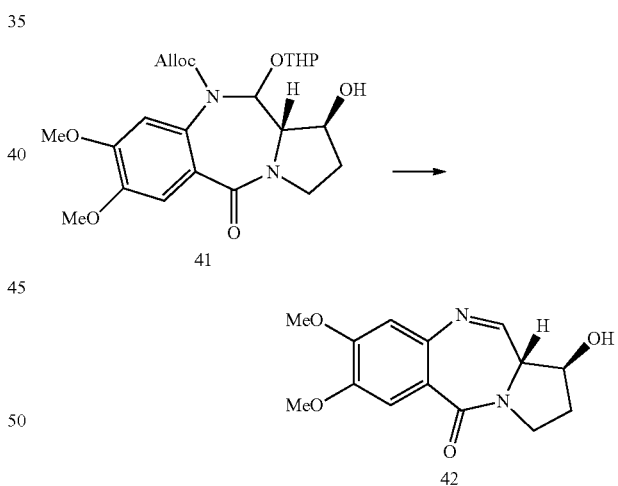

To a solution of allyl (1S,11aS)-1-hydroxy-7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10 (5-H)-carboxylate (41) (50 mg, 0.070 mmol) in dichloromethane (2 mL) was added tetrakis(triphenylphosphine)palladium(0) (4.1 mg, 5 mol %), triphenylphosphine (4.6 mg, 25 mol %) and pyrrolidine (7 µL, 0.09 mmol). The reaction mixture was stirred at room temperature for 30 mins. and then subjected to high vacuum for 2 h until excess pyrrolidine was thoroughly removed. The resulting residue was then purified by column chromatography (silica), eluting with acetone/dichloromethane (from 0% to 100%), to give the title compound (13 mg, 67%) as a pale brown solid. 1H NMR (400 MHz, CDCl$_3$) δ 7.67 (d, J=4.5 Hz, 1H) 7.47 (s, 1H) 6.81 (s, 1H) 4.77 (br s, 1H) 3.94 (s, 3H) 3.92-3.94 (m, 3H) 3.72-3.91 (m, 4H) 3.64 (d, J=4.5 Hz, 1H) 1.25 (s, 1H); $^{13}$C NMR (100 MHz, CDCl$_3$) δ 164.7, 159.2, 151.4, 147.7, 140.5, 120.1, 111.3, 109.5, 74.6, 62.2, 56.2, 44.6, 33.1, 31.0.

Example 21: Allyl (1S,11aS)-1-(2-ethoxy-2-oxoethoxy)-7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (43)

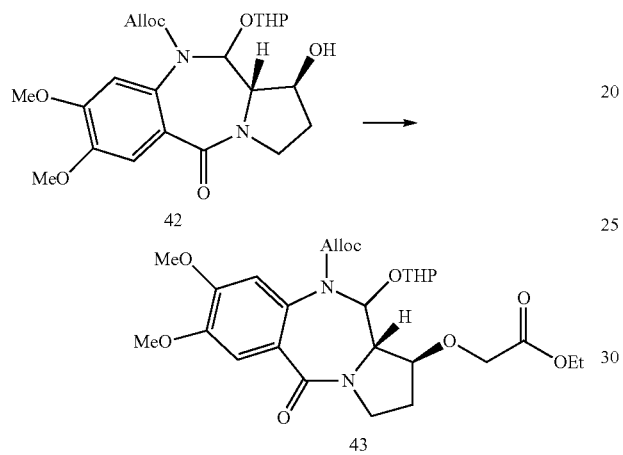

To a solution of allyl (1S,11aS)-1-hydroxy-7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (42) (150 mg, 0.32 mmol) in anhydrous dichloromethane (3 mL) was added rhodium(II) acetate dimer (15 mg, 0.034 mmol) and ethyl diazoacetate (370 μL, 2.82 mmol). The reaction mixture was stirred at room temperature for 30 mins. which was then diluted with diethyl ether (30 mL) and filtered through celite. The cake was then washed with diethyl ether. The filtrate was concentrated in vacuo to give the title compound (180 mg, 99%) as a green oil. The resulting material was carried through to the next step without any further purification.

MS (ES+): m/z=$_5$49 (M+H)$^+$; LCMS: t$_R$=7.18 mins.

Example 22: 2-(((1S,11aS)-10-((Allyloxy)carbonyl)-7,8-dimethoxy-5-oxo-11-((tetrahydro-2H-pyran-2-yl)oxy)-2,3,5,10,11,11a-hexahydro-1H-benzo[e]pyrrolo[1,2-a][1,4]diazepin-1-yl)oxy)acetic acid (44)

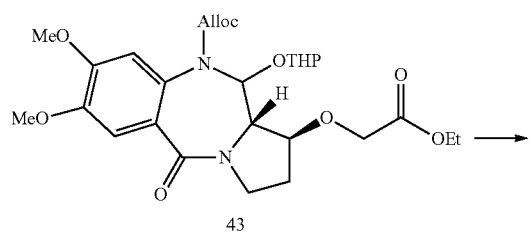

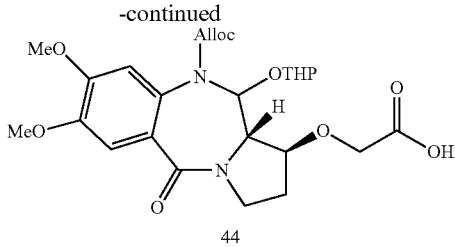

To a solution of allyl (1S,11aS)-1-(2-ethoxy-2-oxoethoxy)-7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (43) (180 mg, 0.328 mmol) in 1,4-dioxane (2.5 mL) was added a 0.5 M aqueous solution of sodium hydroxide (2.5 mL, 1.25 mmol). The reaction mixture was stirred at room temperature for 2 h and was then concentrated in vacuo, after which water (20 mL) was added and the aqueous layer was acidified to pH=1 with a 1 M citric acid solution (5 mL). The aqueous layer was then extracted with ethyl acetate (2×50 mL). The combined organic extracts were then washed with brine (50 mL), dried over sodium sulfate, filtered and concentrated to give the title compound (170 mg, 99%) as a yellow oil. The resulting material was carried through to the next step without any further purification.

MS (ES+): m/z=521 (M+H)$^+$; LCMS: t$_R$=6.22 mins.

Example 23: Methyl 4-(4-aminophenyl)-1-methyl-1H-pyrrole-2-carboxylate (45)

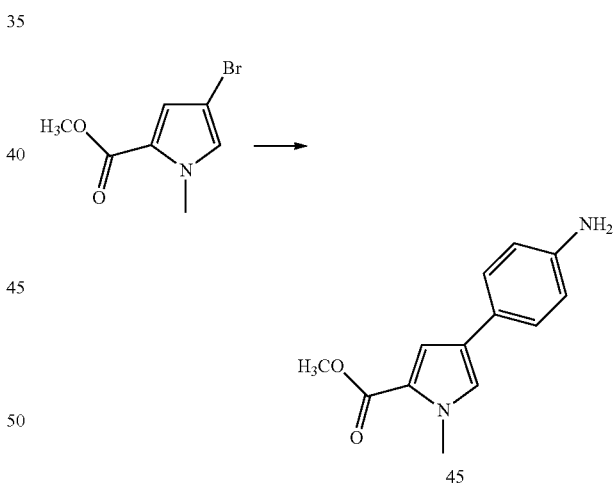

A mixture of methyl 4-bromo-1-methyl-1H-pyrrole-2-carboxylate (750 mg, 3.44 mmol), 4-(4,4,5,5-tetramethyl-1,3,2-dioxaborolan-2-yl)aniline (905 mg, 4.13 mmol) and potassium carbonate (1.43 g, 10.3 mmol) in toluene/ethanol/water (9:3:1) (13 mL total) was degassed with nitrogen for 5 mins. Tetrakis(triphenylphosphine)palladium(0) (230 mg, 6 mol %) was then charged and the reaction mixture was irradiated with microwaves at 100° C. for 15 mins. Water (10 mL) was then added to the reaction mixture, which was extracted with ethyl acetate (3×40 mL). The combined organic extracts were then dried over sodium sulfate, filtered and concentrated. The resulting residue was purified by column chromatography (silica), eluting with ethyl acetate/ hexanes (from 0% to 50%), to give the title compound (145 mg, 18%) as a yellow solid.

MS (ES+): m/z=231 (M+H)$^+$; LCMS: $t_R$=5.17 mins.

Example 24: Methyl 4-(4-(4-((tert-butoxycarbonyl)amino)-1-methyl-1H-imidazole-2-carboxamido)phenyl)-1-methyl-1H-pyrrole-2-carboxylate (46)

purified by column chromatography (silica), eluting with ethyl acetate/dichloromethane (from 0% to 50%), to give the title compound (36 mg, 45%) as a yellow oil.

MS (ES+): m/z=454 (M+H)$^+$; LCMS: $t_R$=8.08 mins.

Example 25: Methyl 4-(4-(4-amino-1-methyl-1H-imidazole-2-carbox-amido)phenyl)-1-methyl-1H-pyrrole-2-carboxylate hydrochloride (47)

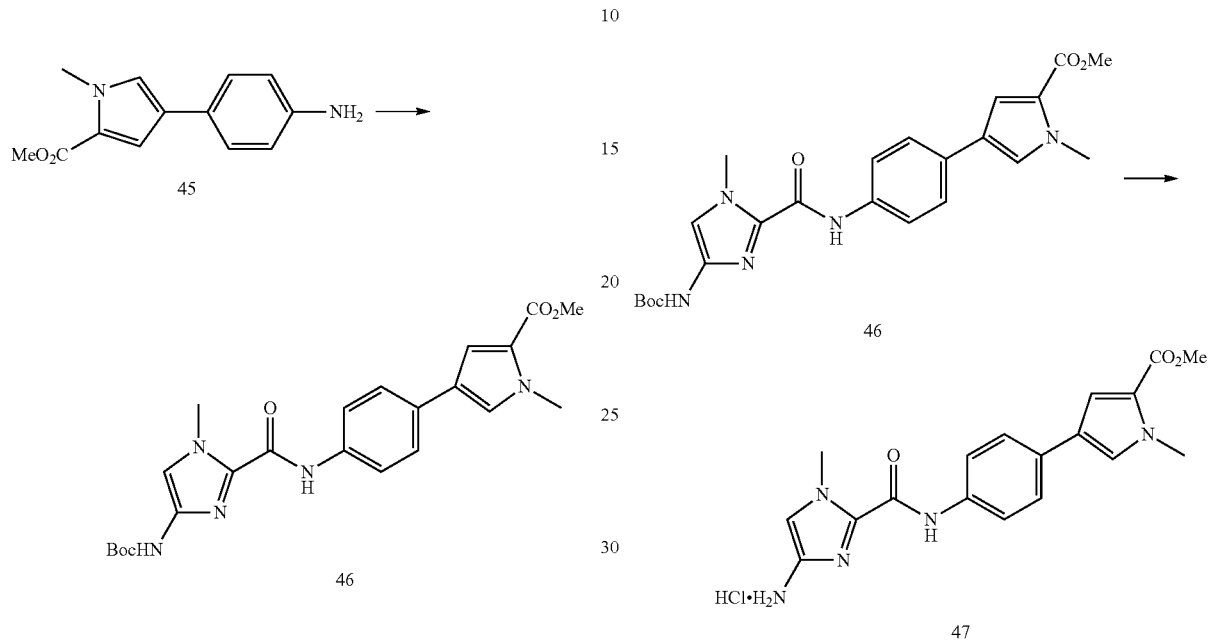

To a solution of 4-((tert-butoxycarbonyl)amino)-1-methyl-1H-imidazole-2-carboxylic acid (59 mg, 0.23 mmol) in N,N-dimethylformamide (4 mL) was added 1-(3-dimethylaminopropyl)-3-ethylcarbodiimide hydrochloride (67 mg, 0.36 mmol) and 4-(dimethylamino)pyridine (65 mg, 0.53 mmol). The reaction mixture was stirred at room temperature for 2 h. Methyl 4-(4-aminophenyl)-1-methyl-1H-pyrrole-2-carboxylate (45) (41 mg, 0.18 mmol) was added to the reaction mixture which was then stirred at room temperature for 16 h. The reaction mixture was poured into ice-water (40 mL) and extracted with ethyl acetate (3×100 mL). The combined organic layer was sequentially washed with 1 M citric acid (60 mL), a saturated aqueous solution of sodium hydrogen carbonate (70 mL), water (70 mL) and brine (70 mL). The organic layer was dried over sodium sulfate, filtered and concentrated. The resulting residue was Methyl 4-(4-(4-((tert-butoxycarbonyl)amino)-1-methyl-1H-imidazole-2-carboxamido)phenyl)-1-methyl-1H-pyrrole-2-carboxylate (46) (36 mg, 0.079 mmol) was dissolved in hydrochloric acid (4 M in dioxane) (5 mL) and the reaction mixture was stirred at room temperature for 2 h. The reaction mixture was concentrated in vacuo to give the title compound (30 mg, 97%) as a yellow solid. The resulting material was carried through to the next step without any further purification.

MS (ES+): m/z=354 (M+H)$^+$; LCMS: $t_R$=6.10 mins.

Example 26: Allyl (1S,11aS)-7,8-dimethoxy-1-(2-((2-((4-(5-(methoxycarbonyl)-1-methyl-1H-pyrrol-3-yl)phenyl)carbamoyl)-1-methyl-1H-imidazol-4-yl)amino)-2-oxoethoxy)-5-oxo-11-(tetrahydro-2H-pyran-2-yl)oxy)-2,3,11,11a-tetrahydro-1H-benzo[e]pyrrolo[1,2-a][1,4]diazepine-10 (5H)-carboxylate (48)

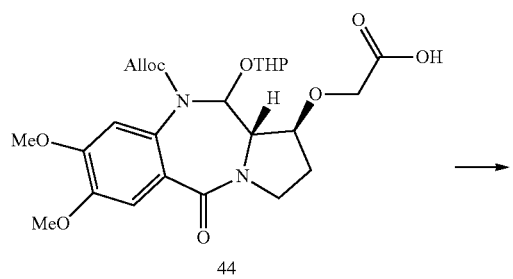

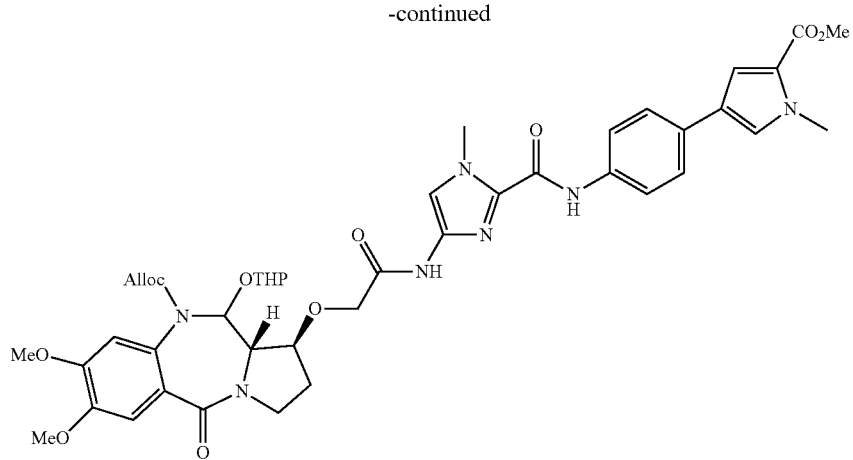

48

A solution of 2-(((1S,11aS)-10-((allyloxy)carbonyl)-7,8-dimethoxy-5-oxo-11-((tetrahydro-2H-pyran-2-yl)oxy)-2,3,5,10,11,11a-hexahydro-1H-benzo[e]pyrrolo[1,2-a][1,4]diazepin-1-yl)oxy)acetic acid (44) (170 mg, 0.328 mmol) in N,N-dimethylformamide (2 mL) was charged with 1-(3-dimethylaminopropyl)-3-ethylcarbodiimide hydrochloride (126 mg, 0.657 mmol) and 4-(dimethylamino)-pyridine (100 mg, 0.818 mmol). The reaction mixture was stirred at room temperature for 2 h. Methyl 4-(4-(4-amino-1-methyl-1H-imidazole-2-carboxamido)phenyl)-1-methyl-1H-pyrrole-2-carboxylate hydrochloride (47) (30 mg, 0.077 mmol) was then added and the resulting mixture was stirred at room temperature for 16 h. This was then poured into ice-water (20 mL) and extracted with ethyl acetate (3×50 mL). The combined organic extracts were sequentially washed with 1 M citric acid (30 mL), a saturated aqueous solution of sodium hydrogen carbonate (35 mL), water (35 mL) and brine (35 mL). The organic layer was then dried over sodium sulfate, filtered and concentrated. The resulting residue was purified by column chromatography (silica), eluting with acetone/dichloromethane (from 0% to 50%), to give the title compound (37 mg, 56%) as a yellow gum.

$^1$H NMR (CDCl$_3$, 400 MHz) δ 9.06 (br s, 1H), 8.42 (d, 1H, J=5.7 Hz), 7.68 (d, 2H, J=8.4 Hz), 7.49 (d, 2H, J=8.4 Hz), 7.43 (s, 1H), 7.21 (d, 1H, J=2.0 Hz), 7.09 (d, 1H, J=2.0 Hz), 6.93 (s, 1H), 6.58 (s, 1H), 5.91-5.66 (m, 2H), 5.23-4.97 (m, 2H), 4.75-4.56 (m, 1H), 4.50-4.29 (m, 2H), 4.18-4.11 (m, 1H), 4.09 (s, 3H), 3.98 (s, 3H), 3.96-3.88 (m, 7H), 3.86 (s, 3H), 3.71 (s, 6H), 2.37-2.23 (m, 2H), 1.87-1.67 (m, 4H), 1.65-1.58 (m, 2H);

MS (ES+): m/z=856 (M+H)$^+$; LCMS: t$_R$=7.83 mins.

Example 27: Methyl 4-(4-(4-(2-(((1S,11aR)-7,8-dimethoxy-5-oxo-2,3,5,11a-tetrahydro-1H-benzo[e]pyrrolo[1,2-a][1,4]diazepin-1-yl)oxy)acetamido)-1-methyl-1H-imidazole-2-carboxamido)phenyl)-1-methyl-1H-pyrrole-2-carboxylate (49)

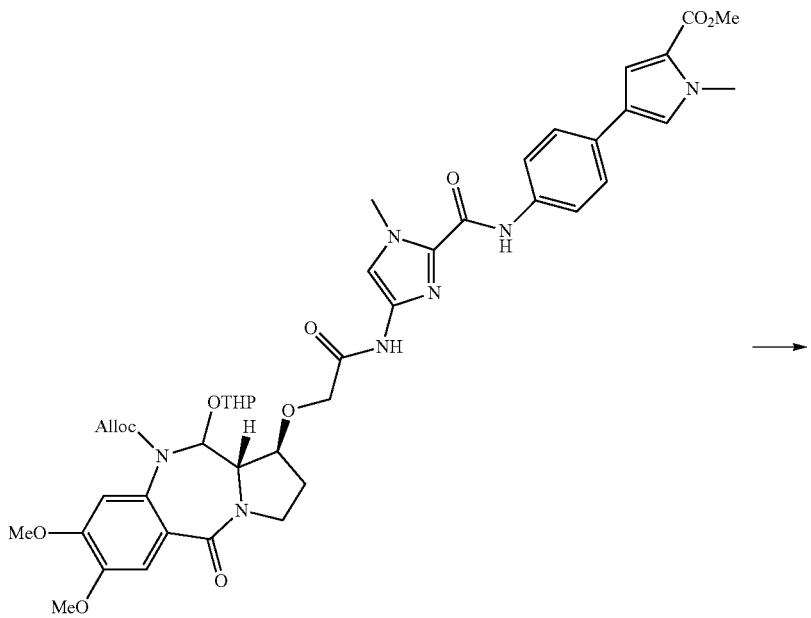

48

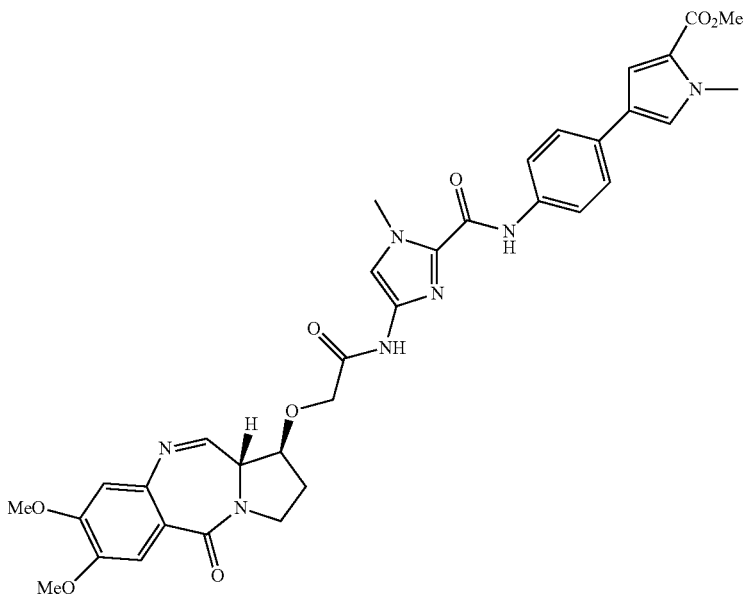

49

To a solution of allyl (1S,11aS)-7,8-dimethoxy-1-(2-(2-(4-(5-(methoxycarbonyl)-1-methyl-1H-pyrrol-3-yl)phenyl)carbamoyl)-1-methyl-1H-imidazol-4-yl)amino)-2-oxoethoxy)-5-oxo-11-((tetrahydro-2H-pyran-2-yl)oxy)-2,3,11,11a-tetrahydro-1H-benzo[e]pyrrolo[1,2-a][1,4]diazepine-10(5-H)-carboxylate (48) (37 mg, 0.043 mmol) in dichloromethane (2 mL) was added tetrakis(triphenylphosphine)palladium(0) (2.5 mg, 5 mol %), triphenylphosphine (2.8 mg, 25 mol %) and pyrrolidine (4.5 µL, 0.055 mmol). The reaction mixture was stirred at room temperature for 30 mins. The reaction mixture was subjected to high vacuum for 30 mins. until excess pyrrolidine was thoroughly removed. The resulting residue was then purified by column chromatography (silica), eluting with acetone/dichloromethane (from 0% to 100%) followed by methanol, to give the title compound (15 mg, 52%) as a yellow oil. 1H NMR (CDCl$_3$, 400 MHz) δ 8.91 (br s, 1H), 7.94 (br s, 1H), 7.64 (d, 1H, J=4.5 Hz), 7.50 (s, 1H), 7.43-7.38 (m, 3H), 7.37 (d, 2H, J=8.4 Hz), 7.11 (d, 1H, J=1.6 Hz), 6.99 (d, 1H, J=1.6 Hz), 6.78 (s, 1H), 4.85-4.67 (m, 1H), 4.50-4.42 (m, 1H), 4.14 (d, 1H, J=14.7 Hz), 4.01 (d, 1H, J=14.7 Hz), 3.90 (s, 3H), 3.89 (s, 3H), 3.88 (s, 3H), 3.87 (s, 3H), 3.77 (s, 3H), 3.58 (d, 1H, J=3.9 Hz), 3.53 (br, 1H), 2.30 (dd, 1H, J=13.4, 5.9), 2.21-2.12 (m, 1H); MS (ES+): m/z=670 (M+H)$^+$; LCMS: t$_R$=6.80 mins.

Example 28: Diallyl 1,1'-(propane-1,3-diylbis(oxy))(1S,1'S)-bis(7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (50)

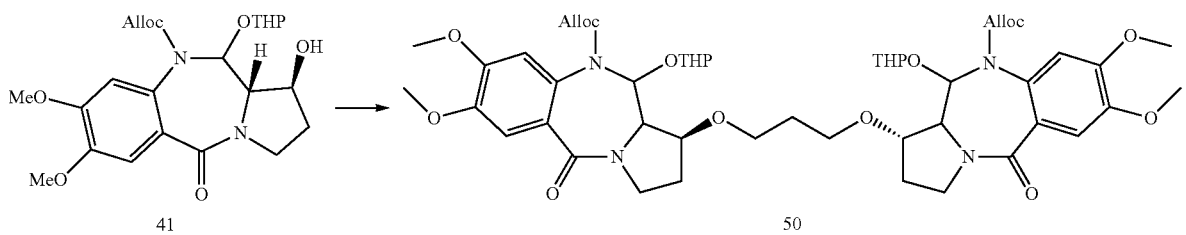

In an oven-dried 10 mL pear-shaped flask (pre-evacuated and flushed with nitrogen), a solution of allyl (1S)-1-hydroxy-7,8-dimethoxy-5-oxo-11-(tetrahydro-2H-pyran-2-yl)oxy)-2,3,11,11a-tetrahydro-1-H-benzo[e]pyrrolo[1,2-a][1,4]diazepine-10(5-H)-carboxylate (41) (50 mg, 0.108 mmol) in anhydrous tetrahydrofuran (2 mL) was cooled to 0° C. and charged with sodium hydride (60% dispersion in mineral oil) (9.5 mg, 0.476 mmol) and stirred at this temperature under nitrogen for 5 mins. A solution of 1,3-propanediol di-p-tosylate (21 mg, 0.054 mmol) in anhydrous tetrahydrofuran (1 mL) was subsequently added dropwise to the reaction mixture (over 5 mins.) before allowing the mixture to warm to room temperature and stirring overnight. After quenching with a saturated aqueous solution of sodium hydrogen carbonate (5 mL) and charging ethyl acetate (5 mL), the mixture was separated and the organic phase extracted twice with ethyl acetate. The combined organic extracts were then dried over anhydrous magnesium sulfate and concentrated in vacuo. The resulting residue was then purified by column chromatography (silica), eluting with hexanes/ethyl acetate (10:1), then ethyl acetate and then finally with ethyl acetate/methanol (4:1) to give the title compound (3 mg, 6%) as a yellow oil.

$^1$H NMR (CDCl$_3$, 400 MHz) δ 7.16 (s, 2H), 6.81 (s, 2H), 5.77-5.67 (m, 2H), 5.66-5.57 (m, 2H), 5.10-5.03 (m, 4H), 5.02-4.90 (m, 4H), 4.65-4.49 (m, 2H), 4.41-4.25 (m, 2H), 3.87 (s, 6H), 3.80 (s, 6H), 3.72-3.63 (m, 4H), 3.59-3.45 (m, 4H), 3.40-3.24 (m, 6H), 2.05-1.99 (m, 4H), 1.56-1.36 (m, 14H); MS (ES+): m/z=987.6 (M+Na)$^+$; LCMS: $t_R$=7.18 mins.

Example 29: (1S,1'S)-1,1'-(Propane-1,3-diylbis(oxy))bis(7,8-dimethoxy-1,2,3,11a-tetrahydro-5H-benzo[e]pyrrolo [1,2-a][1,4]diazepin-5-one) (51)

romethane, followed by dichloromethane/acetone to give the title compound (1.9 mg, 100%).

$^1$H NMR (CDCl$_3$, 400 MHz) δ 7.58 (d, 2H, J=4.5 Hz), 7.45 (s, 2H), 6.75 (s, 2H), 4.23 (br, 2H), 3.90 (s, 6H), 3.86 (s, 6H), 3.85-3.77 (m, 4H), 3.65-3.55 (m, 2H), 3.43-3.33 (m, 4H), 2.06-1.94 (m, 4H), 1.79-1.44 (m, 2H); $^{13}$C NMR δ 164.5, 159.0, 151.4, 147.7, 140.4, 120.1, 111.4, 109.6, 82.1, 59.7, 56.2, 56.1, 53.8, 44.6, 31.8, 29.3; MS (ES+): m/z=592.8 (M+H)$^+$; LCMS: $t_R$=5.23 mins.

Example 30: Evidence of DNA Adduct Formation by HPLC

The interactions of C1-linked PBD core compound (42), C1-linked PBD core compound (42) and C1-linked PBD dimer compound (51) were studied with duplex transcription factor consensus sequences. For the C1-linked PBD core compound (42) and C1-linked PBD dimer compound (51) the study used a STAT3 consensus sequence (5'-GACATTGC-3'). Whereas for the C1-linked PBD monomer compound (49), an NF-KB consensus sequence (5'-GGGACAGCCC-3') was used in the study. The interactions of each of the three compounds were studied with an HPLC assay utilizing a X-bridge MS C18 2.5 μM Oligonucleotide Separation Technology (OST) column (2.3×50 mm) and a gra-

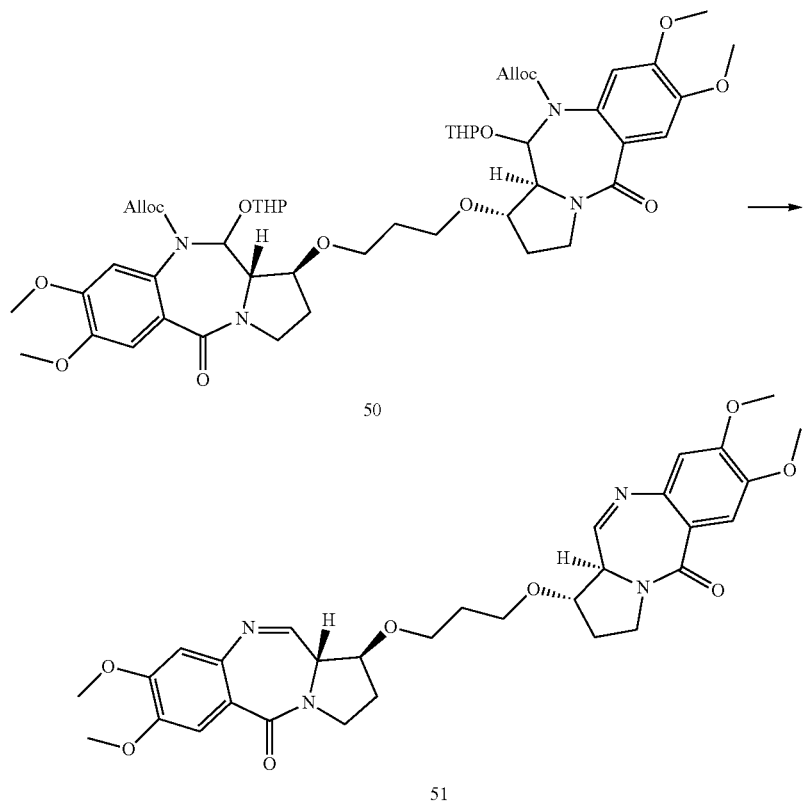

50

51

Figure 7:
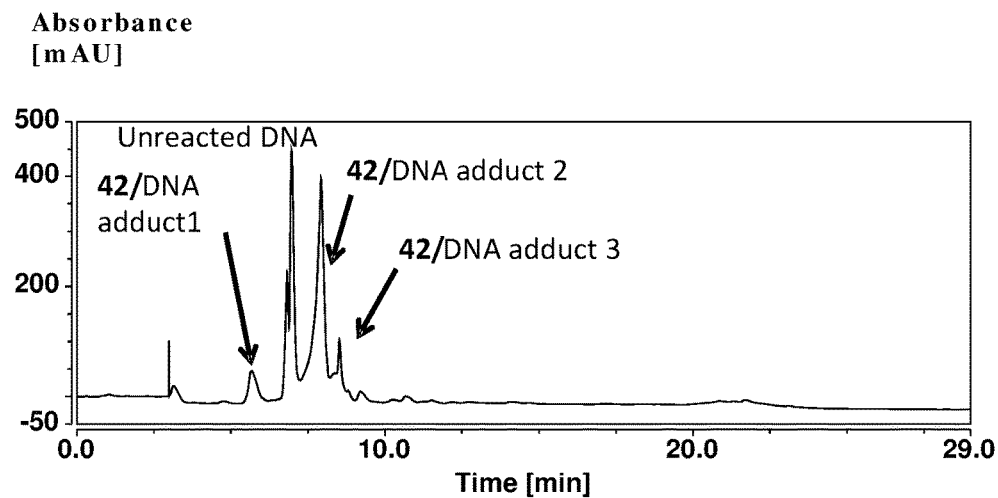
FIG. 7: Shows a chromatogram from an HPLC assay that provides evidence of DNA adduct formation with a C1-linked PBD core compound (42)
Figure 8:
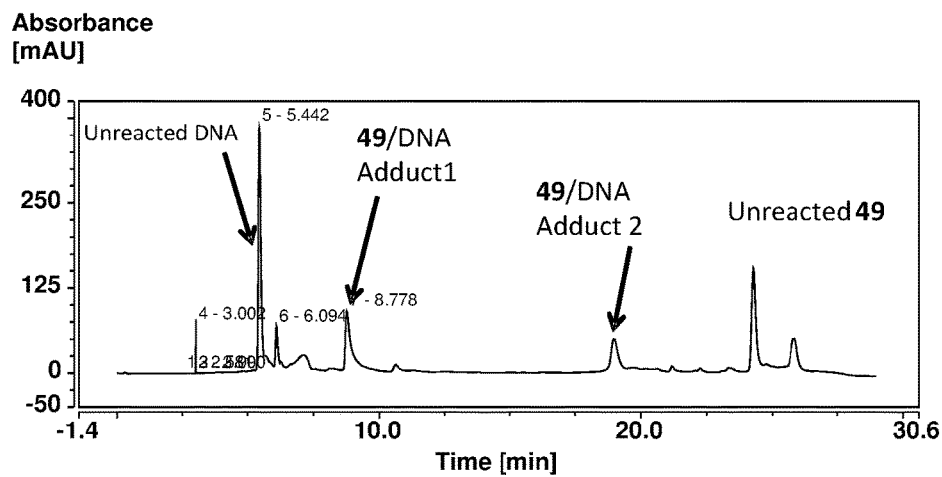
FIG. 8: Shows a chromatogram from an HPLC assay that provides evidence of DNA adduct formation with a C1-linked PBD monomer (49)
Figure 9:
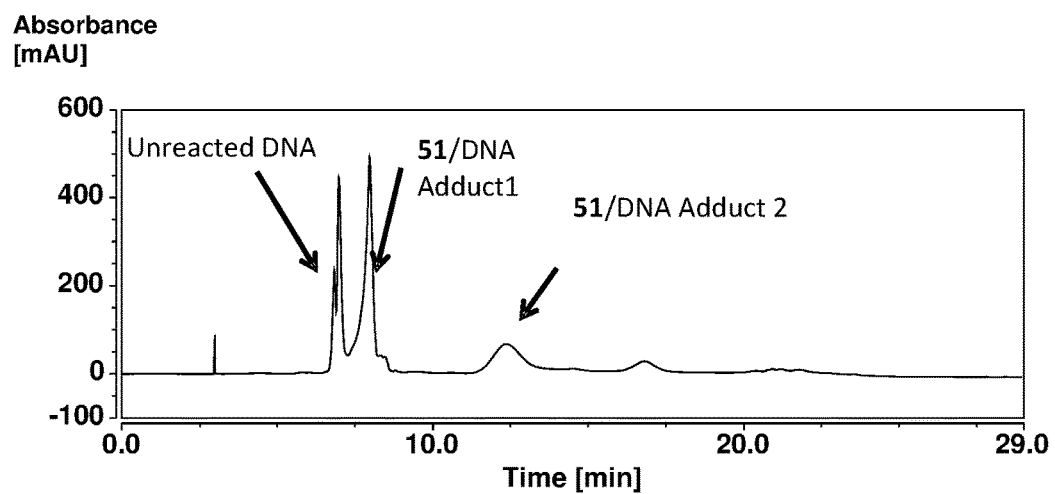
FIG. 9: Shows a chromatogram from an HPLC assay that provides evidence of DNA adduct formation with a C1-linked PBD dimer (51)

A solution of diallyl 1,1'-(propane-1,3-diylbis(oxy))(1S,1'S)-bis(7,8-dimethoxy-5-oxo-11-((tetrahydro-2H-pyran-2-yl)oxy)-2,3,11,11a-tetrahydro-1H-benzo[e]pyrrolo[1,2-a][1,4]diazepine-10(5-H)-carboxylate) (50) (3 mg, 0.0031 mmol) in dichloromethane (1 mL) was charged with tetrakis(triphenylphosphine)palladium(0) (1 mg), triphenylphosphine (1 mg) and pyrrolidine (1 μL) and stirred at room temperature in a vial for 30 mins. The reaction mixture was subsequently filtered through celite and concentrated in vacuo. After subjecting to high vacuum for 2 hours, the residue was purified by chromatography (silica), eluting with dichlodient of 40% acetonitrile/water and 100 mM TEAB (Tetraethylammonium bromide)/water as mobile phase with a flow rate of 0.5 mL/min and UV detection at 254 nm. A 4:1 molar ratio of ligand:oligonucleotide was used, with each single-stranded oligonucleotide dissolved in 1M ammonium acetate to form stock solutions of 1 mM. The oligonucleotides were initially annealed by heating their 1 mM solutions to 70° C. for 10 mins followed by gradual cooling over 8 hours and storage overnight at −20° C. Working solutions of oligonucleotides of 25 μM were then prepared by diluting the annealed stock solutions with 100 mM ammonium acetate. The ligands were dissolved in DMSO to form a stock solution of 10 mM which was stored at −20° C. for no longer than four months. Working solutions of the drug of 100 μM were prepared by diluting the stock solution with 100 mM ammonium acetate. The working solutions of the ligands were added to the working solution the oligonucleotides at RT, and the mixture incubated for different time intervals at room temperature. The chromatograms from the HPLC assay show that each of the C1-linked PBD core (42), monomer (49) and dimer (51) compounds interacted with the DNA consensus sequence to form adducts. The chromatograms for HPLC assays using C1-linked PBD core (42), monomer (49) and dimer (51) compounds are shown in FIGS. 7, 8 and 9 respectively.

Example 31: Cytotoxicity Analysis of C1-Linked PBD Monomer and Dimer by MTT Assay Cell Culture MDA MB231 (triple negative human breast cancer) was obtained from the American Type Culture Collection. The cell-line was maintained in monolayer culture in 75 cm$^2$ flasks (TPP, Switzerland) under a humidified 5% $CO_2$ atmosphere at 37° C. The MDA MB231 cell line was maintained in high glucose (Dulbecco's Modified Eagle Medium) DMEM (4.5 g\l; Invitrogen), foetal bovine serum (10%, Biosera UK), non-essential amino acids (ix; Invitrogen), L-glutamine (2 mM; Invitrogen) and Penicillin-Streptomycin (1% v/v, Invitrogen). For passaging, cells were washed with PBS [Phosphate-Buffered Saline] (GIBCO 14040, Invitrogen, UK), incubated with trypsine (GIBCO 25300, Invitrogen, UK), and re-seeded into fresh medium. For seeding, cells were counted using a Neubauer haemocytometer (Assistant, Germany) by microscopy (Nikon, USA) on a non-adherent suspension of cells that were washed in PBS, trypsinised, centrifuged at 8° C. at 8000 rpm for 5 min and re-suspended in fresh medium.

MTT Assay

The cells were grown in normal cell culture conditions at 37° C. under a 5% $CO_2$ humidified atmosphere using appropriate medium. The cell count was adjusted to $10^5$ cells/ml and 5,000-20,000 cells were added per well depending on the cell line. The cells were incubated for 24 hours and 1 μl of the appropriate inhibitor concentrations were added to the wells in triplicates. After 72 h of continuous exposure to each compound, the cytotoxicity was determined using the 3-(4,5-Dimethylthiazol-2-yl)-2,5-diphenyltetrazolium bromide (MTT) (Lancaster Synthesis Ltd, UK) colorimetric assay. Absorbance was quantified by spectrophotometry at $\lambda$=570 nm (Envision Plate Reader, PerkinElmer, USA). $IC_{50}$ values were calculated by a dose-response analysis using the Prism GraphPad Prism® software. The cytotoxicity results are shown below in Table 2.

TABLE 2

$IC_{50}$ values (nM) determined after 72 hours exposure for the $C_1$-linked PBD monomer (49) and dimer (51)
$IC_{50}$ (nanomolar)

| Compound | MDA MB 231 (Triple negative breast cancer cell line) |
|---|---|
| 49 | 36 ± 2.3 |
| 51 | 236 ± 27 |

REFERENCES

1. Antonow, D., and Thurston, D. E. (2011) *Chem Rev* 111, 2815-2864.
2. Cipolla, L., Araujo, A. C., Airoldi, C., and Bini, D. (2009) *Anticancer Agents Med Chem* 9, 1-31.
3. Gerratana, B. (2012) *Med Res Rev* 32, 254-293.
4. Hartley, J. A. (2011) *Expert Opin Investig Drugs* 20, 733-744.
5. Kamal, A., Reddy, K. L., Devaiah, V., Shankaraiah, N., and Reddy, D. R. (2006) *Mini Rev Med Chem* 6, 53-69.
6. Hurley, L. H., Reck, T., Thurston, D. E., Langley, D. R., Holden, K. G., Hertzberg, R. P., Hoover, J. R., Gallagher, G., Jr., Faucette, L. F., Mong, S. M., (1988) *Chem Res Toxicol* 1, 258-268.
7. Wells, G., Martin, C. R., Howard, P. W., Sands, Z. A., Laughton, C. A., Tiberghien, A., Woo, C. K., Masterson, L. A., Stephenson, M. J., Hartley, J. A., Jenkins, T. C., Shnyder, S. D., Loadman, P. M., Waring, M. J., and Thurston, D. E. (2006) *J Med Chem* 49, 5442-5461.
8. Brucoli, F., Hawkins, R. M., James, C. H., Jackson, P. J., Wells, G., Jenkins, T. C., Ellis, T., Kotecha, M., Hochhauser, D., Hartley, J. A., Howard, P. W., and Thurston, D. E. (2013) *J Med Chem* 56, 6339-6351.
9. Kotecha, M., Kluza, J., Wells, G., O'Hare, C. C., Forni, C., Mantovani, R., Howard, P. W., Morris, P., Thurston, D. E., Hartley, J. A., and Hochhauser, D. (2008) *Mol Cancer Ther* 7, 1319-1328.
10. Puvvada, M. S., Hartley, J. A., Jenkins, T. C., and Thurston, D. E. (1993) *Nucleic Acids Res* 21, 3671-3675.
11. Clingen, P. H., De Silva, I. U., McHugh, P. J., Ghadessy, F. J., Tilby, M. J., Thurston, D. E., and Hartley, J. A. (2005) *Nucleic Acids Res* 33, 3283-3291.
12. Puvvada, M. S., Forrow, S. A., Hartley, J. A., Stephenson, P., Gibson, I., Jenkins, T. C., and Thurston, D. E. (1997) *Biochemistry* 36, 2478-2484.
13. Barkley, M. D., Cheatham, S., Thurston, D. E., and Hurley, L. H. (1986) *Biochemistry* 25, 3021-3031.
14. Seifert, J., Pezeshki, S., Kamal, A., and Weisz, K. (2012) *Organic & Biomolecular Chemistry* 10, 6850-6860.
15. Smellie, M., Bose, D. S., Thompson, A. S., Jenkins, T. C., Hartley, J. A., and Thurston, D. E. (2003) *Biochemistry* 42, 8232-8239.
16. Kopka, M. L., Goodsell, D. S., Baikalov, I., Grzeskowiak, K., Cascio, D., and Dickerson, R. E. (1994) *Biochemistry* 33, 13593-13610.
17. Kizu, R., Draves, P. H., and Hurley, L. H. (1993) *Biochemistry* 32, 8712-8722.
18. Leimgruber, W., Stefanovic, V., Schenker, F., Karr, A., and Berger, J. (1965) *J Am Chem Soc* 87, 5791-5793.
19. Arima, K., Kosaka, M., Tamura, G., Imanaka, H., and Sakai, H. (1972) *J Antibiot (Tokyo)* 25, 437-444.
20. Sato, S., Iwata, F., Yamada, S., Kawahara, H., and Katayama, M. (2011) *Bioorg Med Chem Lett* 21, 7099-7101.
21. Thurston D. E. and Bose D. S., *Chem Rev* (1994) 94, 433-465.
22. Damayanthi, Y., et al.; *Journal of Organic Chemistry* (1999), 64, 290-292.
23. Kumar, et al., *Heterocyclic Communications* (2002) 8, 19-26.
24. Kumar, R, Lown, J. W.; *Oncology Research*, (2003) 13, 221-233.
25. Baraldi, P. G. et al., *Journal of Medicinal Chemistry* (1999) 42, 5131-5141.
26. Wells, G., et al., *Proc. Am. Assoc. Canc. Res.* (2003) 44, 452.
27. Thurston, D. E.; Howard, P. W. WO 2004/043963.
28. Farmer, J. D., Rudnicki, S. M., and Suggs, J. W. (1988) *Tetrahedron Lett* 29, 5105-5108;
29. Bose, D. S., Thompson, A. S., Ching, J. S., Hartley, J. A., Berardini, M. D., Jenkins, T. C., Neidele, S., Hurley, L. H., and Thurston, D. E. (1992) *J. Am. Chem. Soc.* 114, 4939.

30. Gregson, S. J., Howard, P. W., Hartley, J. A., Brooks, N. A., Adams, L. J., Jenkins, T. C., Kelland, L. R., and Thurston, D. E. (2001) *J Med Chem* 44, 737-748.
31. Jenkins, T. C.; Hurley, L. H., Neidle, S., and Thurston, D. E. (1994) *J Med Chem* 37, 4529-4537.
32. Wu, J., Clingen, P. H., Spanswick, V. J., Mellinas-Gomez, M., Meyer, T., Puzanov, I., Jodrell, D., Hochhauser, D., and Hartley, J. A. (2013) *Clin Cancer Res* 19, 721-730.
33. Reddy, B. S., Damayanthi, Y., and Lown, J. W. (2000) *Anticancer Drug Des* 15, 225-238.
34. Kamal, A., Khan, M. N., Srikanth, Y. V., Reddy, K. S., Juvekar, A., Sen, S., Kurian, N., and Zingde, S. (2008) *Bioorg Med Chem* 16, 7804-7810.
35. Kamal, A., Srinivas, O., Ramulu, P., Ramesh, G., and Kumar, P. P. (2003) *Bioorg Med Chem Lett* 13, 3577-3581.
36. Al-Said, N. H. J. *Heterocycl. Chem.* (2006), 43, 1091.
37. Cooper, N.; Hagan, D. R.; Tiberghien, A.; Ademefun, T.; Matthews, C. S.; Howard, P. W.; Thurston, D. E. (2002) *Chem. Commun.* 16, 1764.
38. Tiberghien, A. C.; Hagan, D.; Howard, P. W.; Thurston, D. E. (2004) *Bioorg. Med. Chem. Lett.*, 14, 5041.
39. Madani, H.; Thompson, A. S.; Threadgill, M. D. (2002) *Tetrahedron* 58, 8107.
40. Kitamura, T.; Sato, Y.; Mori, M. (2004) *Tetrahedron* 60, 9649.
41. Katsifis, A. G.; McPhee, M. E.; Ridley, D. D. (1998) *Aust. J. Chem.* 51, 1121.
42. Kamal, A.; Reddy, B. S. P.; Reddy, B. S. N. (1996) *Tetrahedron Lett.* 37, 6803.
43. Kamal, A.; Reddy, K. L.; Reddy, G. S. K.; Reddy, B. S. N. (2004) *Tetrahedron Lett.*, 45, 3499.
44. Kamal, A.; Laxman, E.; Laxman, N.; Rao, N. V. (2000) *Bioorg. Med. Chem. Lett.*, 10, 2311.
45. Kamal, A.; Laxman, E.; Arifuddin, M. (2000) *Tetrahedron Lett.*, 41, 7743.
46. Kamal, A.; Babu, A. H.; Ramana, A. V.; Ramana, K. V.; Bharathi, E. V.; Kumar, M. S. (2005) *Bioorg. Med. Chem. Lett.*, 15, 2621.
47. Clark, R. L.; Carter, K. C.; Mullen, A. B.; Coxon, G. D.; Owusu-Dapaah, G.; McFarlane, E.; Duong Thi, M. D.; Grant, M. H.; Tettey, J. N.; Mackay, S. P. (2007) *Bioorg. Med. Chem. Lett.*, 17, 624.
48. Hu, W. P.; Wang, J. J.; Lin, F. L.; Lin, Y. C.; Lin, S. R.; Hsu, M. H. (2001) *J. Org. Chem.*, 66, 2881.
49. Kang, G. D.; Howard, P. W.; Thurston, D. E. (2003) *Chem. Commun.*, 14, 1688.
50. Correa, A.; Tellitu, I.; Dominguez, E.; Moreno, I.; Sanmartin, R. (2005) *J. Org. Chem.*, 70, 2256.
51. Kraus, G. A.; Liu, P. (1995) *Tetrahedron Lett.*, 36, 7595.
52. Artico, M.; De Martino, G.; Giuliano, R.; Massa, S.; Porretta, G. C. (1969) *J. Chem. Soc., Chem. Commun.*, 671.
53. Thurston, D. E.; Langley, D. R. (1986) *J. Org. Chem.*, 51, 705.
54. Langlois, N.; Rojas-Rousseau, A.; Gaspard, C.; Werner, G. H.; Darro, F.; Kiss, R. (2001) *J. Med. Chem.*, 44, 3754.
55. Rojas-Rousseau, A.; Langlois, N. (2001) *Tetrahedron*, 57, 3389.
56. Kamal, A.; Reddy, B. S. N.; Reddy, B. S. P. (1997) *Bioorg. Med. Chem. Lett.*, 7, 1825.
57. Kamal, A.; Rao, N. V. (1996) *Chem. Commun.*, 3, 385.
58. Kamal, A.; Laxman, E.; Reddy, P. S. M. M. (2000) *Synlett*, 10, 1476.
59. Kamal, A.; Reddy, P. S. M. M.; Reddy, D. R. (2003) *Tetrahedron Lett.*, 44, 2857.
60. Langley, D. R. & Thurston, D. E., (1987) *J. Organic Chemistry*, 52, 91-97.
61. Thurston, D. E.; Bose, D. S.; Thompson, A. S.; Howard, P. W.; Leoni, A.; Croker, S. J.; Jenkins, T. C.; Neidle, S.; Hartley, J. A.; Hurley, L. H. (1996) *J. Org. Chem.*, 61, 8141.
62. Kumar, R.; Lown, J. W. (2003) *Mini-Rev. Med. Chem.*, 3, 323.
63. Reddy, B. S. P.; Damayanthi, Y.; Lown, J. W. (1999) *Synlett*, 7, 1112.
64. Matsumoto, T.; Aoyama, T.; Shioiri, T. (1996) *Tetrahedron*, 52, 13521.
65. Matsumoto, T.; Matsunaga, N.; Kanai, A.; Aoyama, T.; Shioiri, T.; Osawa, E. (1994) *Tetrahedron*, 50, 9781.
66. Eguchi, S.; Yamashita, K.; Matsushita, Y.; Kakehi, A. (1995) *J. Org. Chem.*, 60, 4006.
67. Molina, P.; Diaz, I.; Tarraga, A. (1995) *Tetrahedron*, 51, 5617.
68. Fukuyama, T.; Liu, G.; Linton, S. D.; Lin, S. C.; Nishino, H. (1993) *Tetrahedron Lett.*, 34, 2577.
69. Gregson, S. J.; Howard, P. W.; Corcoran, K. E.; Barcella, S.; Yasin, M. M.; Hurst, A. A.; Jenkins, T. C.; Kelland, L. R.; Thurston, D. E. (2000) *Bioorg. Med. Chem. Lett.*, 10, 1845.
70. Gregson, S. J.; Howard, P. W.; Barcella, S.; Nakamya, A.; Jenkins, T. C.; Kelland, L. R.; Thurston, D. E. (2000) *Bioorg. Med. Chem. Lett.*, 10, 1849.
71. Gregson, S. J.; Howard, P. W.; Corcoran, K. E.; Jenkins, T. C.; Kelland, L. R.; Thurston, D. E. *Bioorg. Med. Chem. Lett.* 2001, 11, 2859.
72. Gregson, S. J.; Howard, P. W.; Thurston, D. E. (2003) *Bioorg. Med. Chem. Lett.*, 13, 2277.
73. Kremer, K. (2003) *Macromolecular Chemistry and Physics* 204, 257-264.
74. Case, D. A., Darden, T. A., Cheatham III, T. E., Simmerling, C. L., Wang, J., Duke, R. E., Luo, R., Walker, R. C., Zhang, W., Merz, K. M., Roberts, B., Wang, B., Hayik, S., Roitberg, A., Seabra, G., Kolossvary, I., Wong, K. F., Paesani, F., Vanicek, J., Liu, J., Wu, X., Brozell, S. R., Steinbrecher, T., Gohlke, H., Cai, Q., Ye, X., Wang, J., Hsieh, M.-J., Cui, G., Roe, D. R., Mathews, D. H., Seetin, M. G., Sagui, C., Babin, V., Luchko, T., Gusarov, S., Kovalenko, A., Kollman, P. A. (2010) AMBER 11, University of California, San Francisco, 2010.
75. Perez, A., Marchan, I., Svozil, D., Sponer, J., Cheatham, T. E., 3rd, Laughton, C. A., and Orozco, M. (2007) *Biophys J* 92, 3817-3829.
76. Ryckaert, J.-P., Ciccotti, G., and Berendsen, H. J. C. (1977) *Journal of Computational Physics* 23, 327-341.
77. Wang, H., and Laughton, C. A. (2009) *Phys Chem Chem Phys* 11, 10722-10728.
78. Fogolari, F., Zuccato, P., Esposito, G., and Viglino, P. (1999) *Biophys J* 76, 1-16.
79. Howard, P. W.; Gregson, S. J.; WO 2005/085251.
80. Horwitz, S. B., Chang, S. C., Grollman, A. P., and Bořkovec, A. B. (1971) *Science* 174, 159-161.
81. Borkovec, A. B., Chang, S. C., and Horwitz, S. B. (1971) *J Econ Entomol* 64, 983-984.
82. Rahman, K. M., Jackson, P. J., James, C. H., Basu, B. P., Hartley, J. A., de la Fuente, M., Schatzlein, A., Robson, M., Pedley, R. B., Pepper, C., Fox, K. R., Howard, P. W., and Thurston, D. E. (2013) *J Med Chem.* 56, 2911-35.
83. Howard, P. W., Thurston, D. E.; Wells, G. WO 2007/039752.
84. Wuts, P. G. M. and Greene, T. W., Protective Groups in Organic Synthesis, 4th Edition, Wiley-Interscience, 2007.
85. Kocienski, P., *Protective Groups*, 3rd Edition, Thieme (2005).
86. Howard, P. W., Thurston, D. E.; Rahman, K. M. WO 2013/164593.
87. Dong, Q.; Anderson, C. E.; Ciufolini, M. A. (1995) *Tetrahedron Lett.*, 36, 5681.

88. David E. Bergbreiter, David P. Rainville *J. Org. Chem.*, (1976) 41, 3031-3033.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. A compound of formula (I):

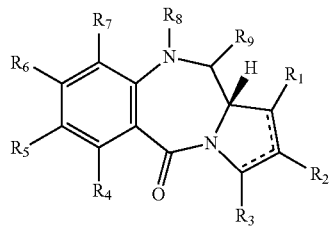

(I)

and salts or solvates thereof, wherein:

the dotted lines indicates the optional presence of a double bond between C1 and C2 or C2 and C3;

$R_2$ and $R_3$ are independently selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN;

$R_4$, $R_5$, $R_6$ and $R_7$ are independently selected from H, R, OH, OR, SH, SR, $NH_2$, NHR, NRR', $CO_2H$, $CH_2$—$CO_2H$, $CO_2R$, $CH_2$—$CO_2R$, $NO_2$, $Me_3Sn$ and halo;

R and R' are independently selected from optionally substituted $C_{1-12}$ alkyl, $C_{2-12}$ alkenyl, $C_{3-20}$ heterocyclyl, $C_{4-20}$ heterocyclalkyl, $C_{5-20}$ heterocyclalkenyl, $C_{3-20}$ heteroaryl, $C_{4-32}$ heteroaralkyl, $C_{5-32}$ heteroaralkenyl, $C_{5-20}$ aryl groups $C_{6-32}$ aralkyl and $C_{7-32}$ aralkenyl; and either:
 (i) $R_8$ and $R_9$ together form a double bond;
 (ii) $R_8$ is H and $R_9$ is OH; or
 (iii) $R_8$ is H and $R_9$ is $OR^A$ and $R^A$ is $C_{1-6}$ alkyl;

and where (a) the compound is a dimer with each monomer being the same or different and being of formula (I) where $R_1$ of the first monomer and $R'_1$ of the second monomer form together a bridge having the formula X-L-X'-linking the monomers;

(b) the compound is a dimer with each monomer being the same or different and being of formula (I) where $R_1$ of the first monomer and $R'_6$ of the second monomer, or $R_6$ of the first monomer and $R'_1$ of the second monomer, form together a bridge having the formula X-L-X'-linking the monomers;

and the remaining $R_1$ of the first monomer or $R'_1$ of the second monomer that does not form the bridge is selected from H, R, OH, OR, $NH_2$, NHR, NRR', $CH_2$—OR, =O, =CH—R, =$CH_2$, $CH_2$—$CO_2R$, $CH_2$—$CO_2H$, $CH_2$—$SO_2R$, O—$SO_2R$, $CO_2H$, $CO_2R$, COR, CN, NR"R''' ($C_{1-12}$ alkylene)-C(O)NR",R''' and ($C_{2-12}$ alkenylene)-C(O)NR'R" and halo; or (c) $R_1$ has the formula:

-X-L-X'-D and wherein:

X is selected from O, S, NR", =CR"—, CR"R''', CR"R'''O, C(=O), C(=O)NR", NR"C(=O), O—C(O) and C(O)—O;

L is selected from an amino acid, a peptide chain having from 2 to 6 amino acids, an alkylene chain containing from 2 to 12 carbon atoms which may contain one or more carbon-carbon double or triple bonds, a paraformaldehyde chain —$(OCH_2)_{1-12}$—, a polyethylene glycol chain —$(OCH_2CH_2)_{1-6}$—, which chains may be interrupted by one or more hetero-atoms and/or $C_{3-20}$ heteroaryl and/or $C_{5-20}$ aryl groups;

X' is selected from O, S, NR", =CR"—, CR"R''', CR"R'''O, C(=O), C(=O)NR', NR"C(=O), O—C(O) and C(O)—O or is absent;

R" and R''' are independently selected from H, optionally substituted $C_{1-12}$ alkyl; and D has the formula (II) or (III):

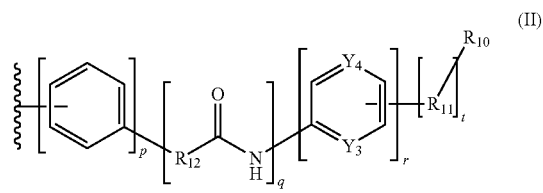

(II)

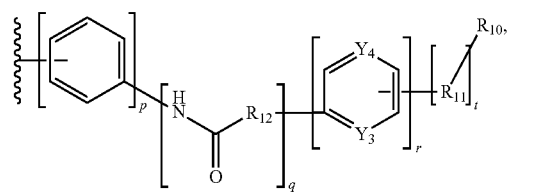

(III)

p is 0 or 1;
q is 1, 2, 3, 4, 5 or 6;
r is o or 1;
t is o or 1
$Y_3$ is N or CH;
$Y_4$ is N or CH; wherein at least one of $Y_3$ and $Y_4$ is CH;
$R_{10}$ is H, Z—R", Z—$CO_2R$", Z—C(=O)—NH—$(CH_2)_{1-6}$—NR"R''', and Z—C(=O)—NH—$(CH_2)_{1-6}$—C(=NH)NR"R''';
Z is absent or is selected from $C_{3-20}$ heteroaryl, $C_{1-6}$ alkyl substituted $C_{3-20}$ heteroaryl, —$(CH_2)_n$—$C_{3-20}$ heterocyclyl, and —O—$(CH_2)_n$—$C_{3-20}$ heterocyclyl group;
n is 0, 1, 2, 3 or 4;
$R_{11}$ is an optionally substituted $C_{3-20}$ heteroaryl; and
$R_{12}$ is an optionally substituted $C_{3-20}$ heteroaryl.

2. A compound of formula (I) according to claim 1, wherein $R_2$ is selected from H, $CH_2$—$CO_2R$, $CH_2$—$CO_2H$, $CH_2OH$, $CH_2OR$.

3. A compound of formula (I) according to claim 1 wherein $R_2$ is an optionally substituted alkenyl, aryl, heteroaryl, aralkyl or heteroaralkyl group which contains at least one double bond which forms part of a conjugated system with a double bond of the c-ring.

4. A compound of formula (I) according to claim 1, wherein $R_4$ is H.

5. A compound of formula (I) according to claim 1, wherein $R_5$ is selected from H, R, OH, OR and halo.

6. A compound of formula (I) according to claim 1, wherein $R_6$ is selected from H, R, OH, OR and halo.

7. A compound of formula (I) according to claim 1, wherein $R_7$ is H.

8. A compound of formula (I) according to claim 1, wherein X is selected from O, =CR"—, C(=O)NR" and NR"C(=O).

9. A compound of formula (I) according to claim 1, wherein X' is selected from O, =CR"—, C(=O)NR" and NR"C(=O).

10. A compound of formula (I) according to claim 1, wherein X is the same as X'.

11. A compound of formula (I) according to claim 1, wherein L is an alkylene chain containing from 3 to 12 carbon atoms which may contain one or more carbon-carbon double or triple bonds.

12. A compound of formula (I) according to claim 1, wherein D has the formula (II) or (III) and $R_{11}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

13. A compound of formula (I) according to claim 1, wherein D has the formula (II) or (III) and $R_{12}$ is selected from N-methylpyrrolylene, furanylene, thiophenylene, N-methylimidazolylene, oxazolylene, thiazolylene, indolylene, N-methylindolylene, benzofuranylene, benzothiophenylene, benzimidazolylene, N-methylbenzoimidazolylene, benzooxazolylene and benzothiazolylene.

14. A compound of formula (I) according to claim 1, wherein D has the formula (II) or (III), Z is absent and $R_{10}$ is $CO_2R"$.

15. A compound of formula (I) according to claim 1, wherein the compound is a dimer with each monomer being the same and being of formula (I).

16. A compound of formula (I) according to claim 1, wherein the compound is a dimer of the following structure (XIX):

(XIX)

or has the following structure:

and salts or solvates thereof, wherein:
the dotted lines indicates the optional presence of a double bond between C1 and C2 or C2 and C3;
$R_2$, $R'_2$, $R_3$ and $R'_3$ are independently selected from H, $NH_2$, $NH(C_{1-6}$ alkyl), $CO_2(C_{1-6}$ alkyl), $CH_2$—$CO_2(C_{1-6}$ alkyl), $CO_2H$ and $CH_2$—$CO_2H$;

$R_4$, $R'_4$, $R_7$ and $R'_7$ are independently selected from H, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl);

$R_5$, $R'_5$, $R_6$ and $R'_6$ are independently selected from H, O—$C_{1-6}$ alkyl, $OCH_2Ph$, $NH_2$, $NH(C_{1-6}$ alkyl), $CO_2H$, $CH_2$—$CO_2H$, $CO_2(C_{1-6}$ alkyl) and $CH_2$—$CO_2(C_{1-6}$ alkyl);

and either:
(i) $R_8$ and $R_9$ together form a double bond, and $R'_8$ and $R'_9$ together form a double bond;
(ii) $R_8$ is H and $R_9$ is OH, and $R'_8$ is H and $R'_9$ is OH; or
(iii) $R_8$ is H and $R_9$ is $OR^A$ and $R^A$ is $C_{1-6}$ alkyl, and $R'_8$ is H and $R'_9$ is $OR'^A$ and $R'^A$ is $C_{1-6}$ alkyl;

and wherein:
X is selected from O, =CH—, C(=O)NH and NHC(=O);
L is selected from a peptide chain having from 2 to 5 amino acids; an alkylene chain containing from 3 to 11 carbon atoms which may contain one or more carbon-carbon double or triple bonds; —$(OCH_2)_{1-12}$— and —$(OCH_2CH_2)_{1-5}$—;
X' is selected O, =CH—, C(=O)NH and NHC(=O) or is absent;
D is:

(VIII)

(IX)

wherein:
q is 1, 2, 3, 4, 5 or 6;
r is 0 or 1;
t is 0 or 1
Y, $Y_1$ and $Y_2$ are selected from CH, CH and N—$CH_3$; CH, N—$CH_3$ and CH; N, CH and N—$CH_3$; N, N—$CH_3$ and CH;
$Y_3$ is N or CH;
$Y_4$ is N or CH; wherein at least one of $Y_3$ and $Y_4$ is CH;
$Y_5$, $Y_6$ and $Y_7$ are selected from CH, CH and N—$CH_3$; CH, N—$CH_3$ and CH; N, CH and N—$CH_3$; N, N—$CH_3$ and CH;
$R_{10}$ is H, Z—H, Z—$C_{1-6}$ alkyl, Z—$CO_2H$ and Z—$CO_2C_{1-6}$ alkyl; and
Z is absent or is selected from benzofuranyl, benzothiophenyl, indolyl and N-methyl indolyl.

17. A compound of formula (I) according to claim 1, wherein the compound is:

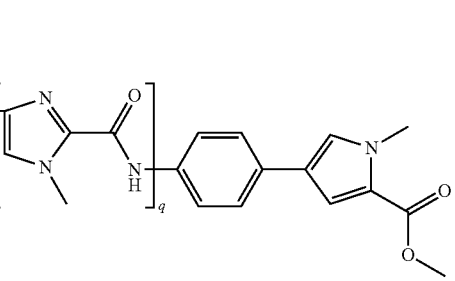

wherein f is selected from 1, 2, 3, 4, 5, 6, 7, 8, 9 and 10; and q is selected from 1, 2, 3, 4, 5 and 6.

18. A compound of formula (I) according to claim 1, wherein the compound is a dimer of the following structure (XIX):

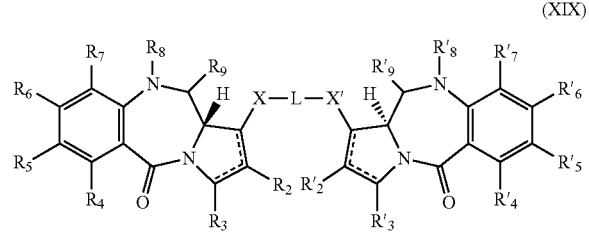

(XIX)

and salts or solvates thereof, wherein:

the dotted lines indicates the optional presence of a double bond between C1 and C2 or C2 and C3;

$R_2$, $R'_2$, $R_3$, $R'_3$, $R_4$, $R'_4$, $R_7$ and $R'_7$ are H;

$R_5$, $R'_5$, $R_6$ and $R'_6$ are independently selected from O—$C_{1-6}$ alkyl and $OCH_2Ph$, and either:

(i) $R_8$ and $R_9$ together form a double bond, and $R'_8$ and $R'_9$ together form a double bond;

(ii) $R_8$ is H and $R_9$ is OH, and $R'_8$ is H and $R'_9$ is OH; or (iii) $R_8$ is H and $R_9$ is $OR^A$ and $R^A$ is $C_{1-6}$ alkyl, and $R'_8$ is H and $R'_9$ is $OR'^A$ and $R'^A$ is $C_{1-6}$ alkyl;

and wherein:

X is selected from O, =CH—, C(=O)NH and NHC(=O);

L is selected from an alkylene chain containing from 3 to 11 carbon atoms; and

X' is selected O, =CH—, C(=O)NH and NHC(=O).

19. A method for treating a proliferative disease in a subject, the method comprising the step of administering a compound of claim 1 to the subject, wherein the proliferative disease is selected from breast cancer, ovarian cancer and leukemia.

20. A pharmaceutical composition comprising a compound of claim 1 and a pharmaceutically acceptable carrier or diluent.

* * * * *